United States Patent
Madison et al.

(10) Patent No.: US 6,677,473 B1
(45) Date of Patent: Jan. 13, 2004

(54) PLASMINOGEN ACTIVATOR INHIBITOR ANTAGONISTS

(75) Inventors: Edwin L. Madison, San Diego, CA (US); Terence K. Brunck, Sante Fe, NM (US); Joseph Edward Semple, San Diego, CA (US); Marguerita Lim-Wilby, La Jolla, CA (US); Kent E. Pryor, San Diego, CA (US); Ronald D. Lewis, II, San Diego, CA (US); David F. Duncan, San Diego, CA (US); C. Maxwell Lawrence, San Diego, CA (US)

(73) Assignee: Corvas International INC, San Diego, CA (US)

( * ) Notice: Subject to any disclaimer, the term of this patent is extended or adjusted under 35 U.S.C. 154(b) by 29 days.

(21) Appl. No.: 09/716,036

(22) Filed: Nov. 17, 2000

Related U.S. Application Data

(63) Continuation-in-part of application No. 09/580,535, filed on May 26, 2000, and a continuation-in-part of application No. 09/444,172, filed on Nov. 19, 1999, which is a continuation-in-part of application No. 09/580,535.
(60) Provisional application No. 60/185,564, filed on Feb. 28, 2000.

(51) Int. Cl.[7] ............................................. C07C 69/76
(52) U.S. Cl. ........................... 560/52; 560/9; 560/11; 562/426; 562/429; 562/460; 564/162; 564/163; 568/332
(58) Field of Search .................... 560/52, 9, 11; 562/426, 429, 460; 564/162, 163; 568/362

(56) References Cited

U.S. PATENT DOCUMENTS

| | | | |
|---|---|---|---|
| 3,710,795 A | 1/1973 | Higuchi et al. | 128/260 |
| 3,794,729 A | 2/1974 | Wohl et al. | 424/337 |
| 3,882,230 A | 5/1975 | Holland | |
| RE28,819 E | 5/1976 | Thompson | 424/243 |
| 3,983,164 A | 9/1976 | Thorne et al. | |
| 4,044,126 A | 8/1977 | Cook et al. | 424/243 |
| 4,221,919 A | 9/1980 | Grimova et al. | |
| 4,323,691 A * | 4/1982 | Ours et al. | |
| 4,328,245 A | 5/1982 | Yu et al. | 424/305 |
| 4,358,603 A | 11/1982 | Yu | 560/2 |
| 4,364,923 A | 12/1982 | Cook et al. | 424/46 |
| 4,409,239 A | 10/1983 | Yu | 424/305 |
| 4,410,545 A | 10/1983 | Yu et al. | 424/305 |
| 4,414,209 A | 11/1983 | Cook et al. | 424/243 |
| 4,522,811 A | 6/1985 | Eppstein et al. | 514/2 |
| 4,764,359 A | 8/1988 | Lemelson | 424/1.1 |
| 4,847,195 A | 7/1989 | Khanna et al. | 435/7 |
| 5,026,558 A | 6/1991 | Hwang | 424/400 |
| 5,033,252 A | 7/1991 | Carter | 53/425 |
| 5,052,558 A | 10/1991 | Carter | 206/439 |
| 5,262,170 A | 11/1993 | Anderson et al. | 424/94.64 |
| 5,323,907 A | 6/1994 | Kalvelage | 206/531 |
| 5,371,072 A | 12/1994 | Webb et al. | 514/18 |
| 5,456,663 A | 10/1995 | Lemelson | 604/50 |
| 5,492,895 A | 2/1996 | Vlasuk et al. | 514/18 |
| 5,506,134 A | 4/1996 | Soule et al. | 435/240.27 |
| 5,520,913 A | 5/1996 | Anderson et al. | 424/94.64 |
| 5,534,498 A | 7/1996 | Brunck et al. | 514/19 |
| 5,543,391 A | 8/1996 | Yatvin et al. | 514/2 |
| 5,550,213 A | 8/1996 | Anderson et al. | 530/324 |
| 5,585,404 A * | 12/1996 | Norinder et al. | |
| 5,589,154 A | 12/1996 | Anderson | 424/1.41 |
| 5,597,804 A | 1/1997 | Webb et al. | 514/18 |
| 5,637,492 A | 6/1997 | Dawson et al. | 435/217 |
| 5,637,599 A | 6/1997 | Levy et al. | 514/326 |
| 5,639,726 A | 6/1997 | Lawrence et al. | 514/12 |
| 5,646,165 A | 7/1997 | Abelman et al. | 514/315 |
| 5,656,600 A | 8/1997 | Abelman et al. | 514/13 |
| 5,656,645 A | 8/1997 | Tamura et al. | 514/349 |
| 5,658,930 A | 8/1997 | Tamura et al. | 514/318 |
| 5,658,939 A | 8/1997 | Abelman et al. | 514/414 |
| 5,670,479 A | 9/1997 | Abelman et al. | 514/12 |
| 5,681,844 A | 10/1997 | Abelman et al. | 514/423 |
| 5,688,644 A | 11/1997 | Lott et al. | 435/6 |
| 5,696,231 A | 12/1997 | Abelman et al. | 530/331 |

(List continued on next page.)

FOREIGN PATENT DOCUMENTS

| | | |
|---|---|---|
| DE | 2239136 | 3/1973 |
| EP | 0257352 | 8/1987 |
| EP | 0548711 | 12/1992 |
| EP | 0612723 | 2/1994 |
| EP | 0819686 | 1/1998 |
| FR | 0008005 | 5/1967 |
| GB | 1209945 | 10/1970 |
| GB | 1400851 | 7/1975 |
| GB | 2065121 | 12/1980 |
| WO | 9220331 | * 11/1992 |
| WO | 9324442 | 12/1993 |
| WO | 9405153 | 3/1994 |
| WO | 9407492 | 4/1994 |
| WO | 9611904 | 4/1996 |
| WO | 9640048 | * 12/1996 |
| WO | 9746228 | 12/1997 |
| WO | 9911255 | 3/1999 |
| WO | 9920263 | 4/1999 |

OTHER PUBLICATIONS

Certified English Language translation of French Patent No. FR 8005 M; unformatted coded pages to be read in conjunction with the foreign patent.

Certified English Language translation of European Patent No. 0548711; unformatted coded pages to be read in conjunction with the foreign patent.

(List continued on next page.)

*Primary Examiner*—Paul J. Killos
(74) *Attorney, Agent, or Firm*—Heller Ehrman White & McAuliffe LLP; Stephanie L. Seidman; Deb Riega

(57) ABSTRACT

Compounds and pharmaceutical compositions useful as plasminogen activator inhibitor (PAI) antagonists are provided. In particular, methods of antagonizing PAI with substituted and unsubstituted aryl and heteroaryl ethers and thioethers, benzils, benzyl ethers, benzoate esters, sulfones and benzophenones are provided.

34 Claims, 38 Drawing Sheets

U.S. PATENT DOCUMENTS

| | | | |
|---|---|---|---|
| 5,703,208 A | 12/1997 | Semple et al. | 530/331 |
| 5,714,336 A | 2/1998 | Simons et al. | 435/7.9 |
| 5,714,499 A | 2/1998 | Semple et al. | 514/316 |
| 5,714,580 A | 2/1998 | Brunck et al. | 530/331 |
| 5,736,576 A | 4/1998 | Kun et al. | 514/570 |
| 5,739,112 A | 4/1998 | Brunck et al. | 514/19 |
| 5,747,449 A | 5/1998 | Lasters et al. | 514/12 |
| 5,750,530 A | 5/1998 | Bryans et al. | 514/255 |
| 5,770,600 A | 6/1998 | Abelman et al. | 514/237.2 |
| 5,776,927 A | 7/1998 | Abelman et al. | 514/210 |
| 5,807,980 A | 9/1998 | Lasters et al. | 530/324 |
| 5,820,879 A | 10/1998 | Fernandez et al. | 424/450 |
| 5,843,442 A | 12/1998 | Soule et al. | 424/145.1 |
| 5,863,894 A | 1/1999 | Vlasuk et al. | 514/12 |
| 5,864,009 A | 1/1999 | Vlasuk et al. | 530/350 |
| 5,866,542 A | 2/1999 | Vlasuk et al. | 514/12 |
| 5,866,543 A | 2/1999 | Vlasuk et al. | 514/12 |
| 5,866,610 A | 2/1999 | Lang et al. | |
| 5,869,454 A | 2/1999 | Webb et al. | 514/18 |
| 5,872,098 A | 2/1999 | Vlasuk et al. | 514/12 |
| 5,883,077 A | 3/1999 | Brunck et al. | 514/19 |
| 5,883,107 A | 3/1999 | Levy et al. | 514/305 |
| 5,886,146 A | 3/1999 | Vlasuk et al. | 530/331 |
| 5,891,877 A | 4/1999 | Brocchini et al. | 514/235.8 |
| 5,902,812 A | 5/1999 | Brocchini et al. | 514/253 |
| 5,922,775 A | 7/1999 | Kun et al. | 514/685 |
| 5,932,733 A | 8/1999 | Semple et al. | 546/188 |
| 5,945,275 A | 8/1999 | Vlasuk et al. | 435/5 |
| 5,955,294 A | 9/1999 | Vlasuk et al. | 435/13 |
| 5,955,576 A | 9/1999 | Vlasuk et al. | 530/331 |
| 5,977,056 A | 11/1999 | Powell-Jones et al. | 514/2 |
| 6,008,351 A | 12/1999 | Tamura et al. | 544/301 |
| 6,011,047 A | 1/2000 | Semple et al. | 514/327 |
| 6,011,158 A | 1/2000 | Tamura et al. | 546/309 |
| 6,017,958 A | 1/2000 | Kun et al. | 514/532 |
| 6,025,472 A | 2/2000 | Abelman et al. | 530/331 |
| 6,034,215 A | 3/2000 | Semple et al. | 530/331 |
| 6,040,441 A | 3/2000 | Vlasuk et al. | 536/252 |
| 6,046,318 A | 3/2000 | Vlasuk et al. | 536/23.5 |
| 6,087,467 A | 7/2000 | Marrocco, III et al. | 528/125 |
| 6,087,487 A | 7/2000 | Vlasuk et al. | 536/23.5 |
| 6,090,916 A | 7/2000 | Vlasuk et al. | 530/350 |
| 6,103,486 A | 8/2000 | Simons et al. | 435/7.93 |

OTHER PUBLICATIONS

Certified English Language translation of International PCT application No. WO 93/24442; unformatted coded pages to be read in conjuction with the foreign patent.

Certified English Language translation of International PCT application No. WO 99/11255; unformatted coded pages to be read in conjunction with the foreign patent.

Derwent #000925695, WPI Acc No: 1973–02913U/197303 (citing French Patent No. FR 8005 M).

Derwent #009512849, WPI Acc No: 1993–206385/199326 (citing European Patent No. 0548711).

Derwent #012398862, WPI Acc No: 1999–204969/199917 (citing International PCT application No. WO 99/11255).

Kuchar et al., "Use of Qsar in design antiinflammatory fluorinated arylalkanoic acids," *Collect. Czech. Chem. Commun.* 55:296–306 (1990).

Kuchar et al., "Benzyloxyarylaliphatic acids: synthesis and quantitative relations between structure and antinflammatory activity," *Collect. Czech. Chem. Commun.* 47:2514–2524 (1982).

Perrier and Labelle, "Liquid–phase synthesis with solid–phase workup: application to multistep and combinatorial synthesis," *J. Org. Chem.* 64:2110–2113 (1999); supporting information .. 1–18 containing spectral/structural information.

Derwent# XP000942576 WPI Acc. No. 1973–19808U/ 197315 (citing German Application No. DE2239136, published Mar. 29, 1973).

Strandberg et al. Variants of Tissue–type Plasminogen Activator with Substantially Enhanced Response and Selectively toward Fibrin Co–factors, *The Journal of Biological Chemistry*, 270(40): 23444–9 (1995).

Tachies et al. Converting Tissue–type plasminogen Activator into a Zymogen, *The Journal of Biological Chemistry*, 271(46): 28749–52 (1996).

Tachies et al. Variants of Tissue–type Plasminogen Activator that Display Extraordinary Resistance to Inhibition by the Serpin Plasminogen Activator Inhibitor Type 1, *The Journal of Biological Chemistry*, 272(23): 14580–5 (1997).

Tachies et al. Converting Tissue Type Plasminogen Activator into a Zymogen, *The Journal of Biological Chemistry*, 272(1): 28–31 (1997).

Tachias et al., Variants of Tissue–type Plasminogen Activator Which Display Substantially Enhanced Stimulation by Fibrin, *The Journal of Biological Chemistry*, 270(31): 18319–22 (1995).

Tamura et al. Sythesis and Biological Activity of Peptidyl Aldehyde Urokinase Inhibitors, *Bioorganic & Medicinal Chemistry Letters*, 10:983–7 (2000).

Vlasuk et al., The New Anticoagulants: New Opportunities, New Issues, *Arch. Pathol. Lab. Med.*, 122:812–4 (1998).

Xue et al. Comparison of the Effects of Apo(a) Kringle IV–10 and Plasminogen Kringles on the Interactions of Lipoprotein (a) with Regulatory Molecules, *Thromb Haemost*, 81:428–35 (1999).

Zhang et al. Distinct Contributions of Residue 192 to the Specificity of Coagulation and Fibrinolytic Serine Proteases, *The Journal of Biological Chemistry*, 274(11): 7153–6 (1999).

Madison et al., Serpin–resistant mutants of human tissue–type plasminogen activator, *Nature* 339:721–724 (1989).

Madison EL., Studies of Serpins Unfold at a Feverish Pace, *J. Clin. Invest.*, 94: 2174–5 (1994).

Madison et al., Substrate Specificity of Tissue Type Plasminogen Activator: Characterization of the Fibrin Independent Specificity of t–PA for Plasmiongen, *The Journal of Biological Chemistry*, 270(13): 7558–62 (1995).

Madison et al., Converting Tissue Plasminogen Activator to a Zymogen: A Regulatory Triad of Asp–His–Ser, *Science* 262:419–421 (1993).

Madison et al., Amino acid residues that affect interaction of tissue–type plaminogen activator with plasminogen activator inhibitor 1, *Proc. Natl. Acad. Sci. USA* 87:3530–3533 (1990).

March, Advanced Organic Chemistry, *John Wiley & Sons, Inc.*, New York p. 804 (1985).

Nilsson et al., A New Kit for the Determination of Tissue Plasminogen Activator and its inhibitor in Blood, *Fibrinolysis* 1:163–168 (1987).

Nogrady, Medicinal Chemistry: A Biochemical Approach, *Oxford University Press, New York*, pp.388–392 (1985).

Olah, Friedel–Crafts and Related Reactions, *Interscience Publishers*, New York 3:1355–1392 (1964).

Orth et al., Complexes of tissues–type plasminogen activator and its serpin inhibitor plasminogen–activator inhibitor type 1 are internalized by means of the low density lipoprotein receptor–related protein/ α2–macroglobulin receptor; *Proc. Natl. Acad. Sci. USA*, 89: 7422–6 (1992).

Remington's Pharmaceutical Sciences, *Mack Publishing Company, Pennsylvania* (1975).

Salamonczyk et al., A Concise Synthesis of Thyroxine ($T_4$) and 3,5,3 –Triiodo–L–thyronine ($T_3$), *Tetrahedron Letters* 38(40):6965–6968 (1997).

Shobet et al. Inhibitor–Resistant Tissue–Type Plasminogen Activator: An Improved Thrombolytic Agent in Vitro, *Thrombosis and Haemostasis*, 71(1):124–8 (1994).

Smith et al. Protein Loop Grafting to Construct a Variant of Tissue–type Plasminogen Activator That Binds Platelet Integrin αIIbβ3, *The Journal of Biological Chemistry*, 270(51): 30486–90 (1995).

Gilbert, Sulfonation and Related Reactions, *Intersceince Publishers, New York* pp. 62–83 and 87–124 (1995).

Greene et al., Protective Groups in Organic Synthesis, *John Wiley & Sons, Inc., New York* (1981).

Hervio et al. Negative selectivity and the evolution of protease cascades: the specificity of plasmin for peptide and protein and protein substrates, *Chemistry & Biology* 7(6):443–52 (2000).

IUPAC–IUB Commission on Biochemical Nomenclature, Abbreviated Nomenclature of Synthetic Polypeptides (Polymerized Amino Acids), *Biochemistry* 11(5):942–944 (1972).

Ke et al. Identification of a Hydrophobic Exosite on Tissue Type Plasminogen Activator That Modulates Specificity for Plasminogen, *The Journal of Biological Chemistry*, 272(3):1811–6 (1997).

Ke et al. Optimal Subsite Occupany and Design of a Selective Inhibitor of Urokinase, *The Journal of Biological Chemistry*, 272(33): 20456–62 (1997).

Ke et al. Distinguishing the Specificities of Closely Related Proteases, *The Journal of Biological Chemistry*, 272 (26): 16603–9 (1997).

Krishnan et al. Highly Selective Mechanism–Based Thrombin Inhibitors: Structures of Thrombin and Trypsin Inhibited with Rigid Peptidyl Aldehydes, *Biochemistry*, 37: 12094–103 (1998).

Madison et al. Restoration of Serine Protease Inhibitor Interaction by Protein Engineering, *The Journal of Biological Chemistry*, 265(35): 21453–26 (1990).

Madison et al. Probing Structure–Function Relationships of Tissue–Type Plasminogen Activator by Oligonucleotide–Mediated Site–Specific Mutagenesis, *Methods in Enzymology*, 223: 249–71 (1993).

Madison et al. Converting Tissue Plasminogen Activator to a Zymogen: A Regulatory Triad of Asp–His–Ser, *Science*, 262: 419–21 (1993).

Madison et al. Amino acid Residues that affect interaction of tissue–type plasminogen activator with plasminogen activator inhibitor 1, *Proc. Natl. Acad. Sci USA*, 87:3530–33 (1990).

Madison et al. Serpin–resistant mutants of human tissue–type plasminogen activator, *Nature*, 339: 721–4 (1989).

Madison EL., Substrate Specificity of Tissue Type Plasminogen Activator, *Chemistry and Biology of Serpins*, Church et al. (Ed.) Plenum Press: New York (1997).

Bell et al, Synthesis of thyroxine: biomimetic studies, *Can. J. Chem*. 75:873–883 (1997).

Björquist et al., Identification of the Binding Site for a Low–Molecular–Weight Inhibitor of Plasminogen Activator Inhibitor Type 1 by Site–Directed Mutagenesis, *Biochemistry* 37:1227–1234 (1998).

Bonvino et al., Nitro Compounds as Alkylating Reagents in Friedel–crafts Conditions, *Tetrahedron* 37:615–620 (1981).

Charlton et al., Evaluation of a Low Molecular Weight Modulator on Human Plasminogen Activator Inhibitor–1 Activity, *Thrombosis and Haemostasis* 75(5):808–815 (1996).

Charlton et al., XR5118, a novel modulator of plasminogen activator inhibitor–1 (PAI–1), increases endogenous tPA activity in the rat, *Fibrinolysis and Proteolysis* 11(1):51–56 (1997).

Coombs et al., Revisiting Catalysis by Chymotrysin Family Serine Proteases using Peptide Substrates and Inhibitors with Unnatural Main Chains, *The Journal of Biological Chemistry* 274(34):24074–9 (1999).

Coombs et al., Distinct Mechanisms Contribute to Stringent Substrate Specificity of Tissue–type Plasminogen Activator, *The Journal of Biological Chemistry*, 271(8):4461–7 (1996).

Coombs et al., Directing Sequence–specific proteolysis to new Tragets, *The Journal of Biological Chemistry*, 273(8):4323–8 (1998).

Ding et al., Origins of the specificity of tissue–type plasminogen activator, *Proc. Natl. Acad. Sci. USA*, 92:7627–31 (1995).

Evans et al., Synthesis of Diaryl Ethers through the Copper–Promoted Arylation of Phenols with Arylboronic Acids. An Expedient Synthesis of Thyroxine, *Tetrahedron Letters* 39:2937–2940 (1998).

Fay et al., Platelets Inhibit Fibrinolysis In Vitro by Both Plasminogen Activator Inhibitor–1–Dependent and –Independent Mechanisms, *Blood*, 83(2):351–6 (1994).

Fujise et al., A Tissue Plasminogen Activator/P–Selectin Fusion Protein Is an Effective Thrombolytic Agent, *Circulation*, 95(3):715–22 (1997).

Gething et al., Variants of human tissue–type plasminogen activator that lack specific structural domains of the heavy chain, *EMBO J.*, 7(9):2731–40 (1988).

Ansel, *Introduction to Pharmaceutical Dosage Forms, Fourth Edition*, 126 (1985).

Bajou et al., Absence of host plasminogen activator inhibitor 1 prevents cancer invasion and vascularization, *Nat. Med.* 4(8): 923–928 (1998).

\* cited by examiner

| NAME | STRUCTURE |
|---|---|
| (4-hydroxy-3-iodo-5-nitro-phenyl)-phenyl-methanone | 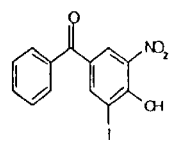 |
| 3,5-diiodo-4-(3-iodo-benzyloxy)- benzoic acid | 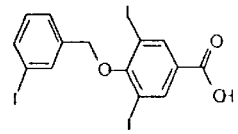 |
| 3,5-diiodo-4-(4-iodo-benzyloxy)- benzoic acid | 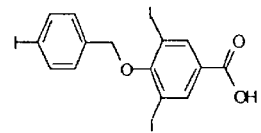 |
| 3,5-diiodo-4-(2-bromo-benzyloxy)- benzoic acid | 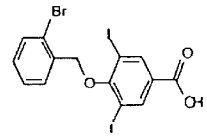 |
| 3,5-diiodo-4-(3-bromo-benzyloxy)- benzoic acid | 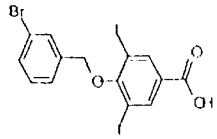 |
| 3,5-diiodo-4-(4-bromo-benzyloxy)- benzoic acid | 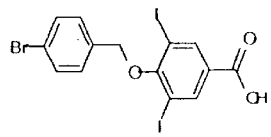 |
| 3,5-diiodo-4-(2-methyl-benzyloxy)- benzoic acid | 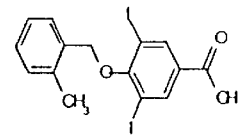 |
| 3,5-diiodo-4-(3-methyl-benzyloxy)- benzoic acid | 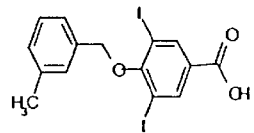 |
| 3,5-diiodo-4-(4-methyl-benzyloxy)- benzoic acid | 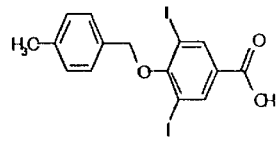 |
| 4-(4-tert-butyl-benzyloxy)-3,5- diiodo-benzoic acid | 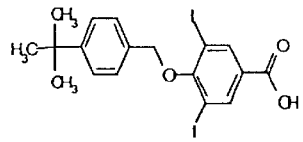 |
| 3,5-diiodo-4-(naphthalen-2-ylmethoxy)-benzoic acid | 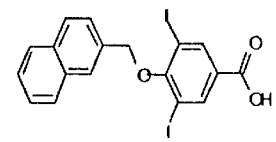 |

FIG. 1A

| NAME | STRUCTURE |
|---|---|
| 4-(biphenyl-2-ylmethoxy)-3,5-diiodo- benzoic acid | 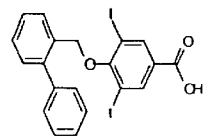 |
| 3,5-diiodo-4-(3-methoxy-benzyloxy)- benzoic acid | 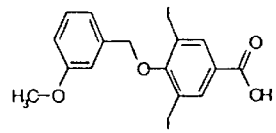 |
| 3,5-diiodo-4-(3-trifluoromethyl-benzyloxy)-benzoic acid | 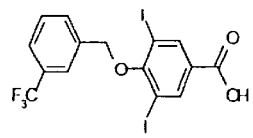 |
| 3,5-diiodo-4-(3-trifluoromethoxy-benzyloxy)-benzoic acid | 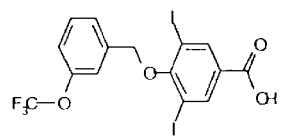 |
| 4-(3-fluoro-benzyloxy)-3,5-diiodo-benzoic acid | 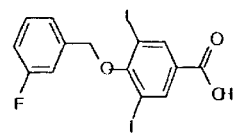 |
| 3,5-diiodo-4-pentafluorophenylmethoxy- benzoic acid | 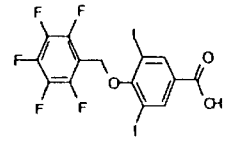 |
| 3,5-dibromo-4-(3-iodo-benzyloxy)-benzoic acid | 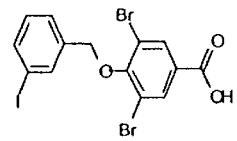 |
| 3,5-dichloro-4-(3-iodo-benzyloxy)-benzoic acid | 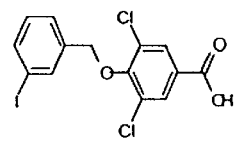 |
| 3-[3,5-diiodo-4-(3-iodo-benzyloxy)-phenyl]-propionic acid | 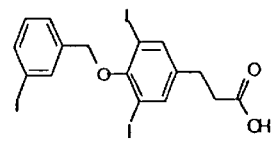 |
| 3-[3,5-diiodo-4-(4-iodo-benzyloxy)-phenyl]-propionic acid | 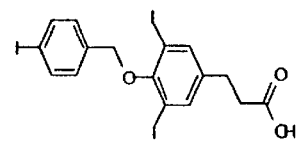 |

FIG. 1B

| NAME | STRUCTURE |
|---|---|
| 3-(4-benzyloxy-3,5-diiodo-phenyl)-propionic acid | 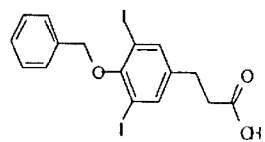 |
| 3-[4-(3-bromo-benzyloxy)-3,5-diiodo-phenyl]-propionic acid | 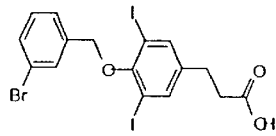 |
| 3-[4-(4-bromo-benzyloxy)-3,5-diiodo-phenyl]-propionic acid | 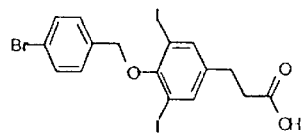 |
| 3,5-dibromo-4-(4-tert-butyl-benzyloxy)-benzoic acid | 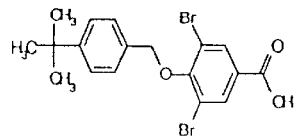 |
| [3,5-diiodo-4-(3-iodo-benzyloxy)-phenyl]-acetic acid | 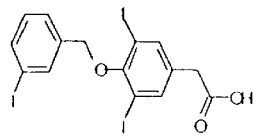 |
| [3,5-diiodo-4-(4-iodo-benzylixy)-phenyl]-acetic acid | 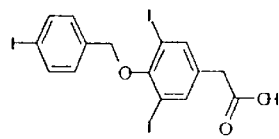 |
| [4-(3-bromo-benzyloxy)-3,5-diiodo-phenyl]-acetic acid | 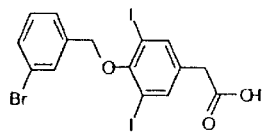 |
| 4-(2-nitro-benzyloxy)-3,5-diiodo-benzoic acid | 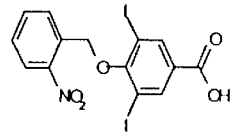 |
| 4-(4-nitro-benzyloxy)-3,5-diiodo-benzoic acid | 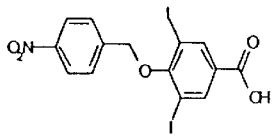 |
| (4-hydroxy-3,5-diiodophenyl)-phenyl-methanone | 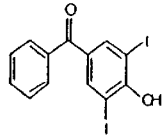 |
| (4-benzoyl-2,6-diiodophenoxy)-acetic acid | 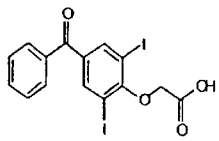 |

FIG. 1C

| NAME | STRUCTURE |
|---|---|
| 4-hydroxy-3,5-diiodobenzoic acid 2-iodobenzyl ester | 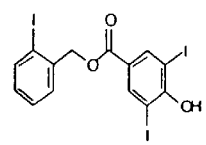 |
| 2-acetylamino-3-[3,5-diiodo-4-(3-iodobenzyloxy)-phenyl]-propionic acid | 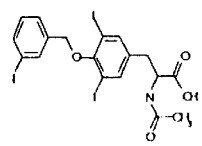 |
| bis-(4-hydroxy-3,5-diiodophenyl)-methanone | 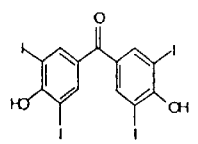 |
| 4-(2-fluorobenzyloxy)-3,5-diiodobenzoic acid | 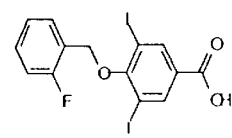 |
| 4-(4-fluorobenzyloxy)-3,5-diiodobenzoic acid | 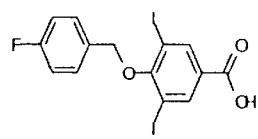 |
| 4-(2-clhorobenzyloxy)-3,5-diiodobenzoic acid | 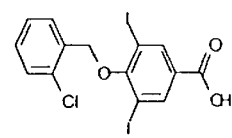 |
| 4-(3-chlorobenzyloxy)-3,5-diiodobenzoic acid | 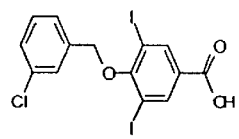 |
| [4-(4-hydroxy-3,5-diiodo-benzoyl)-2,6-diiodo-phenoxy]-acetic acid benzyl ester | 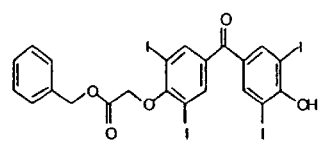 |
| 4-(4-chlorobenzyloxy)-3,5-diiodobenzoic acid | 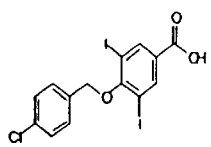 |
| [4-[(6,7-dihydro-5,5,8,8-tetramethyl)naphthyl-2-methoxy]-3,5-diiodobenzoic acid | 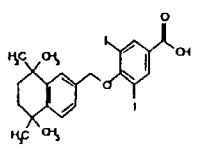 |

FIG. 1D

| NAME | STRUCTURE |
|---|---|
| 4-(1,6-dichlorobenzyloxy)-3,5-diiodobenzoic acid | 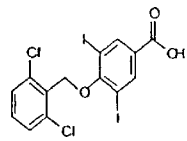 |
| 4-(1,6-difluorobenzyloxy)-3,5-diiodobenzoic acid | 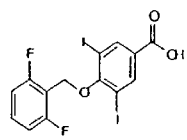 |
| 4-[4-(trifluoromethoxy)-benzyloxy]-3,5-diiodobenzoic acid | 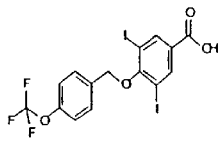 |
| 4-[2-(trifluoromethyl)-benzyloxy]-3,5-diiodobenzoic acid | 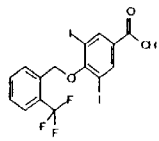 |
| 4-[4-(trifluoromethyl)-benzyloxy]-3,5-diiodobenzoic acid | 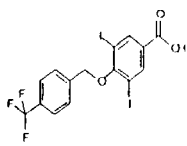 |
| 4-[(2-fluoro-4-bromo)benzyloxy]-3,5-diiodobenzoic acid | 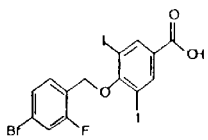 |
| 4-(2-iodo)benzyloxy-3,5-diiodobenzoic acid | 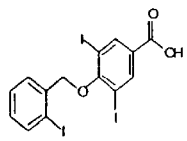 |
| 4-(3-benzoyl)benzyloxy-3,5-diiodobenzoic acid | 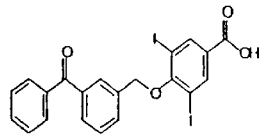 |
| 4-(3,5-dimethoxy)benzyloxy-3,5-diiodobenzoic acid | 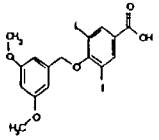 |
| [4-(4-hydroxy-3,5-diiodo-benzoyl)-2,6-diiodo-phenoxy]-acetic acid | 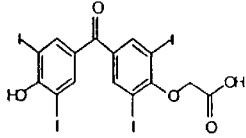 |
| 4-(3-methylnaphthyl-2-methoxy)-3,5-diiodobenzoic acid | 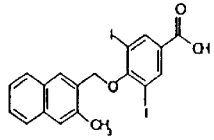 |

FIG. 1E

| NAME | STRUCTURE |
|---|---|
| 4-[N-[(2-benzoyl)phenyl]-methoxyamidyl]-3,5-diiodobenzoic acid | 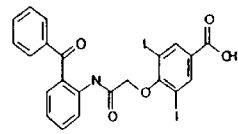 |
| 4-[4-(trifluoromethyl)thio]-benzyloxy-3,5-diiodobenzoic acid | 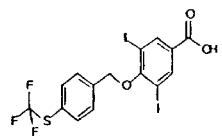 |
| 4-[2-(trifluoromethyl)thio]-benzyloxy-3,5-diiodobenzoic acid | 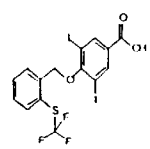 |
| 4-(adamantyl-1-acetyloxy)-3,5-diiodobenzoic acid | 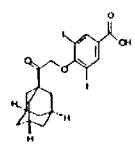 |
| 4-(4-chloro)benzyloxy-3,5-dichlorobenzoic acid | 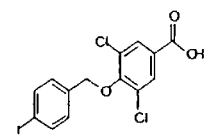 |
| 4-(naphthyl-2-methoxy)-3,5-dichlorobenzoic acid | 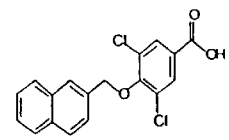 |
| 4-(4-iodo)benzyloxy-3,5-dibromobenzoic acid | 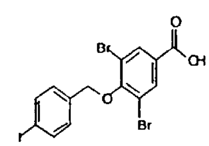 |
| 4-(naphthyl-2-methoxy)-3,5-dibromobenzoic acid | 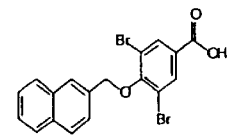 |
| 4-(9H-fluoren-9-yloxy)-3,5-diiodobenzoic acid | 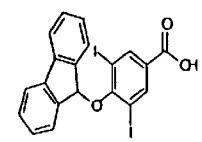 |
| 1,2-bis-(4-hydroxy-3,5-diiodophenyl)-ethane-1,2-dione | 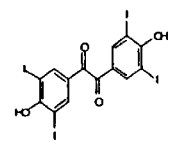 |

FIG. 1F

| NAME | STRUCTURE |
|---|---|
| (4-fluorophenyl)-(4-hydroxy-3,5-diiodophenyl)-methanone | 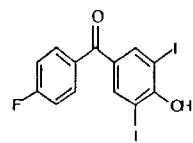 |
| 4-[3-(2-fluoro)phenoxybenzyloxy]-3,5-diiodobenzoic acid | 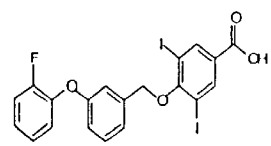 |
| 4-[2-(trifluoromethoxy)-benzyloxy]-3,5-diiodobenzoic acid | 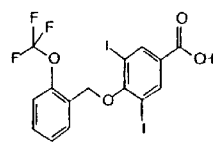 |
| 4-(10-carboxy-decyloxy)-3,5-diiodobenzoic acid | 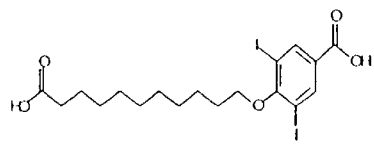 |
| 4-(4-tert-butyl-benzyloxy)-3,5-dichlorobenzoic acid | 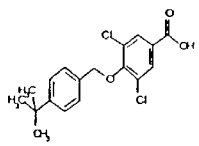 |
| 4-(2-phenyl-benzyloxy)-3,5-dibromobenzoic acid | 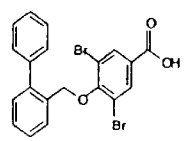 |
| {4-[(4-hydroxy-3,5-diiodophenyl)-oxo-acetyl]-2,6-diiodophenoxy}-acetic acid benzyl ester | 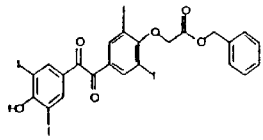 |
| {4-[(4-hydroxy-3,5-diiodophenyl)-oxo-acetyl]-2,6-diiodophenoxy}-acetic acid | 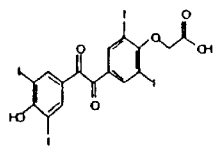 |
| 4-(2-phenyl)benzyloxy-3,5-dichlorobenzoic acid | 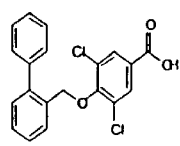 |

FIG. 1G

| NAME | STRUCTURE |
|---|---|
| 4-hydroxy-3,5-diiodobenzoic acid 2-(trimethylsilyl)ethoxymethoxy ester | 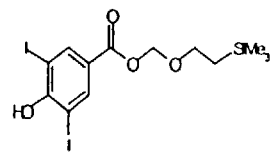 |
| 4-[(1',1',4'4'-tetra-methyl)-cyclohexyl-2',3'-(2-ethyl)-benzoyl-methoxy]-3,5-diiodobenzoic acid | 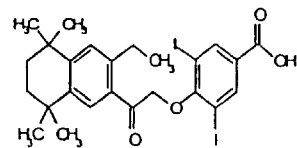 |
| 4-hexadecyloxy-3,5-diiodobenzoic acid | 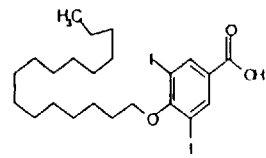 |
| [4-(4-hydroxy-3,5-diiodo-benzenesulfonyl)-2,6-diiodo-phenoxy]-acetic acid benzyl ester | 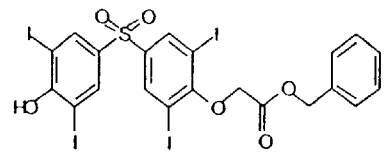 |
| [4-(4-hydroxy-3,5-diiodo-benzenesulfonyl)-2,6-diiodo-phenoxy]-acetic acid phenyl ester | 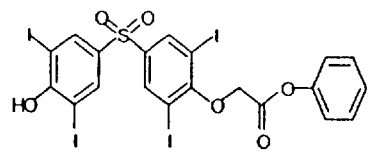 |
| 4-[3,5-diiodo-4-(3-iodobenzyloxy)-benzenesulfonyl]-2,6-diiodo-phenol | 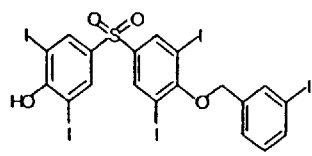 |
| 4-hydroxy-3,5-diiodobenzoic acid phenoxycarbonylmethyl ester | 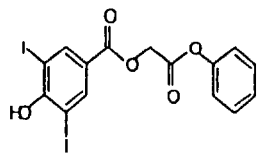 |

FIG. 1H

| NAME | STRUCTURE |
|------|-----------|
| 4-hydroxy-3,5-diiodobenzoic acid [4-chloro-2-(2-chloro-benzoyl)-phenylcarbamoyl]-methyl ester | 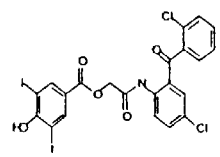 |
| [3,5-diiodo-4-(3-iodo-benzyloxy)-phenyl]-(4-hydroxy-3,5-diiodophenyl)-methanone | 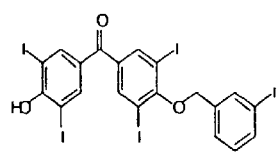 |
| [4-(4-hydroxy-3,5-diiodo-benzoyl)-2,6-diiodophenoxy]-acetic acid phenyl ester | 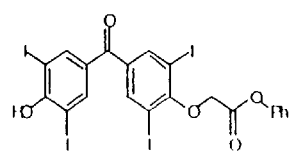 |
| 1-[3,5-diiodo-4-(3-iodo-benzyloxy)-phenyl]-2-(4-hydroxy-3,5-diiodophenyl)-ethane-1,2-dione | 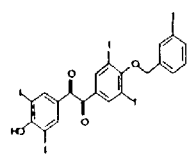 |
| {4-[(4-hydroxy-3,5-diiodophenyl)-oxo-acetyl]-2,6-diiodo-phenoxy}-acetic acid phenyl ester | 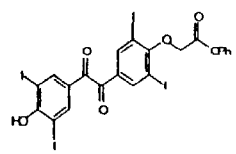 |
| carbonic acid benzyl ester 4-(4-hydroxy-3,5-diiodo-benzoyl)-2,6-diiodo-phenyl ester | 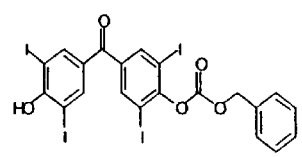 |
| 4-hydroxy-3,5-diiodo-benzoic acid 3-benzyloxybenzyl ester | 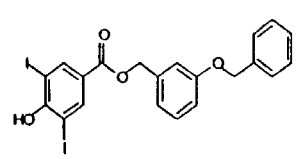 |

FIG. 1I

| NAME | STRUCTURE |
|---|---|
| [4-(9H-fluoren-9-yloxy)-3,5-diiodo-phenyl]-(4-hydroxy-3,5-diiodo-phenyl)-methanone | 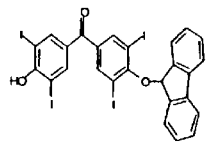 |
| 3-[3,5-diiodo-4-(3-iodo-benzyloxy)-phenyl]-3-(4-hydroxy-3,5-diiodo-phenyl)-3H-isobenzofuran-1-one | 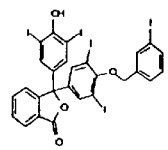 |
| [4-(4-hydroxy-3,5-diiodo-benzenesulfonyl)-2,6-diiodo-phenoxy]-acetic acid | 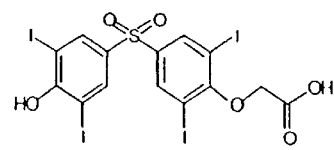 |
| 4-hydroxy-3,5-diiodo-benzoic acid 2-(4-methoxy-phenyl)-2-oxo-ethyl ester | 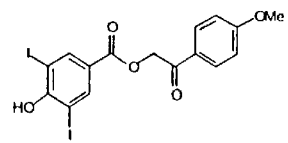 |
| 2-{2-[4-(4-hydroxy-3,5-diiodo-benzoyl)-2,6-diiodo-phenoxymethyl]-phenyl}-isoindole-1,3-dione | 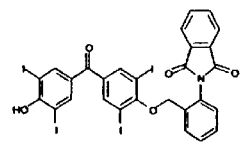 |
| 4-benzyloxycarbonyloxy-3,5-diiodo-benzoic acid | 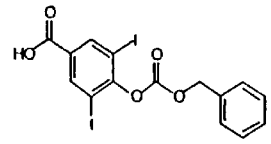 |
| 3,5-dibromo-4-hydroxy-benzoic acid 4-tbutyl-benzyl ester | 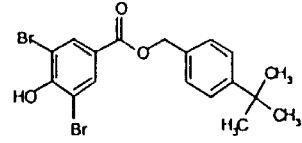 |
| 4-[2-(2,3-dihydro-benzo[1,4]dioxin-6-yl)-2-oxo-ethoxy]-3,5-diiodo-benzoic acid | 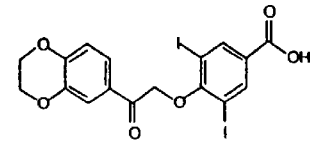 |

FIG. 1J

| NAME | STRUCTURE |
|---|---|
| 4-(oxane-2-methoxy)-3,5-diiodo-benzoic acid | 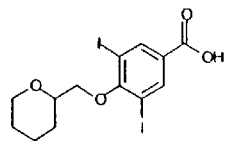 |
| 4-hydroxy-3,5-diiodo-benzoic acid 2-(1,3-dioxo-1,3-dihydro-isoindol-2-yl)-benzyl ester | 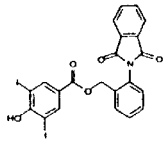 |
| 3,5-diiodo-4-hydroxy-N-phenylethyl-benzamide | 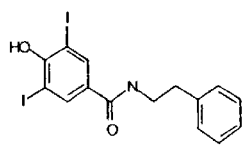 |
| 4-benzyl-2,6-diiodo-phenol | 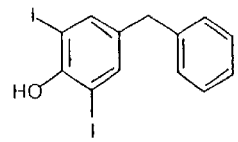 |
| 4-but-2-enyloxy-3,5-diiodo-benzoic acid | 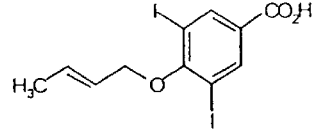 |
| acetic acid 4-[1-(4-hydroxy-3,5-diiodo-phenyl)-3-oxo-1,3-dihydro-isobenzofuran-1-yl]-2,6-diiodo-phenyl ester | 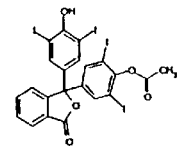 |
| 2,6-diiodo-4-(1-methyl-1-phenyl-ethyl)-phenol | 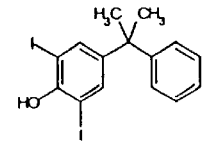 |
| 4-(3,5-diiodo-4-methoxy-benzenesulfonyl)-2,6-diiodo-phenol | 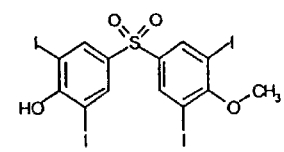 |

FIG. 1K

| NAME | STRUCTURE |
|---|---|
| 4-[4-(biphenyl-3-ylmethoxy)-3,5-diiodo-benzenesulfonyl]-2,6-diiodo-phenol | 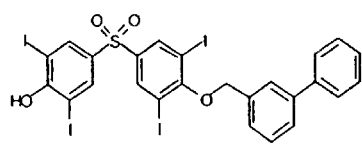 |
| (3,5-diiodo-4-methoxy-phenyl)-(4-hydroxy-3,5-diiodo-phenyl)-methanone | 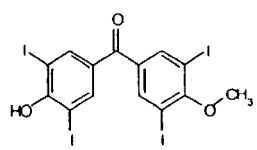 |
| (4-hydroxy-3,5-diiodo-phenyl)-morphenoxylin-4-yl-methanone | 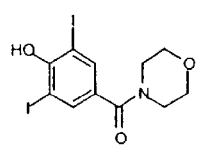 |
| [4-(biphenyl-3-ylmethoxy)-3,5-diiodo-phenyl]-(4-hydroxy-3,5-diiodo-phenyl)-methanone | 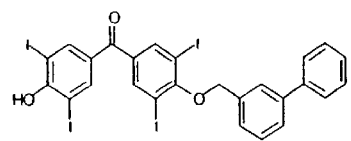 |
| 4-hydroxy-3,5-diiodobenzoic acid cyclohexylmethyl ester | 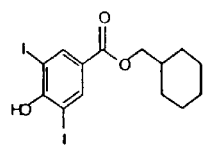 |
| 3-(3,5-diiodo-4-methoxyphenyl)-3-(4-hydroxy-3,5-diiodophenyl)-3H-isobenzofuran-1-one | 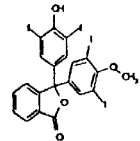 |
| (2-fluorophenyl)-(4-hydroxy-3,5-diiodophenyl)-methanone | 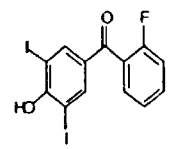 |
| 1-(4-hydroxy-3,5-diiodophenyl)-nonan-1-one | 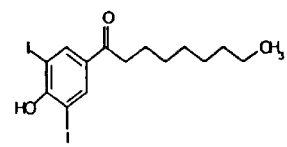 |

FIG. 1L

| NAME | STRUCTURE |
|---|---|
| 1-(4-hydroxy-3,5-diiodophenyl)-hexan-1-one | 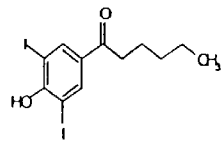 |
| 4-(2-cyclohexylethoxy)-3,5-diiodobenzoic acid | 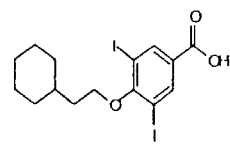 |
| (2,4-dimethoxyphenyl)-(4-hydroxy-3,5-diiodophenyl)-methanone | 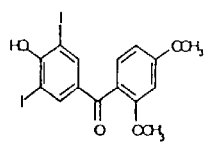 |
| 4'-hydroxy-3',5'-diiodo-biphenyl-4-carbonitrile | 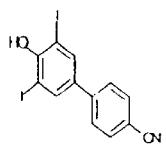 |
| 4-hydroxy-3,5-diiodobenzoic acid 4-(N-benzyl-N-ethyl-carbamoyl)-2,6-diiodophenyl ester | 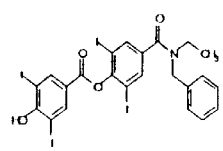 |
| 2,6-diiodo-[4-(1-benzyl)-tetrazolyl]-phenol | 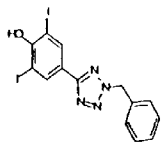 |
| 3-(4-hydroxy-3,5-diiodophenyl)-acrylic acid methyl ester | 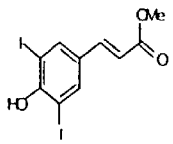 |
| 4-hydroxy-3,5-diiodobenzoic acid benzyl ester | 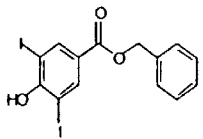 |
| 4-hydroxy-3,5-diiodobenzoic acid 3-(2-oxo-2-phenylethoxycarbonyl)-allyl ester | 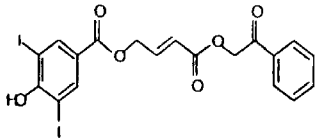 |

FIG. 1M

| NAME | STRUCTURE |
|---|---|
| 4-hydroxy-3,5-diiodobenzoic acid 1-methylhexyl ester | 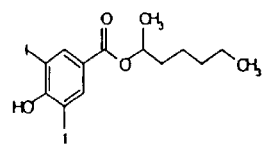 |
| 4-hydroxy-3,5-diiodobenzoic acid heptyl ester | 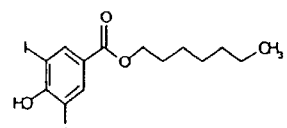 |
| 2,6-diiodo-4-octyl-phenol | 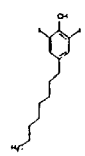 |
| 4-hydroxy-3,5-diiodobenzoic acid 2,4,4-trimethylpentyl ester | 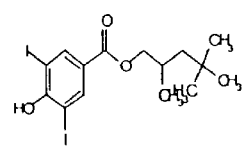 |
| 3-[3,5-diiodo-4-(2-iodobenzyloxy)-phenyl]-propionic acid | 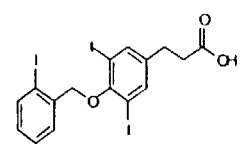 |
| 2,6-dichloro-4-phenyl-ethynyl-phenol | 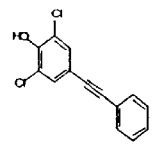 |
| 3-(4-hydroxy-3,5-diI-benzylidene)-1,3-dihydro-indol-2-one | 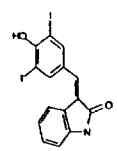 |
| 2-(4-tert-butyl)-benzyloxy-3,5-diiodobenzoic acid | 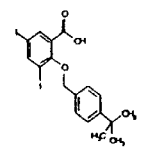 |
| 1-(4-hydroxy-3,5-diiodophenyl)-butan-1-one | 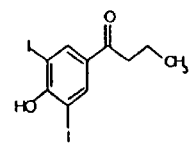 |
| 4-[2-(3,4-dihydro-2H-benzo[b][1,4]dioxepin-7-yl)-2-oxo-ethoxy]-3,5-diiodobenzoic acid | 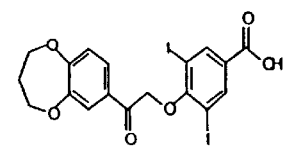 |

FIG. 1N

| NAME | STRUCTURE |
|---|---|
| 4-[2-(4-bromophenyl)-2-oxo-ethoxy]-3,5-diiodobenzoic acid | 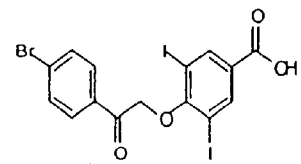 |
| 2,6-diiodo-4-(4-nitro)-phenyl-phenol | 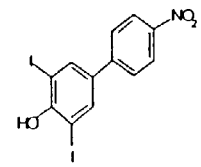 |
| 4-(1-hydroxynonyl)-2,6-diiodo-phenol | 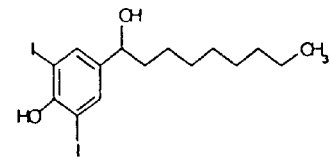 |
| 6-(3-iodobenzyloxy)-2,5,7,8-tetramethyl-chroman-2-carboxylic acid | 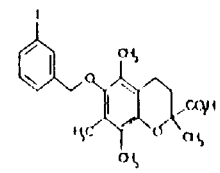 |
| 6-(2-iodobenzyloxy)-2,5,7,8-tetramethyl-chroman-2-carboxylic acid | 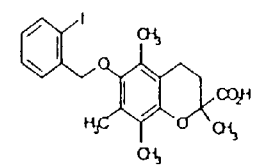 |
| 1-(3,5-diiodo-4-hydroxy)-phenyl-pentan-1-one | 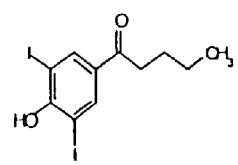 |
| N,N-dibenzyl-4-hydroxy-3,5-diiodo-benzamide | 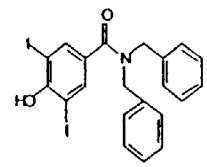 |
FIG. 10

| NAME | STRUCTURE |
|---|---|
| L THYROXINE | 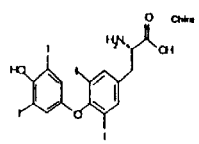 |
| 3,3',5,5'-TETRAIODOTHYRO-PROPIONIC ACID | 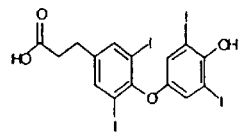 |
| L-3,3',5'-TRIIODOTHYRONINE | 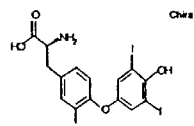 |
| 3,5-DIIODOTHYROPROPIONIC ACID | 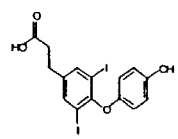 |
| 3,3',5-TRIIODOTHYROPROPIONIC ACID | 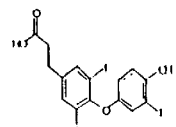 |
| 3,3',5-TRIIODOTHYROACETIC ACID | 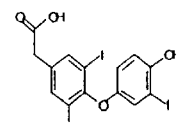 |
| 3,3',5,5'-TETRAIODOTHYRO-ACETIC ACID | 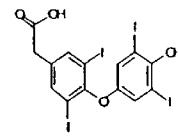 |
| 1-(2-(BR-NAPHTHALEN-YLOXY)-5-chloro-phenyl)-DI-ME-(1,3,5)TRIAZINE-DIAMINE, HYDROCHLORIDE | 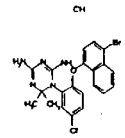 |
| 1,3,5(10)-ESTRATRIEN-2,4-DINITRO-3,17BETA-DIOL | 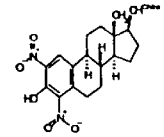 |
| 4-PHENOXYPHENOL | 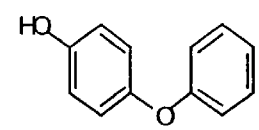 |
| D-THYROXINE | 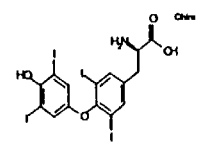 |
FIG. 2A

| NAME | STRUCTURE |
|---|---|
| N,O-DI-(2,4-DINITROPHENYL)-L-TYROSINE | 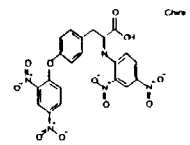 |
| 3,5,3',5'-TETRAIODOTHYROFORMIC ACID | 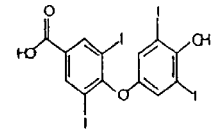 |
| 4-(4-(4-CHLORO-BENZENESULFONYL)-PHENOXY)-BENZOIC ACID | 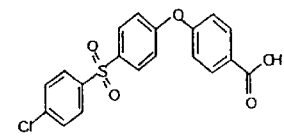 |
| 4-(4-(TRIFLUOROMETHYL)PHENOXY)PHENOL | 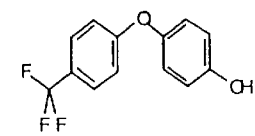 |
| 3-NITRO-6-(4-TERT-BUTYLPHENOXY)-3-PHENYLACRYLIC ACID | 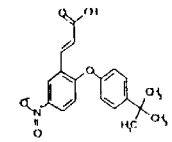 |
| 5-NITRO-2-(4-(1,1,3,3-TETRAMETHYLBUTYL)PHENOXY)BENZENESULFONIC ACID | 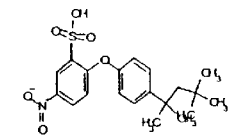 |
| FMOC-P-BENZOYL-PHENYLALANINE | 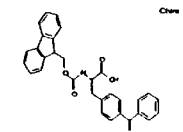 |
| O-(3-CARBOXYBENZYL)-3,4-DICHLORO ACETOPHENONE OXIME | 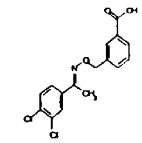 |
| 6-(4-BENZYL-PHENYL)-HEXANOIC ACID | 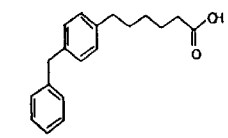 |
| 3-NITRO-9H-XANTHEN-9-ONE | 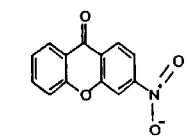 |

FIG. 2B

| NAME | STRUCTURE |
|---|---|
| 5-CHLORO-2-(4-CHLORO-2-(3,4-DICHLOROPHENYLUREIDO)-PHENOXY)-BENZENESULFONIC ACID | 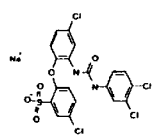 |
| FMOC-P-BENZOYL-D-PHENYLALANINE | 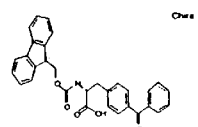 |
| 7-ANILINO-1-NAPHTHOL-3-SULFONIC ACID | 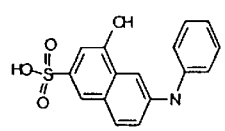 |
| 4-(4-ANILINOPHENYLAZO)BENZENESULFONIC ACID | 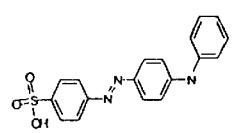 |
| 7-ANILINO-4-HYDROXY-2-NAPHTHALENESULFONIC ACID | 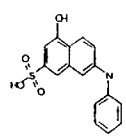 |
| DIPHENYLPHOSPHINOBENZENE-3-SULFONIC ACID SODIUM SALT | 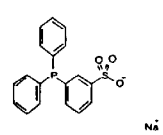 |
| 2-[4-[(4-CHLOROPHENYL)THIO]-3-NITROBENZOYL]BENZOIC ACID | 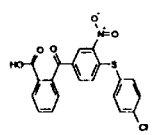 |
| 5-CHLORO-2-(2-HYDROXYBENZYLAMINO)BENZOPHENONE | 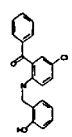 |
| FMOC-4-FLUOROPHENYLALANINE | 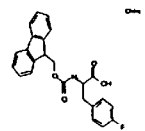 |
| FMOC-2,6-DICHLORO-BENZYLTYROSINE | 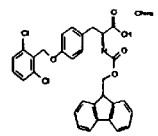 |

FIG. 2C

| NAME | STRUCTURE |
|---|---|
| N-FMOC-4-CHLORO-L-PHENYLALANINE | 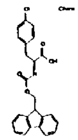 |
| FMOC-BIPHENYLALANINE | 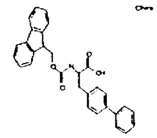 |
| FMOC-P-PHENYL-D-PHENYLALANINE | 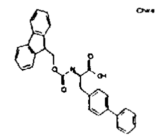 |
| FMOC-D-1-NAPHTHYLALANINE | 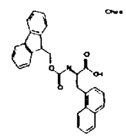 |
| FMOC-(3,5-DIIODO)-D-TYROSINE | 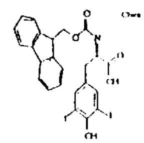 |
| FMOC-N-METHYL-O-BENZYL-TYROSINE | |
| FMOC-4-BROMO-D-PHENYLALANINE | 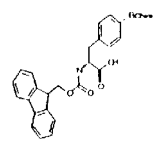 |
| FMOC-3,4-DICHLORO-D-PHENYLALANINE | 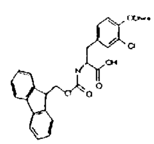 |
| FMOC-3,4-DICHLORO-L-PHENYLALANINE | 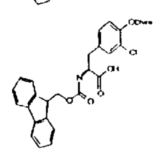 |
| FMOC-3-CHLORO-PHENYLALANINE | 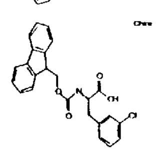 |
| FMOC-L-3-(TRIFLUOROMETHYL)PHENYLALANINE | 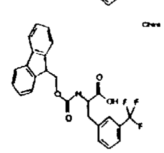 |
| FMOC-NAPHTHYLALANINE | 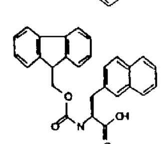 |

| NAME | STRUCTURE |
|---|---|
| FMOC-4-TERT-BUTHYLTHIO-PHENYLALANINE | 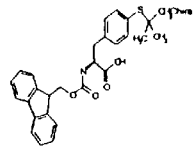 |
| FMOC-4-ISOPROPYL-PHENYLALANINE | 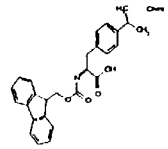 |
| FMOC-L-3-BENZOTHIENYLALANINE | 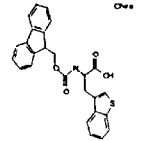 |
| FMOC-D-3-BENZOTHIENYLALANINE | 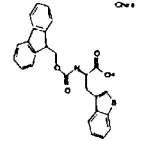 |
| FMOC-L-2-NAPHTHYLALANINE | 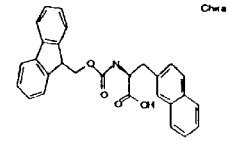 |
| N,S-BIS-FMOC-GLUTATHIONE | 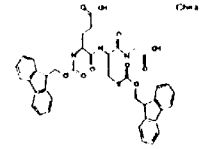 |
| 1-HEXADECANESULFONIC (METHYL-SULFO-(TOLYLOXYPHENYL)QUINOLYLIDENE)HYDRAZIDE | 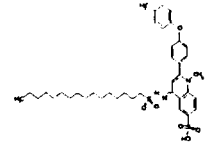 |
| CHLORO-HYDROXY-PHENYL-AZO-OCTADECAN-AMIDO-OXO-PYRAZOLINYL-PHENOXY-BENZENE-SULFONIC ACID | 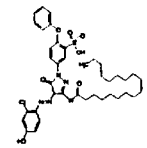 |
| 1-(3-SULFO-4-PHENOXY)-PHENYL-3-HEPTADECYL-PYRAZOLINE-5-ONE | 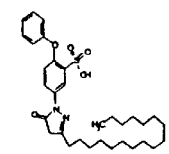 |

FIG. 2E

| NAME | STRUCTURE |
|---|---|
| 1-(3-SULFO-4-PHENOXY)-PHENYL-3-HEPTADECYL-CARBONYL-AMINO-PYRAZOLINE-5-ONE | 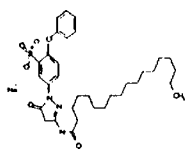 |
| 5-[4,5-DIHYDRO-5-OXO-3-[(1-OXOOCTADECYL)AMINO]-1H-PYRAZOL-1-YL]-2-PHENOXY-BENZENE | 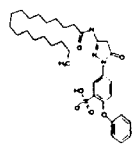 |
| PHTHALIC ACID MONO-(BIPHENYL-4-YL-PHENYL-METHYL) ESTER | 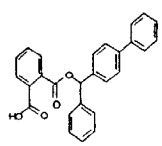 |
| SODIUM DECYL DIPHENYL ETHER DISULFONATE | 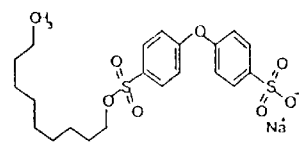 |
| 2-HO-5-(4'-HO-BIPHENYL-4-YLAZO)-BENZOIC ACID, SODIUM SALT | 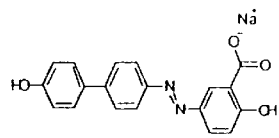 |
| (S)-N-FMOC-STYRYLALANINE | 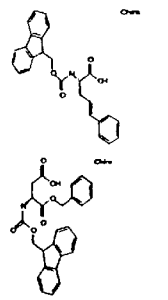 |
| FMOC-O-BENZYL-ASPARTIC ACID | 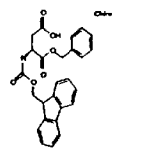 |
| FMOC-S-(4-METHYLBENZYL)-D-CYSTEINE | 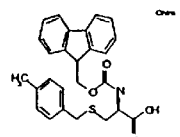 |
| (S)-N-FMOC-2-(5-BROMOTHIENYL)-ALANINE | 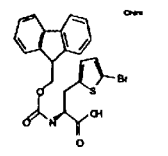 |

FIG. 2F

| NAME | STRUCTURE |
|---|---|
| 2-[[(9H-FLUOREN-9-YLMETHOXY)CARBONYL]AMINO]-5-[[[(2,2,5,7,8-PENTA-METHYL-3,4-DIHYDRO-2H-CROMAN-6-YL-SULFONYL)-AMINO]-IMINO]-AMINO]-PENTANOIC ACID | 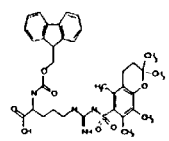 |
| 4,5,9,10-TETRAHYDRO-PYRENE-2,7-DIOL | 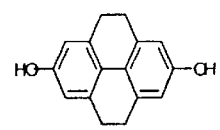 |
| SODIUM DODECYL DIPHENYL ETHER DISULFONATE | 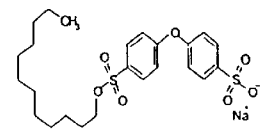 |
| FMOC-(R)-3-AMINO-5-PHENYL-PENTANOIC ACID | 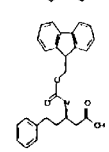 |
| FMOC-(S)-3-AMINO-5-PHENYL-PENTANOIC ACID | 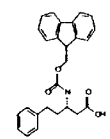 |
| FMOC-(S)-3-AMINO-4-(3-BENZOTHIENYL)-BUTYRIC ACID | 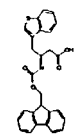 |
| FMOC-(R)-3-AMINO-4-(3-BENZOTHIENYL)-BUTYRIC ACID | 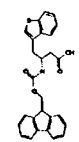 |
| FMOC-(R)-3-AMINO-(6-PHENYL)-5-HEXENOIC ACID | 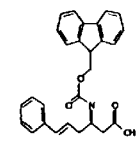 |
| FMOC-L-4-TERT-BUTYL-PHENYLALANINE | 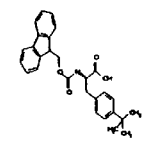 |
| FMOC-D-4-TERT-BUTYL-PHENYLALANINE | 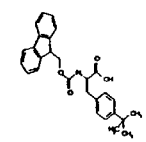 |

FIG. 2G

| NAME | STRUCTURE |
|---|---|
| BOC-3,5-DIIODO-O-(3'-BROMOBENZYL)-TYROSINE | 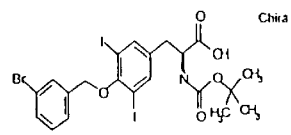 |
| BOC-3,5-DIIODO-O-(2',6'-DICHLOROBENZYL)-TYROSINE | 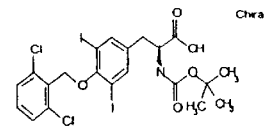 |
| FMOC-O-(2,6-DICHLOROBENZYL)-TYROSINE | 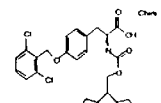 |
| FMOC-(2-CHLOROBENZYLOXYCARBONYL)-LYSINE | 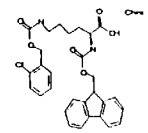 |
| 3,4,5-TRIIODOBENZOIC ACID | 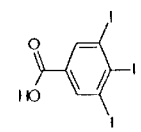 |
| 2-(2,4,6-TRIIODOPHENOXY)-ETHANESULFONIC ACID | 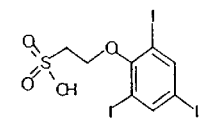 |
| 2-PHENYL-2-(2,4,6-TRIIODOPHENOXY)ACETIC ACID | 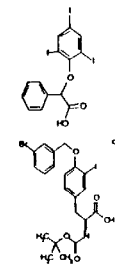 |
| BOC-3-IODO-O-(3-BROMOBENZYL)-TYROSINE | 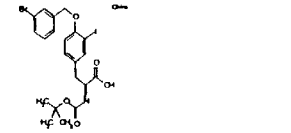 |
| BOC-3,5-DIBROMO-O-BENZYLTYROSINE | 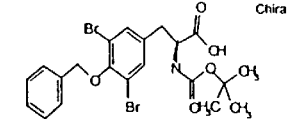 |
| 2-TOSYL-AMINO-5-(3-CARBOXY-4-TOSYL-AMINO-BENZYL)-BENZOIC ACID | 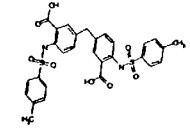 |
| 5-bis-2-N-(1-naphenylthalamide) benzoic acid | 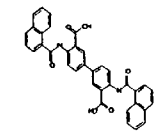 |

FIG. 2H

| NAME | STRUCTURE |
|---|---|
| 2-(3-ETHYNYL-PHENYL)-1,3-DIOXO-2,3-DIHYDRO-1H-5-(4-CARBOXY)-BENZOYL-ISOINDOLE | 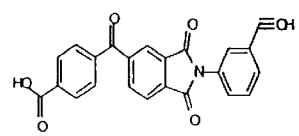 |
| 2-[4-(amido-benz-2-oic acid)]-6-methyl-benzthiazole | 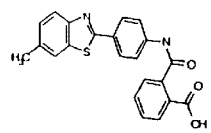 |
| 2.5-DICHLORO-PHENYL-THIO-METHY-LBENZOIC ACID | 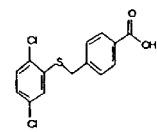 |
| (3Z,6Z)-3-(4-(3-dimethylaminopropoxy)benzylidene)-6-(4-nitrobenzylidene)- 2,5-piperazinone | 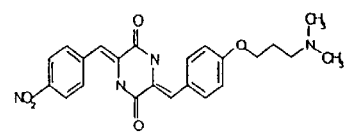 |
| (3Z,6Z)-3-(4-(3-dimethylaminopropoxy)benzylidene)-6-(4-nitrobenzylidene)- 2,5-piperazinone | 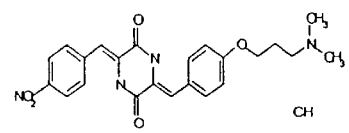 |
| (4-hydroxy-3-iodo-5-nitro-phenyl)-phenyl-methanone | 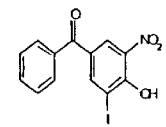 |
| 3,5-diiodo-4-(3-iodo-benzyloxy)- benzoic acid | 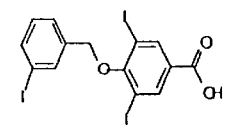 |
| 3,5-diiodo-4-(4-iodo-benzyloxy)- benzoic acid | 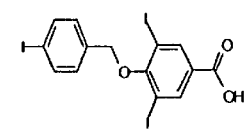 |
| 4-benzyloxy-3,5-diiodo-benzoic acid | 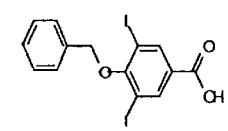 |
| 3,5-diiodo-4-(2-bromo-benzyloxy)- benzoic acid | 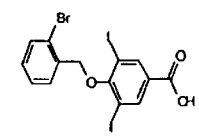 |
| 3,5-diiodo-4-(3-bromo-benzyloxy)- benzoic acid | 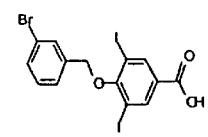 |

FIG. 21

| NAME | STRUCTURE |
|---|---|
| 3,5-diiodo-4-(4-bromo-benzyloxy)- benzoic acid | 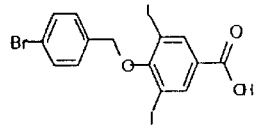 |
| 3,5-diiodo-4-(2-methyl-benzyloxy)- benzoic acid | 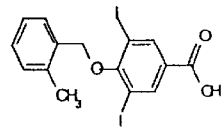 |
| 3,5-diiodo-4-(3-methyl-benzyloxy)- benzoic acid | 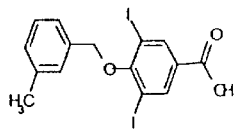 |
| 3,5-diiodo-4-(4-methyl-benzyloxy)- benzoic acid | 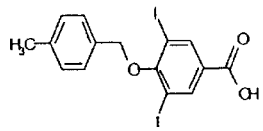 |
| 4-(4-tert-butyl-benzyloxy)-3,5- diiodo-benzoic acid | 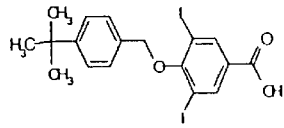 |
| 3,5-diiodo-4-(naphthalen-2-ylmethoxy)-benzoic acid | 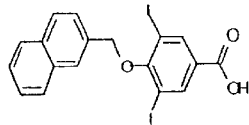 |
| 4-(biphenyl-2-ylmethoxy)-3,5-diiodo- benzoic acid | 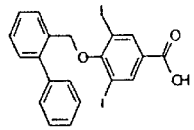 |
| 3,5-diiodo-4-(3-methoxy-benzyloxy)- benzoic acid | 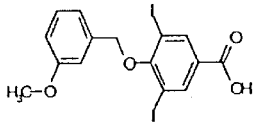 |
| 3,5-diiodo-4-(3-trifluoromethyl-benzyloxy)-benzoic acid | 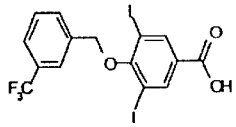 |
| 3,5-diiodo-4-(3-trifluoromethoxy-benzyloxy)-benzoic acid | 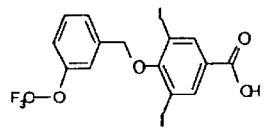 |
| 4-(3-fluoro-benzyloxy)-3,5-diiodo-benzoic acid | 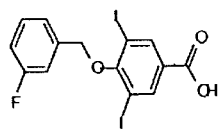 |

FIG. 2J

| NAME | STRUCTURE |
|---|---|
| 3,5-diiodo-4-pentafluorophenylmethoxy- benzoic acid | 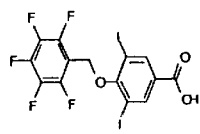 |
| 3,5-dibromo-4-(3-iodo-benzyloxy)-benzoic acid | 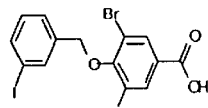 |
| 3,5-dichloro-4-(3-iodo-benzyloxy)-benzoic acid | 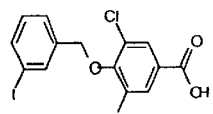 |
| 3-(4-benzyloxy-3,5-diiodo-phenyl)-propionic acid benzyl ester | 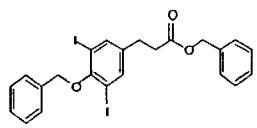 |
| 3-[3,5-diiodo-4-(3-iodo-benzyloxy)-phenyl]-propionic acid | 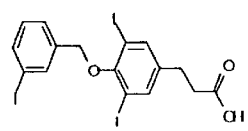 |
| 3-[3,5-diiodo-4-(4-iodo-benzyloxy)-phenyl]-propionic acid | 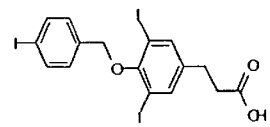 |
| 3-(4-benzyloxy-3,5-diiodo-phenyl)-propionic acid | 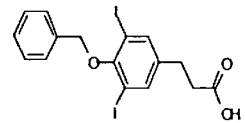 |
| 3-[4-(3-bromo-benzyloxy)-3,5-diiodo-phenyl]-propionic acid | 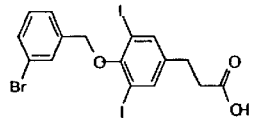 |
| 3-[4-(4-bromo-benzyloxy)-3,5-diiodo-phenyl]-propionic acid | 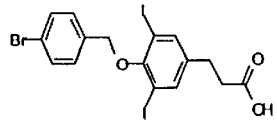 |
| 3,5-dibromo-4-(4-tert-butyl-benzyloxy)-benzoic acid | 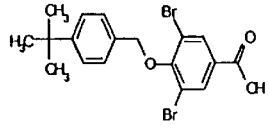 |
| [3,5-diiodo-4-(3-iodo-benzyloxy)-phenyl]-acetic acid | 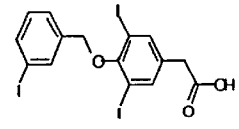 |
| [3,5-diiodo-4-(4-iodo-benzyloxy)-phenyl]-acetic acid | 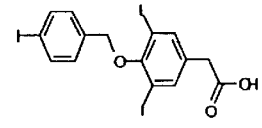 |

FIG. 2K

| NAME | STRUCTURE |
|---|---|
| (4-benzyloxy-3,5-diiodo-phenyl)-acetic acid | 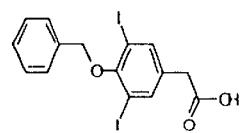 |
| [4-(3-bromo-benzyloxy)-3,5-diiodo-phenyl]-acetic acid | 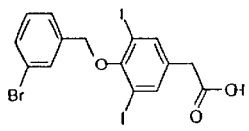 |
| 4-(2-nitro-benzyloxy)-3,5-diiodo-benzoic acid | 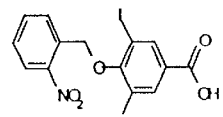 |
| 4-(3-nitro-benzyloxy)-3,5-diiodo-benzoic acid | 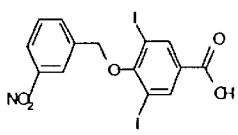 |
| 4-(4-nitro-benzyloxy)-3,5-diiodo-benzoic acid | 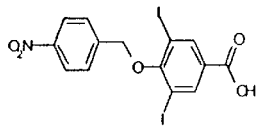 |
| 4-(2-cyano-benzyloxy)-3,5-diiodo-benzoic acid | 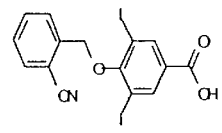 |
| 4-(3-cyano-benzyloxy)-3,5-diiodo-benzoic acid | 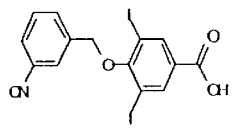 |
| 4-(4-cyano-benzyloxy)-3,5-diiodo-benzoic acid | 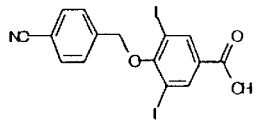 |
| (4-hydroxy-3,5-diiodophenyl)-phenyl-methanone | 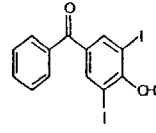 |
| (4-benzoyl-2,6-diiodophenoxy)-acetic acid | 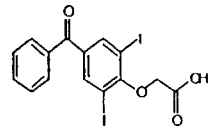 |
| 4-hydroxy-3,5-diiodobenzoic acid 2-iodobenzyl ester | 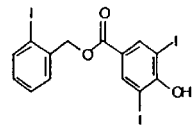 |
| 2-acetylamino-3-[3,5-diiodo-4-(3-iodobenzyloxy)-phenyl]-propionic acid | 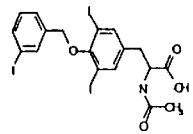 |

FIG. 2L

| NAME | STRUCTURE |
|---|---|
| bis-(4-hydroxy-3,5-diiodophenyl)-methanone | 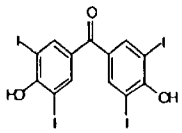 |
| 4-(2-fluorobenzyloxy)-3,5-diiodobenzoic acid | 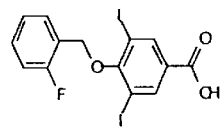 |
| 4-(4-fluorobenzyloxy)-3,5-diiodobenzoic acid | 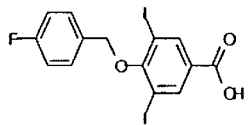 |
| 4-(2-chloro-benzyloxy)-3,5-diiodobenzoic acid | 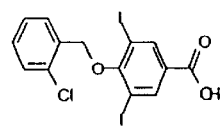 |
| 4-(3-chloro-benzyloxy)-3,5-diiodobenzoic acid | 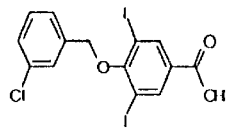 |
| [4-(4-hydroxy-3,5-diiodo-benzoyl)-2,6-diiodo-phenoxy]-acetic acid benzyl ester | 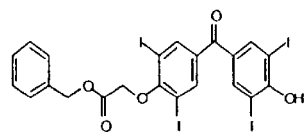 |
| 4-(4-chloro-benzyloxy)-3,5-diiodobenzoic acid | 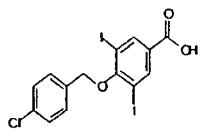 |
| [4-[(6,7-dihydro-5,5,8,8-tetramethyl)naphthyl-2-methoxy]-3,5-diiodobenzoic acid | 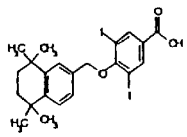 |
| 4-(1,6-dichloro-benzyloxy)-3,5-diiodobenzoic acid | 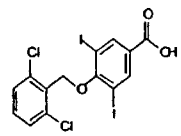 |
| 4-(1,6-difluoro-benzyloxy)-3,5-diiodobenzoic acid | 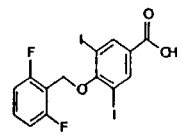 |
| 4-[4-(trifluoromethoxy)-benzyloxy]-3,5-diiodobenzoic acid | 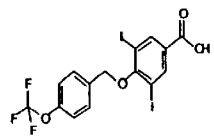 |

FIG. 2M

| NAME | STRUCTURE |
|---|---|
| 4-[2-(trifluoromethyl)-benzyloxy]-3,5-diiodobenzoic acid | 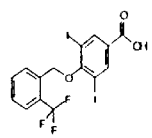 |
| 4-[4-(trifluoromethyl)-benzyloxy]-3,5-diiodobenzoic acid | 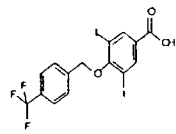 |
| 4-[(2-fluoro-4-bromo)benzyloxy]-3,5-diiodobenzoic acid | 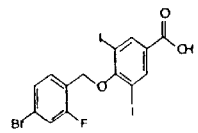 |
| 4-(2-iodo)benzyloxy-3,5-diiodobenzoic acid | 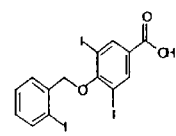 |
| 4-(3-benzoyl)benzyloxy-3,5-diiodobenzoic acid | 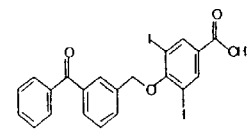 |
| 4-(3,5-dimethoxy)benzyloxy-3,5-diiodobenzoic acid | 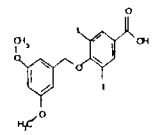 |
| 4-[(4-hydroxy-3,5-diiodo)-benzoyl]-2,6-diiodo-phenoxy-acetic acid | 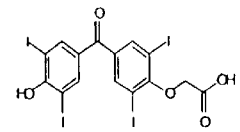 |
| 4-(3-methylnaphthyl-2-methoxy)-3,5-diiodobenzoic acid | 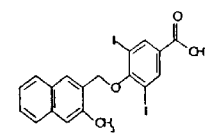 |
| 4-[N-[(2-benzoyl)phenyl]-MeOamidyl]-3,5-diiodobenzoic acid | 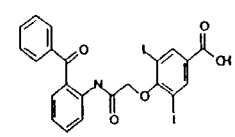 |
| 4-[4-(trifluoromethyl)thio]-benzyloxy-3,5-diiodobenzoic acid | 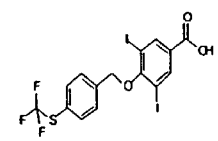 |
| 4-[2-(trifluoromethyl)thio]-benzyloxy-3,5-diiodobenzoic acid | 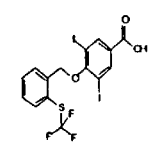 |

FIG. 2N

| NAME | STRUCTURE |
|---|---|
| 4-(adamantyl-1-acetyloxy)-3,5-diiodobenzoic acid | 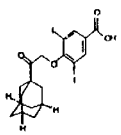 |
| 4-(4-chloro)benzyloxy-3,5-dichloro-benzoic acid | 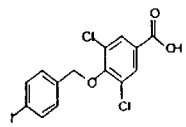 |
| 4-(naphthyl-2-methoxy)-3,5-dichloro-benzoic acid | 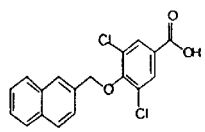 |
| 4-(4-iodo)benzyloxy-3,5-dibromobenzoic acid | 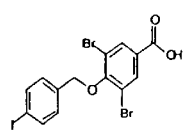 |
| 4-(naphthyl-2-methoxy)-3,5-dibromobenzoic acid | 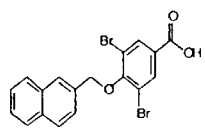 |
| 4(9H-fluoren-9-yloxy)-3,5-diiodobenzoic acid | 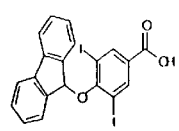 |
| 1,2-bis-(4-hydroxy-3,5-diiodo-phenyl)-ethane-1,2-dione | 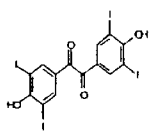 |
| (4-fluoro-phenyl)-(4-hydroxy-3,5-diiodo-phenyl)-methanone | 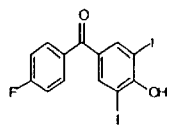 |
| 4-[3-(2-fluoro)phenylenoxy-benzyloxy]-3,5-diiodobenzoic acid | 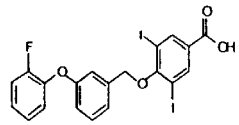 |
| 4-[2-(trifluoromethoxy)-benzyloxy]-3,5-diiodobenzoic acid | 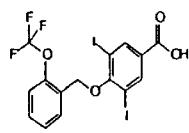 |
| 4-(10-carboxy-decyloxy)-3,5-diiodobenzoic acid | 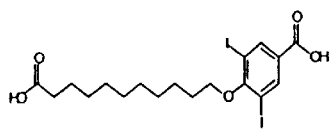 |
| 4-(4-tert-butyl-benzyloxy)-3,5-dichloro-benzoic acid | 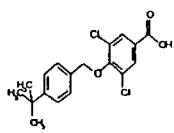 |

FIG. 20

| NAME | STRUCTURE |
|---|---|
| 4-(2-phenyl-benzyloxy)-3,5-dibromobenzoic acid | 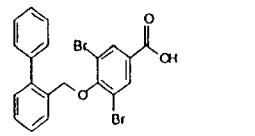 |
| {4-[(4-hydroxy-3,5-diiodo-phenyl)-oxo-acetyl]-2,6-diiodo-phenylenoxy}-acetic acid benzyl ester | 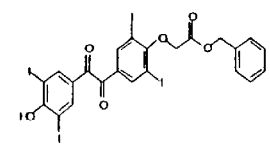 |
| {4-[(4-hydroxy-3,5-diiodo-phenyl)-oxo-acetyl]-2,6-diiodo-phenylenoxy}-acetic acid | 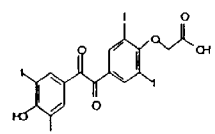 |
| 4-(2phenyl)benzyloxy-3,5-dichloro-benzoic acid | 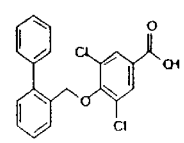 |
| 4-hydroxy-3,5-diiodobenzoic acid 2-trimethylsilylethoxymethoxy ester | 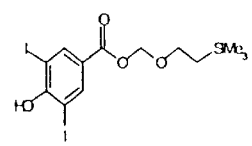 |
| 3,3',5,5'-tetraiodo-4,4'-sulfonyldiphenylenol | 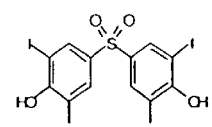 |
| 4-[(1',1',4',4'-tetramethyl)cychloroohexyl-2',3'-(2-ethyl)benzoylmethoxy]-3,5-diiodobenzoic acid | 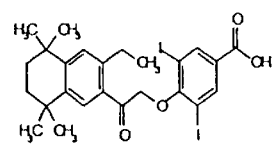 |
| 4-hexadecyloxy-3,5-diiodobenzoic acid | 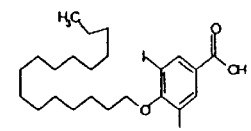 |
| [4-(4-hydroxy-3,5-diiodo-benzenesulfonyl)-2,6-diiodo-phenoxy]-acetic acid benzyl ester | 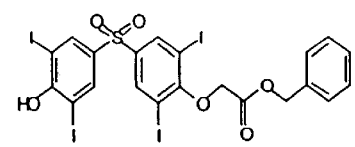 |

FIG. 2P

| NAME | STRUCTURE |
|---|---|
| [4-(4-hydroxy-3,5-diiodo-benzenesulfonyl)-2,6-diiodo-phenylenoxy]-acetic acid phenyl ester | 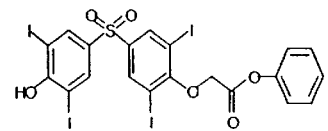 |
| 4-[3,5-diiodo-4-(3-iodo-benzyloxy)-benzenesulfonyl]-2,6-diiodo-phenylenol | 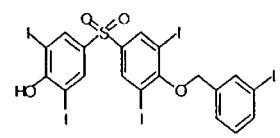 |
| 4-hydroxy-3,5-diiodobenzoic acid phenoxycarbonylmethyl ester | 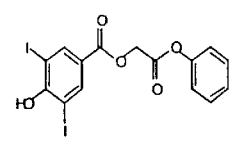 |
| 4-hydroxy-3,5-diiodobenzoic acid [4-chloro-2-(2-chloro-benzoyl)-phenylcarbamoyl]-methyl ester | 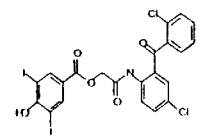 |
| [3,5-diiodo-4-(3-iodo-benzyloxy)-phenyl]-(4-hydroxy-3,5-diiodo-phenyl)-methanone | 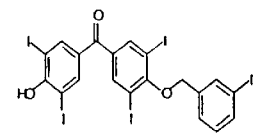 |
| [4-(4-hydroxy-3,5-diiodo-benzoyl)-2,6-diiodo-phenylenoxy]-acetic acid phenyl ester | 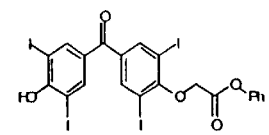 |
| 1-[3,5-diiodo-4-(3-iodo-benzyloxy)-phenyl]-2-(4-hydroxy-3,5-diiodo-phenyl)-ethane-1,2-dione | 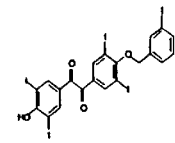 |
| {4-[(4-hydroxy-3,5-diiodo-phenyl)-oxo-acetyl]-2,6-diiodo-phenoxy}-acetic acid phenyl ester | 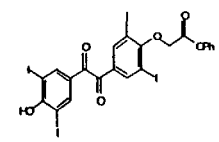 |

FIG. 2Q

| NAME | STRUCTURE |
|---|---|
| 3,3-bis-(4-hydroxy-3,5-diiodo-phenyl)-3H-isobenzofuran-1-one | 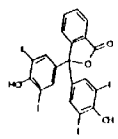 |
| carbonic acid benzyl ester 4-(4-hydroxy-3,5-diiodo-benzoyl)-2,6-diiodo-phenyl ester | 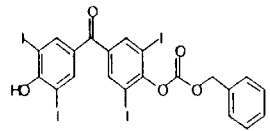 |
| 4-hydroxy-3,5-diiodobenzoic acid 3-benzyloxy-benzyl ester | 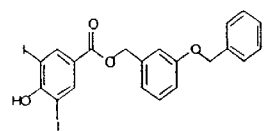 |
| [4-(9H-fluoren-9-yloxy)-3,5-diiodo-phenyl]-(4-hydroxy-3,5-diiodo-phenyl)-methanone | 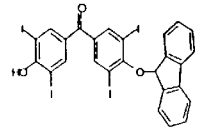 |
| 3-[3,5-diiodo-4-(3-iodo-benzyloxy)-phenyl]-3-(4-hydroxy-3,5-diiodo-phenyl)-3H-isobenzofuran-1-one | 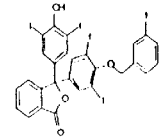 |
| [4-(4-hydroxy-3,5-diiodo-benzenesulfonyl)-2,6-diiodo-phenoxy]-acetic acid | 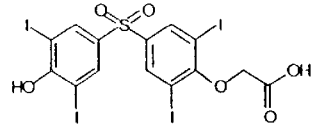 |
| 4-hydroxy-3,5-diiodo-benzoic acid 2-(4-methoxy-phenyl)-2-oxo-ethyl ester | 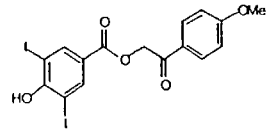 |
| 2-{2-[4-(4-hydroxy-3,5-diiodo-benzoyl)-2,6-diiodo-phenoxymethyl]-phenyl}-isoindole-1,3-dione | 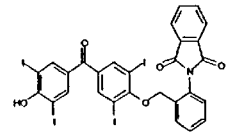 |
| 4-benzyloxycarbonyloxy-3,5-diiodo-benzoic acid | 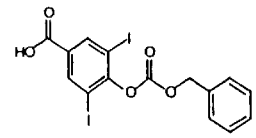 |

FIG. 2R

| NAME | STRUCTURE |
|---|---|
| 3,5-dibromo-4-hydroxy-benzoic acid 4-tbutyl-benzyl ester | 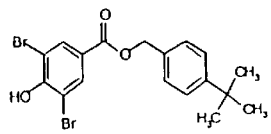 |
| 4-[2-(2,3-dihydro-benzo[1,4]dioxin-6-yl)-2-oxo-ethoxy]-3,5-diiodo-benzoic acid | 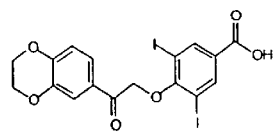 |
| 4-(oxane-2-methoxy)-3,5-diiodo-benzoic acid | 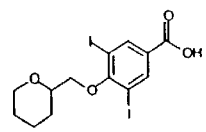 |
| 4-hydroxy-3,5-diiodo-benzoic acid 2-(1,3-dioxo-1,3-dihydro-isoindol-2-yl)-benzyl ester | 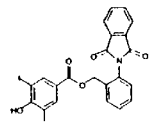 |
| 3,5-diiodo-4-hydroxy-N-phenylethyl-benzamide | 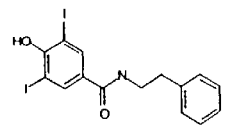 |
| 4-benzyl-2,6-diiodo-phenol | 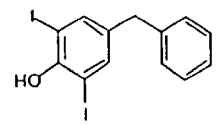 |
| 4-but-2-enyloxy-3,5-diiodo-benzoic acid | 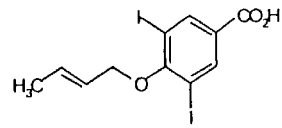 |
| acetic acid 4-[1-(4-hydroxy-3,5-diiodo-phenyl)-3-oxo-1,3-dihydro-isobenzofuran-1-yl]-2,6-diiodo-phenyl ester | 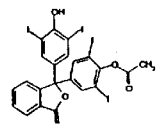 |
| 2,6-diiodo-4-(1-methyl-1-phenyl-ethyl)-phenol | 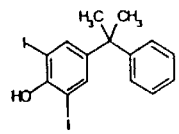 |

FIG. 2S

| NAME | STRUCTURE |
|---|---|
| 4-(3,5-diiodo-4-methoxy-benzenesulfonyl)-2,6-diiodo-phenol | 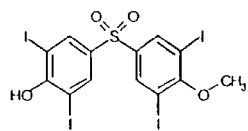 |
| 4-[4-(biphenyl-3-ylmethoxy)-3,5-diiodo-benzenesulfonyl]-2,6-diiodo-phenol | 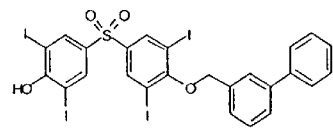 |
| (3,5-diiodo-4-methoxy-phenyl)-(4-hydroxy-3,5-diiodo-phenyl)-methanone | 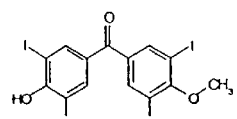 |
| (4-hydroxy-3,5-diiodo-phenyl)-morphenoxylin-4-yl-methanone | 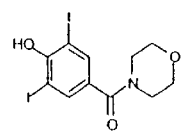 |
| [4-(biphenyl-3-ylmethoxy)-3,5-diiodo-phenyl]-(4-hydroxy-3,5-diiodo-phenyl)-methanone | 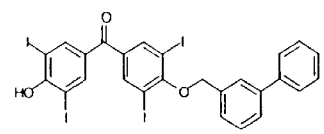 |
| 4-hydroxy-3,5-diiodobenzoic acid cyclohexylmethyl ester | 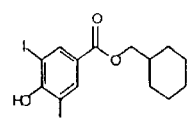 |
| 3-(3,5-diiodo-4-methoxyphenyl)-3-(4-hydroxy-3,5-diiodophenyl)-3H-isobenzofuran-1-one | 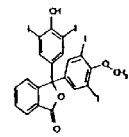 |
| (2-fluorophenyl)-(4-hydroxy-3,5-diiodophenyl)-methanone | 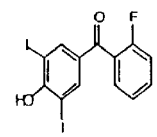 |
| 1-(4-hydroxy-3,5-diiodophenyl)-nonan-1-one | 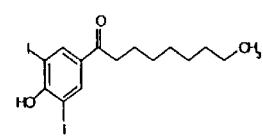 |

FIG. 2T

| NAME | STRUCTURE |
|---|---|
| 1-(4-hydroxy-3,5-diiodophenyl)-hexan-1-one | 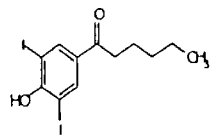 |
| 4-(2-cyclohexylethoxy)-3,5-diiodobenzoic acid | 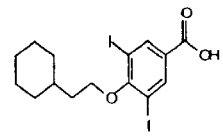 |
| (2,4-dimethoxyphenyl)-(4-hydroxy-3,5-diiodophenyl)-methanone | 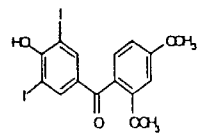 |
| 4'-hydroxy-3',5'-diiodo-biphenyl-4-carbonitrile | 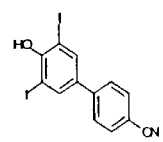 |
| 4-hdyroxy-3,5-diiodobenzoic acid n-butyl ester | 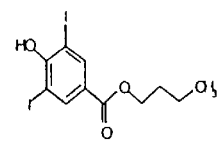 |
| 4-hydroxy-3,5-diiodobenzoic acid 4-(N-benzyl-N-ethyl-carbamoyl)-2,6-diiodophenyl ester | 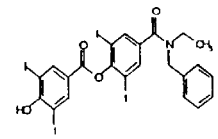 |
| 2,6-diiodo-[4-(1-benzyl)-tetrazolyl]-phenol | 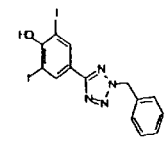 |
| 3-(4-hydroxy-3,5-diiodophenyl)-acrylic acid methyl ester | 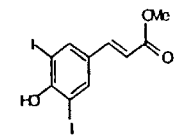 |
| 4-hydroxy-3,5-diiodobenzoic acid benzyl ester | 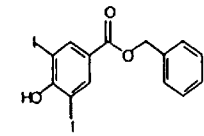 |
| 4-hydroxy-3,5-diiodobenzoic acid 3-(2-oxo-2-phenylethoxycarbonyl)-allyl ester | 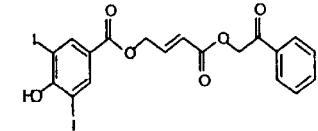 |

FIG. 2U

| NAME | STRUCTURE |
|---|---|
| 4-hydroxy-3,5-diiodobenzoic acid 1-methylhexyl ester | 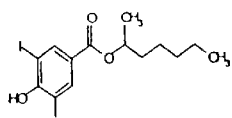 |
| 4-hydroxy-3,5-diiodobenzoic acid heptyl ester | 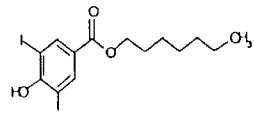 |
| 2,6-diiodo-4-octyl-phenol | 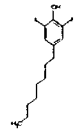 |
| 4-hydroxy-3,5-diiodobenzoic acid 2,4,4-trimethylpentyl ester | 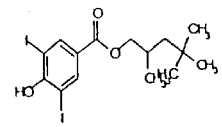 |
| 3-[3,5-diiodo-4-(2-iodobenzyloxy)-phenyl]-propionic acid | 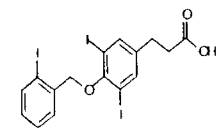 |
| 2,6-dichloro-4-phenyl-ethynyl-phenol | 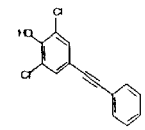 |
| 3-(4-hydroxy-3,5-diI-benzylidene)-1,3-dihydro-indol-2-one | 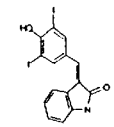 |
| 2-(4-tert-butyl)-benzyloxy-3,5-diiodobenzoic acid | 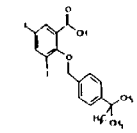 |
| 1-(4-hydroxy-3,5-diiodophenyl)-butan-1-one | 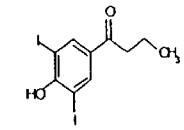 |
| 4-[2-(3,4-dihydro-2H-benzo[b][1,4]dioxepin-7-yl)-2-oxo-ethoxy]-3,5-diiodobenzoic acid | 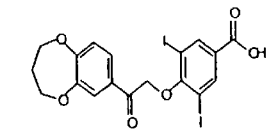 |
| 4-[2-(4-bromophenyl)-2-oxo-ethoxy]-3,5-diiodobenzoic acid | 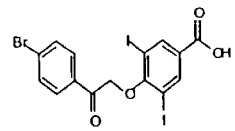 |

FIG. 2V

| NAME | STRUCTURE |
|---|---|
| 2,6-diiodo-4-(4-nitro)-phenyl-phenol | 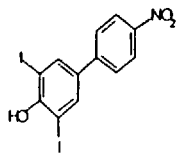 |
| 4-(1-hydroxynonyl)-2,6-diiodo-phenol | 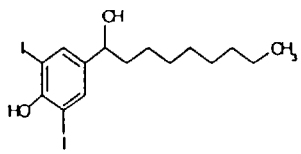 |
| 6-(3-iodobenzyloxy)-2,5,7,8-tetramethyl-chroman-2-carboxylic acid | 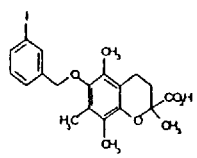 |
| 6-(2-iodobenzyloxy)-2,5,7,8-tetramethyl-chroman-2-carboxylic acid | 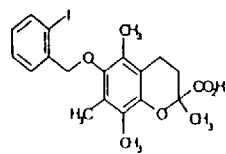 |
| 4-cyclohexylmethoxy-3,5-diiodobenzoic acid | 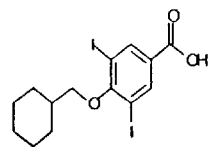 |
| 1-(3,5-diiodo-4-hydroxy)-phenyl-pentan-1-one | 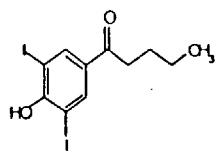 |
| 5,7-dihydroxy-6,8-diiodo-2-phenyl-chromen-4-one | 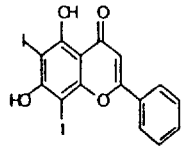 |
| N,N-dibenzyl-4-hydroxy-3,5-diiodo-benzamide | 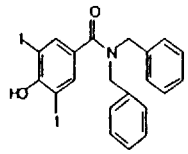 |
FIG. 2W

US 6,677,473 B1

PLASMINOGEN ACTIVATOR INHIBITOR ANTAGONISTS

RELATED APPLICATIONS

Benefit of priority under 35 U.S.C. §119(e) to U.S. provisional application Serial No. 60/185,564, filed Feb. 28, 2000, to Edwin L. Madison, Terence K. Brunck, Joseph Edward Semple, Marguerita Lim-Wilby and Kent E. Pryor, entitled "PLASMINOGEN ACTIVATOR INHIBITOR ANTAGONISTS" is claimed. This application is a continuation-in-part of U.S. application Ser. No. 09/580,535, filed May 26, 2000, to Edwin L. Madison, Terence K. Brunck, Joseph Edward Semple, Marguerita Lim-Wilby and Kent E. Pryor, entitled "PLASMINOGEN ACTIVATOR INHIBITOR ANTAGONISTS," and is a continuation-in-part of U.S. application Ser. No. 09/444,172, filed Nov. 19, 1999, to Edwin L. Madison, Terence K. Brunck, Joseph Edward Semple, Marguerita Lim-Wilby and Kent E. Pryor, entitled "PLASMINOGEN ACTIVATOR INHIBITOR ANTAGONISTS."

U.S. application Ser. No. 09/580,535 is a continuation-in-part of U.S. application Ser. No. 09/444,172 and claims benefit of priority under 35 U.S.C. §119(e) to U.S. provisional application Serial No. 60/185,564.

The disclosures of U.S. application Ser. Nos. 09/580,535, 09/444,172 and U.S. provisional application Serial No. 60/185,564 are incorporated herein by reference in their entirety.

FIELD OF THE INVENTION

Provided herein are compounds and pharmaceutical compositions that are plasminogen activator inhibitor (PAI) antagonists. In particular, methods of antagonizing PAI, particularly plasminogen activator inhibitor type 1 (PAI-1), with substituted and unsubstituted biaryl and benzyl ethers and thioethers, benzils and benzophenones are provided.

BACKGROUND OF THE INVENTION

Plasminogen activators (PA's), such as tissue type plasminogen activator (tPA) and urokinase plasminogen activator (uPA), are serine proteases that control the activation of the zymogen, plasminogen, to the active enzyme plasmin. Plasmin is important in a number of (patho)-physiological processes, including fibrinolysis, tissue remodelling, tumor growth and metastasis. The glycoprotein PAI-1 is an endogenous fast-acting inhibitor of PA activity. PAI-1 is a member of the serpin (serine protease inhibitor) family of protease inhibitors and is synthesized by a variety of cells including endothelial cells. An imbalance between PAs and PAI-1 contributes to several pathological conditions including thrombosis, inflammation, tumor growth and metastasis.

Thrombosis

Elevated circulating levels of PAI-1 can result in a down-regulation of fibrinolysis. This condition can contribute to the pathogenesis of various thrombotic disorders, including myocardial infarction, reocclusion following thrombolytic therapy, deep vein thrombosis and disseminated intravascular coagulation. Compounds and pharmaceutical compositions that antagonize PAI-1 can be used in the treatment of certain thrombotic disorders by enhancing the extent of endogenous fibrinolysis by PAs. In addition, PAI-1 antagonists, in this context, may enhance the efficacy of thrombolytic therapy where exogenous PAs such as recombinant tPA (r-tPA) is administered to a patient to reperfuse blood vessels occluded by thrombus as is commonly observed in myocardial infarction (see, e.g., U.S. Pat. Nos. 5,750,530, 5,902,812 and 5,891,877).

Cancer

Current therapies for cancer are generally characterized by limited efficacy, or significant and/or debilitating side effects. In certain solid tumor cancers, malignant tumors invade and disrupt nearby tissues and can also metastasize or spread to other organs and tissues. The impact of these secondary metastatic tumors on vital organs such as the lungs and the liver frequently leads to death. Surgery is used to remove solid tumors that are accessible to the surgeon and can be effective if the cancer has not metastasized. Radiation therapy also can be employed to irradiate a solid tumor and surrounding tissues and is a firstline therapy for inoperable tumors, but side effects are a limiting factor in treatment. Radiation therapy is used frequently in conjunction with surgery either to reduce the tumor mass prior to surgery or to destroy tumor cells that may remain at the tumor site after surgery. However, radiation therapy cannot assure that all tumor cells will be destroyed and has only limited utility for treating widespread metastases. While surgery and radiation therapy are the primary treatments for solid tumors, chemotherapy and hormonal treatments often are used as adjunctive therapies and also are used as primary therapies for inoperable or metastatic cancers. However, the side effects of these therapies can often limit their effectiveness due to patient tolerance and compliance.

Plasminogen Activator Inhibitor (PAI) and Its Role in Solid Tumor Cancer

The role of PAI, particularly PAI-1, in the natural progression of certain solid tumor cancers has been suggested based on the strong correlation of increased levels of this protein and a poor patient survival rates in certain types of cancer, including breast cancer. In addition, recent evidence in animals genetically lacking PAI (PAI knockouts) has demonstrated that the growth and metastasis of certain human tumors is significantly impaired, suggesting that PAI may play a pivotal role in the growth and metastatic migration of certain solid tumors (Bajou et al. (1998) *Nat. Med.* 4(8):923–928).

PAI antagonists that have been reported to date include the anthranilic acid derivative AR-H029953XX (Björquist et al. (1998) *Biochemistry* 37:1227–1234) and several diketopiperazines (piperazinediones)(see, e.g., Chariton et al. (1997) *Fibrinolysis & Proteolysis* 11(1):51–56; Charlton et al. (1996) *Thrombosis and Haemostasis* 75(5):808–815; and U.S. Pat. Nos. 5,750,530; 5,902,812; and 5,891,877). See also European Patent Application Publication No. EP 0 819 686. U.S. Pat. No. 3,794,729 discloses compounds for inhibition of blood platelet aggregation. Hence PAI-1 is a target for development of pharmaceuticals. Therefore, it is an object herein to provide compositions and methods for antagonizing the effects of PAI, particularly PAI-1, are provided. It is also an object herein to provide methods of treating, preventing, or ameliorating one or more symptoms of disease states, including, but not limited to, disease states mediated by or in which PAI-1 is implicated. These disease states include unstable angina, thrombotic disorders, such as myocardial infarction, reocclusion following thrombolytic therapy, deep vein thrombosis and disseminated intravascular coagulation, and cancer, particularly solid tumors, that are modulated or otherwise affected by the activity of PAI, particularly PAI-1. A further object herein is to provide methods of attenuating tumor or other cancer metastasis. Finally, it is an object herein to provide methods of modulating the interaction of PAs, particularly tPA and uPA, with PAI, particularly PAI-1.

SUMMARY OF THE INVENTION

Compounds and compositions useful as plasminogen activator inhibitor (PAI) antagonists are provided. The compounds and compositions are useful in the treatment, prevention, or amelioration of one or more symptoms of thrombotic disorders, such as myocardial infarction, reocclusion following thrombolytic therapy, deep vein thrombosis and disseminated intravascular coagulation, and cancer, particularly tumors, solid tumors, metastatic solid tumors and breast cancer. The compositions contain compounds that are active in assays that measure PAI-1 antagonist activity, such as an assay described herein. The compounds contain optionally substituted aryl and/or heteroaryl groups linked via various moieties, including but not limited to, ethers, thioethers, ketones, diketones and esters, and possess at least one acidic moiety, as defined herein, on one of the aryl or heteroaryl groups. An acidic group refers to a molecular fragment that is spatially and/or electronically capable of mimicking a carboxylic acid or that has acidic properties. As used herein, preferred acidic moieties include those that exist in anionic or salt form under physiological conditions. Among the preferred compounds are benzophenones, benzoate esters, benzyl ethers, sulfones and benzils.

In particular, provided herein are compounds and pharmaceutical compositions that contain therapeutically effective amounts of a compound of formula $MX'_jJ$, or pharmaceutically acceptable derivatives thereof, in a pharmaceutically acceptable carrier. In these embodiments, j is 0 or 1, and the formula $MX'_jJ$ is intended to represent the formulae M-X'-J (when j is 1) or MJ (when j is 0). In the compounds, X' is a direct link or is any suitable linkage such that the resulting compound has activity as a PAI-1 antagonist, and as noted above, at least one of M and J possesses an acidic group.

In one embodiment, the compounds for use in the compositions and methods provided herein have formula (I): $MX'_jJ$, or a pharmaceutically acceptable derivative thereof, wherein M, X', j and J are selected from (i) or (ii) as follows:
(i) j is 1 and the compound has the formula M-X'-J;
X' is selected from (i) or (ii) as follows:
(i) X' is a direct link or is a divalent group having any combination of the following groups: arylene, heteroarylene excluding benzo[b]thienylene, cycloalkylene, $C(R^{15})_2$, $-C(R^{15})=C(R^{15})-$, $>C=C(R^{23})(R^{24})$, $>C(R^{23})(R^{24})$, $-C\equiv C-$, O, $S(A)_u$, $P(D)_v(R^{15})$, $P(D)_v(ER^{15})$, $N(R^{15})$, $>N^+(R^{23})(R^{24})$ and C(E); where u is 0, 1 or 2; v is 0, 1, 2 or 3; A is O or $NR^{15}$; D is S or O; and E is S, O or $NR^{15}$; which groups may be combined in any order; or
(ii) X' is a trivalent, tetravalent, pentavalent or hexavalent group having any combination of the following groups: arylene, heteroarylene, cycloalkylene, $C(R^{15})_2$, $-C(R^{15})=C(R^{15})-$, $-C\equiv C-$, O, $S(A)_u$, $P(D)_v(R^{15})$, $P(D)_v(GR^{15})$, $N(R^{15})$, $>N^+(R^{23})(R^{24})$, $C(R^{16})_2$, $C(R^{15})(R^{16})$, $-C(R^{16})=C(R^{15})-$, $-C(R^{16})=C(R^{16})-$, $S(NR^{16})$, $P(D)_v(R^{16})$, $P(D)_v(GR^{16})$, $N(R^{16})$ or C(G); where u is 0, 1 or 2; v is 0, 1, 2 or 3; A is O or $NR^{15}$; D is S or O; and G is S, O, $NR^{15}$ or $NR^{16}$; which groups may be combined in any order, and forms one or more fused rings with M and/or J;

each $R^{15}$ is a monovalent group independently selected from the group consisting of hydrogen and $x^2-R^{18}$;
each $X^2$ is a divalent group independently having any combination of the following groups: a direct link, arylene, heteroarylene, cycloalkylene, $C(R^{17})_2$, $-C(R^{17})=C(R^{17})-$, $>C=C(R^{23})(R^{24})$, $>C(R^{23})(R^{24})$, $-C\equiv C-$, O, $S(A)_u$, $P(D)_v(R^{17})$, $P(D)_v(ER^{17})$, $N(R^{17})$, $N(COR^{17})$, $>N^+(R^{23})(R^{24})$ and C(E); where u is 0, 1 or 2; v is 0, 1, 2 or 3; A is O or $NR^{17}$; D is S or O; and E is S, O or $NR^{17}$; which groups may be combined in any order;
$R^{17}$ and $R^{18}$ are each independently selected from the group consisting of hydrogen, halo, pseudohalo, cyano, azido, nitro, $SiR^{27}R^{28}R^{25}$, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy and $NR^{19}R^{20}$;
$R^{19}$ and $R^{20}$ are each independently selected from hydrogen, alkyl, alkenyl, alkynyl, cycloalkyl, aryl, aralkyl, heteroaryl, heteroaralkyl and heterocyclyl;
h is 0, 1 or 2;
each $R^{16}$ is a divalent group independently having any combination of the following groups: arylene, heteroarylene, cycloalkylene, $C(R^{17})_2$, $-C(R^{17})=C(R^{17})-$, $-C\equiv C-$, O, $S(A)_u$, $P(D)_v(R^{17})$, $P(D)_v(GR^{17})$, $N(R^{17})$, $N(COR^{17})$, $>N^+(R^{23})(R^{24})$, $C(R^{21})_2$, $C(R^{17})(R^{21})$, $-C(R^{21})=C(R^{17})-$, $-C(R^{21})=C(R^{17})-$, $S(NR^{21})$, $P(D)_v(R^{21})$, $P(D)_v(GR^{21})$, $N(R^{21})$, $N(COR^{21})$ or C(G); where u is 0, 1 or 2; v is 0, 1, 2 or 3; A is O or $NR^{17}$; D is S or O; and G is S, O, $NR^{17}$ or $NR^{21}$; which groups may be combined in any order;
each $R^{21}$ is a divalent group and each is independently selected from alkylene, alkenylene, alkynylene, arylene, heteroarylene, heterocyclylene, cycloalkylene, cycloalkenylene, alkylenoxy, arylenoxy, aralkylene, aralkenylene, aralkynylene, heteroaralkylene, heteroaralkenylene, heteroaralkynylene, aralkylenoxy, and heteroaralkylenoxy;
$R^{23}$ and $R^{24}$ are selected from (i) or (ii) as follows:
(i) $R^{23}$ and $R^{24}$ are independently selected from the group consisting of hydrogen, alkyl, alkenyl, alkynyl, cycloalkyl, aryl and heteroaryl; or
(ii) $R^{23}$ and $R^{24}$ together form alkylene, alkenylene or cycloalkylene;
M and J are each independently selected from (i) or (ii):
(i) monocyclic or polycyclic cycloalkyl, heterocyclyl, aryl, heteroaryl, or two or more fused or bridged cycloalkyl, heterocyclyl, aryl or heteroaryl rings; or
(ii) one of M or J is alkyl, alkenyl, alkynyl, cycloalkyl, or heterocyclyl, and the other is selected as in (i);
with the proviso that at least one of M and J is substituted with at least one acidic group;
M and J are each independently unsubstituted or substituted with one or more substituents independently selected from $R^{15}$;
M and J are optionally substituted with and bridged by one or more divalent groups selected from $R^{16}$;
M and/or J are optionally substituted with and form a ring with one or more divalent groups selected from $R^{16}$;

$R^{25}$, $R^{27}$ and $R^{28}$ are each independently a monovalent group selected from hydrogen, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy and $NR^{19}R^{20}$;

$R^{15}$, $R^{16}$, $R^{17}$, $R^{18}$, $R^{19}$, $R^{20}$, $R^{21}$, $R^{23}$, $R^{24}$, $R^{25}$, $R^{27}$ and $R^{28}$ may be substituted with one or more substituents each independently selected from $Z^2$, wherein $Z^2$ is selected from alkyl, alkenyl, alkynyl, aryl, cycloalkyl, cycloalkenyl, hydroxy, $S(O)_h R^{35}$, $NR^{35}R^{36}{}_1$, $COOR^{35}$, $COR^{35}$, $CONR^{35}R^{36}$, $OC(O)NR^{35}R^{36}$, $N(R^{35})C(O)R^{36}$, alkoxy, aryloxy, heteroaryl, heterocyclyl, heteroaryloxy, heterocyclyloxy, aralkyl, aralkenyl, aralkynyl, heteroaralkyl, heteroaralkenyl, heteroaralkynyl, aralkoxy, heteroaralkoxy, alkoxycarbonyl, carbamoyl, thiocarbamoyl, alkoxycarbonyl, carboxyaryl, halo, pseudohalo, haloalkyl and carboxamido;

$R^{35}$ and $R^{36}$ are each independently selected from among hydrogen, halo, pseudohalo, cyano, azido, nitro, trialkylsilyl, dialkylarylsilyl, alkyldiarylsilyl, triarylsilyl, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy, amino, amido, alkylamino, dialkylamino, alkylarylamino, diarylamino and arylamino;

wherein, if X' is O or $CH_2$, the compound does not exhibit substantial thyroid hormone activity; and wherein the resulting compound has activity as a plasminogen activator inhibitor (PAI) antagonist; and wherein the resulting compound is chemically stable so that it can be formulated for pharmaceutical use; or (ii) j is 0 and the compound has the formula MJ;

M and J together form a fused multicyclic, preferably a fused bicyclic, tricyclic or tetracyclic, ring system where M and J are each independently selected from cycloalkyl, heterocyclyl, aryl and heteroaryl, with the proviso that at least one of M and J is substituted with at least one acidic group;

M and J are each independently unsubstituted or substituted with one or more substituents independently selected from $R^{15}$;

each $R^{15}$ is independently selected as in (i), above;

wherein the resulting compound has activity as a plasminogen activator inhibitor (PAI) antagonist; and wherein the resulting compound is chemically stable so that it can be formulated for pharmaceutical use.

In another embodiment, the compounds for use in the compositions and methods provided herein have formula (I): $MX'_j J$, or a pharmaceutically acceptable derivative thereof, wherein M, X', j and J are selected from (i) or (ii) as follows:

(i) j is 1 and the compound has the formula M-X'-J;

X' is selected from (i) or (ii) as follows:

(i) X' is a divalent group having any combination of the following groups: arylene, heteroarylene excluding benzo[b]thienylene, cycloalkylene, $C(R^5)_2$, $-C(R^5)=C(R^{15})-$, $>C=C(R^{23})(R^{24})$, $>C(R^{23})(R^{24})$, $-C\equiv C-$, O, $S(A)_u$, $P(D)_v(R^{15})$, $P(D)_v(ER^{15})$, $N(R^{15})$, $>N^+(R^{23})(R^{24})$ and $C(E)$;

where u is 0, 1 or 2; v is 0, 1, 2 or 3; A is O or $NR^{15}$; D is S or O; and E is S, O or $NR^{15}$; which groups may be combined in any order; or (ii) X' is a trivalent, tetravalent, pentavalent or hexavalent group having any combination of the following groups: arylene, heteroarylene, cycloalkylene, $C(R^{15})_2$, $-C(R^{15})=C(R^{15})-$, $-C\equiv C-$, O, $S(A)_u$, $P(D)_v(R^{15})$, $P(D)_v(GR^{15})$, $N(R^{15})$, $>N^+(R^{23})(R^{24})$, $C(R^{16})_2$, $C(R^{15})(R^{16})$, $-C(R^{16})=C(R^{15})-$, $-C(R^{16})=C(R^{16})-$, $S(NR^{16})$, $P(D)_v(R^{16})$, $P(D)_v(GR^{16})$, $N(R^{16})$ or $C(G)$; where u is 0, 1 or 2; v is 0, 1, 2 or 3; A is O or $NR^{15}$; D is S or O; and G is S, O, $NR^{15}$ or $NR^{16}$; which groups may be combined in any order, and forms one or more fused rings with M and/or J;

each $R^{15}$ is a monovalent group independently selected from the group consisting of hydrogen and $X^2-R^{18}$;

each $X^2$ is a divalent group independently having any combination of the following groups: a direct link, arylene, heteroarylene, cycloalkylene, $C(R^{17})_2$, $-C(R^{17})=C(R^{17})-$, $>C=C(R^{23})(R^{24})$, $>C(R^{23})(R^{24})$, $-C\equiv C-$, O, $S(A)_u$, $P(D)_v(R^{17})$, $P(D)_v(ER^{17})$, $N(R^{17})$, $N(COR^{17})$, $>N^+(R^{23})(R^{24})$ and $C(E)$; where u is 0, 1 or 2; v is 0, 1, 2 or 3; A is O or $NR^{17}$; D is S or O; and E is S, O or $NR^{17}$; which groups may be combined in any order;

$R^{17}$ and $R^{18}$ are each independently selected from the group consisting of hydrogen, halo, pseudohalo, cyano, azido, nitro, $SiR^{27}R^{28}R^{25}$, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy and $NR^{19}R^{20}$;

$R^{19}$ and $R^{20}$ are each independently selected from hydrogen, alkyl, alkenyl, alkynyl, cycloalkyl, aryl, aralkyl, heteroaryl, heteroaralkyl and heterocyclyl;

h is 0, 1 or 2;

each $R^{16}$ is a divalent group independently having any combination of the following groups: arylene, heteroarylene, cycloalkylene, $C(R^{17})_2$, $-C(R^{17})=C(R^{17})-$, $-C\equiv C-$, O, $S(A)_u$, $P(D)_v(R^{17})$, $P(D)_v(GR^{17})$, $N(R^{17})$, $N(COR^{17})$, $>N^+(R^{23})(R^{24})$, $C(R^{21})_2$, $C(R^{17})(R^{21})$, $-C(R^{21})=C(R^{17})-$, $-C(R^{21})=C(R^{17})-$, $S(NR^{21})$, $P(D)_v(R^{21})$, $P(D)_v(GR^{21})$, $N(R^{21})$, $N(COR^{21})$ or $C(G)$; where u is 0, 1 or 2; v is 0, 1, 2 or 3; A is O or $NR^{17}$; D is S or O; and G is S, O, $NR^{17}$ or $NR^{21}$; which groups may be combined in any order;

each $R^{21}$ is a divalent group and each is independently selected from alkylene, alkenylene, alkynylene, arylene, heteroarylene, heterocyclylene, cycloalkylene, cycloalkenylene, alkylenoxy, arylenoxy, aralkylene, aralkenylene, aralkynylene, heteroaralkylene, heteroaralkenylene, heteroaralkynylene, aralkylenoxy, and heteroaralkylenoxy;

$R^{23}$ and $R^{24}$ are selected from (i) or (ii) as follows:

(i) $R^{23}$ and $R^{24}$ are independently selected from the group consisting of hydrogen, alkyl, alkenyl, alkynyl, cycloalkyl, aryl and heteroaryl; or (ii) $R^{23}$ and $R^{24}$ together form alkylene, alkenylene or cycloalkylene;

M and J are each independently selected from (i) or (ii):

(i) monocyclic or polycyclic cycloalkyl, heterocyclyl, aryl, heteroaryl, or two or more fused or bridged cycloalkyl, heterocyclyl, aryl or heteroaryl rings; or (ii) one of M or J is alkyl, alkenyl, alkynyl, cycloalkyl, or heterocyclyl, and the other is selected as in (i);

with the proviso that at least one of M and J is substituted with at least one acidic group;

M and J are each independently unsubstituted or substituted with one or more substituents independently selected from $R^{15}$;

M and J are optionally substituted with and bridged by one or more divalent groups selected from $R^{16}$;

M and/or J are optionally substituted with and form a ring with one or more divalent groups selected from $R^{16}$;

$R^{25}$, $R^{27}$ and $R^{28}$ are each independently a monovalent group selected from hydrogen, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy and $NR^{19}R^{20}$;

$R^{15}$, $R^{16}$, $R^{17}$, $R^{18}$, $R^{19}$, $R^{20}$, $R^{21}$, $R^{23}$, $R^{24}$, $R^{25}$, $R^{27}$ and $R^{28}$ may be substituted with one or more substituents each independently selected from $Z^2$, wherein $Z^2$ is selected from alkyl, alkenyl, alkynyl, aryl, cycloalkyl, cycloalkenyl, hydroxy, $S(O)_hR^{35}$, $NR^{35}R^{36}$, $COOR^{35}$ $COR^{35}$, $CONR^{35}R^{36}$, $OC(O)NR^{35}R^{36}$, $N(R^{35})C(O)R^{36}$, alkoxy, aryloxy, heteroaryl, heterocyclyl, heteroaryloxy, heterocyclyloxy, aralkyl, aralkenyl, aralkynyl, heteroaralkyl, heteroaralkenyl, heteroaralkynyl, aralkoxy, heteroaralkoxy, alkoxycarbonyl, carbamoyl, thiocarbamoyl, alkoxycarbonyl, carboxyaryl, halo, pseudohalo, haloalkyl and carboxamido;

$R^{35}$ and $R^{36}$ are each independently selected from among hydrogen, halo, pseudohalo, cyano, azido, nitro, trialkylsilyl, dialkylarylsilyl, alkyldiarylsilyl, triarylsilyl, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy, amino, amido, alkylamino, dialkylamino, alkylarylamino, diarylamino and arylamino;

wherein, if X' is O or $CH_2$, the compound does not exhibit substantial thyroid hormone activity; and wherein the resulting compound has activity as a plasminogen activator inhibitor (PAI) antagonist; and wherein the resulting compound is chemically stable so that it can be formulated for pharmaceutical use; or (ii) j is O and the compound has the formula MJ;

M and J together form a fused multicyclic, preferably a fused bicyclic, tricyclic or tetracyclic, ring system where M and J are each independently selected from cycloalkyl, heterocyclyl, aryl and heteroaryl, with the proviso that at least one of M and J is substituted with at least one acidic group;

M and J are each independently unsubstituted or substituted with one or more substituents independently selected from $R^{15}$;

each $R^{15}$ is independently selected as in (i), above;

wherein the resulting compound has activity as a plasminogen activator inhibitor (PAI) antagonist; and wherein the resulting compound is chemically stable so that it can be formulated for pharmaceutical use.

Exemplary acidic groups include, but are not limited to, phenolic groups, carboxylic acid, sulfonic acid, sulfinic acid, phosphonic acid, phosphinic acid and boronic acid groups. Thus, acidic and acid mimicking groups include, but are not limited to, the following:

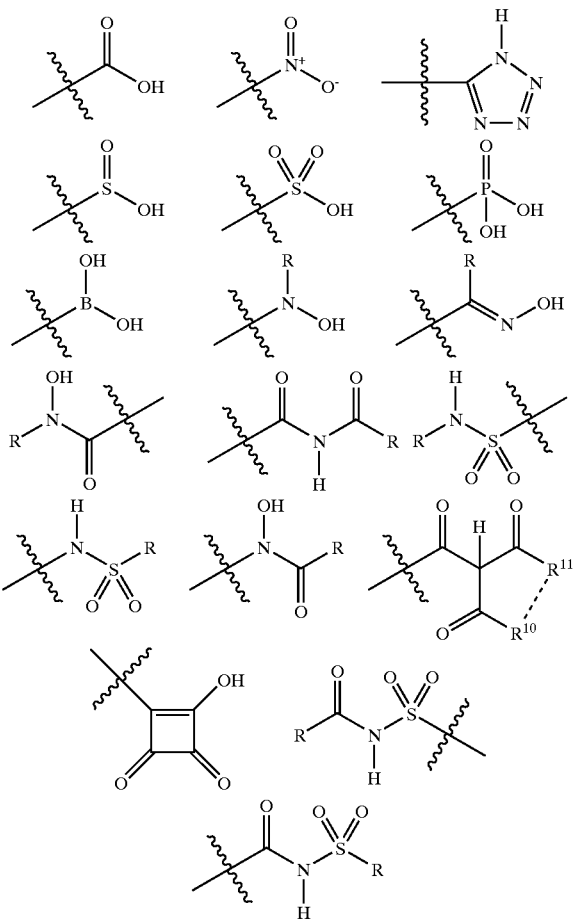

or cyclic derivatives thereof, where R is hydrogen, alkyl, alkenyl, alkynyl, cycloalkyl, heterocyclyl, aryl, heteroaryl, aralkyl or heteroaralkyl; and $R^{10}$ and $R^{11}$ are each independently alkyl, aryl, alkoxy, haloalkyl, haloalkoxy, halo or pseudohalo.

The substituents $R^{10}$, $R^{11}$, $R^{15}{}_1$ $R^{16}$, $R^{17}$, $R^{18}$, $R^{19}$, $R^{20}$, $R^{21}$, $R^{23}$, $R^{24}$ and $R^{25}$ are selected such that the resulting compound has PAI-1 antagonist activity, particularly in at least one assay described herein, and preferably at an $IC_{50}$ of less than about 100 $\mu$M. Significantly, the compounds, which include thyroxine analogs, preferably do not exhibit thyroid hormone activity at a level that would detectably alter thyroid function, i.e., altering pulse, body temperature or weight, in a human given a dose of the compound. Thus, preferred compounds do not exhibit substantial thyroid hormone activity and must exhibit PAI-1 antagonist activity, preferably exhibiting an $IC_{50}$ of at least about 100 $\mu$M in assays described herein.

Also of interest are any pharmaceutically-acceptable derivatives, including salts, esters, acids, enol ethers and esters, bases, solvates, hydrates and prodrugs of the compounds described herein. Pharmaceutically-acceptable salts, include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethylbenzimidazole, diethylamine and other alkylamines, piperazine and tris(hydroxymethyl) aminomethane; alkali metal salts, such as but not limited to lithium, potassium and sodium; alkali earth metal salts, such as but not limited to barium, calcium and magnesium; transition metal salts, such as but not limited to zinc, aluminum, and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates.

Pharmaceutical compositions formulated for administration by an appropriate route and means containing effective concentrations of one or more of the compounds provided herein, or pharmaceutically acceptable derivatives thereof, that deliver amounts effective for the treatment, prevention, or amelioration of one or more symptoms of thrombotic disorders, including, but not limited to, myocardial infarction, thrombosis associated with diabetes or obesity, reocclusion following thrombolytic therapy, deep vein thrombosis and disseminated intravascular coagulation, and cancer, including, but not limited to, tumors, solid tumors, metastatic solid tumors and breast cancer, are also provided. The effective amounts and concentrations are effective for ameliorating any of the symptoms of any of the disorders.

Methods for treatment, prevention, or amelioration of diseases mediated by or in which PAI-1 is implicated are provided. Such methods include methods of treatment, prevention and amelioration of one or more symptoms of thrombotic disorders, including, but not limited to, myocardial infarction, thrombosis associated with diabetes or obesity, reocclusion following thrombolytic therapy, deep vein thrombosis and disseminated intravascular coagulation, and cancer, including, but not limited to, tumors, solid tumors, metastatic solid tumors and breast cancer, using one or more of the compounds provided herein, or pharmaceutically acceptable derivatives thereof, are provided.

Methods of modulating the activity of PAI, particularly PAI-1, using the compounds and compositions provided herein are also provided. The compounds and compositions provided herein are active in assays that measure the activity of PAI, specifically PAI-1. Preferred are methods of inhibiting the activity of PAI, in particular PAI-1. Preferred compounds are those that do not exhibit substantial thyroid hormone activity.

Methods of modulating the interaction of PAs, particularly tPA and uPA, with PAI, particularly PAI-1, by administering one or more of the compounds provided herein, or pharmaceutically acceptable derivatives thereof, are provided.

Methods of attenuating metastasis by administration of one or more of the compounds and compositions provided herein are also provided.

Methods of modulating angiogenesis, preferably inhibiting angiogenesis, by administration of one or more of the compounds and compositions provided herein are provided.

In practicing the methods, effective amounts of the compounds or compositions containing therapeutically effective concentrations of the compounds formulated for systemic, including parenteral, oral, and intravenous delivery, local or topical application for the treatment of PAI-1 mediated or disorders in which PAI-1 is implicated, including, but are not limited to, unstable angina, thrombotic disorders, including, but not limited to, myocardial infarction, reocclusion following thrombolytic therapy, deep vein thrombosis and disseminated intravascular coagulation, and cancer, including, but not limited to, tumors, solid tumors, metastatic solid tumors and breast cancer, are administered to an individual exhibiting the symptoms of these disorders. The amounts are effective to ameliorate or eliminate one or more symptoms of the disorders.

Articles of manufacture containing packaging material, a compound or composition, or pharmaceutically acceptable derivative thereof, provided herein, which is effective for antagonizing PAI, particularly PAI-1, or for treatment, prevention or amelioration of one or more symptoms of thrombotic disorders, including, but not limited to, myocardial infarction, thrombosis associated with diabetes or obesity, reocclusion following thrombolytic therapy, deep vein thrombosis and disseminated intravascular coagulation, and cancer, including, but not limited to, tumors, solid tumors, metastatic solid tumors and breast cancer, within the packaging material, and a label that indicates that the compound or composition, or pharmaceutically acceptable derivative thereof, is used for antagonizing PAI, particularly PAI-1, or for treatment, prevention or amelioration of one or more symptoms of thrombotic disorders, including, but not limited to, myocardial infarction, thrombosis associated with diabetes or obesity, reocclusion following thrombolytic therapy, deep vein thrombosis and disseminated intravascular coagulation, and cancer, including, but not limited to, tumors, solid tumors, metastatic solid tumors and breast cancer, are provided.

DESCRIPTION OF THE FIGURES

FIGS. 1 and 2 set forth exemplary compounds for use in the compositions and methods provided herein, and their structures.

DETAILED DESCRIPTION OF PREFERRED EMBODIMENTS

A. Definitions

Figure 2D:
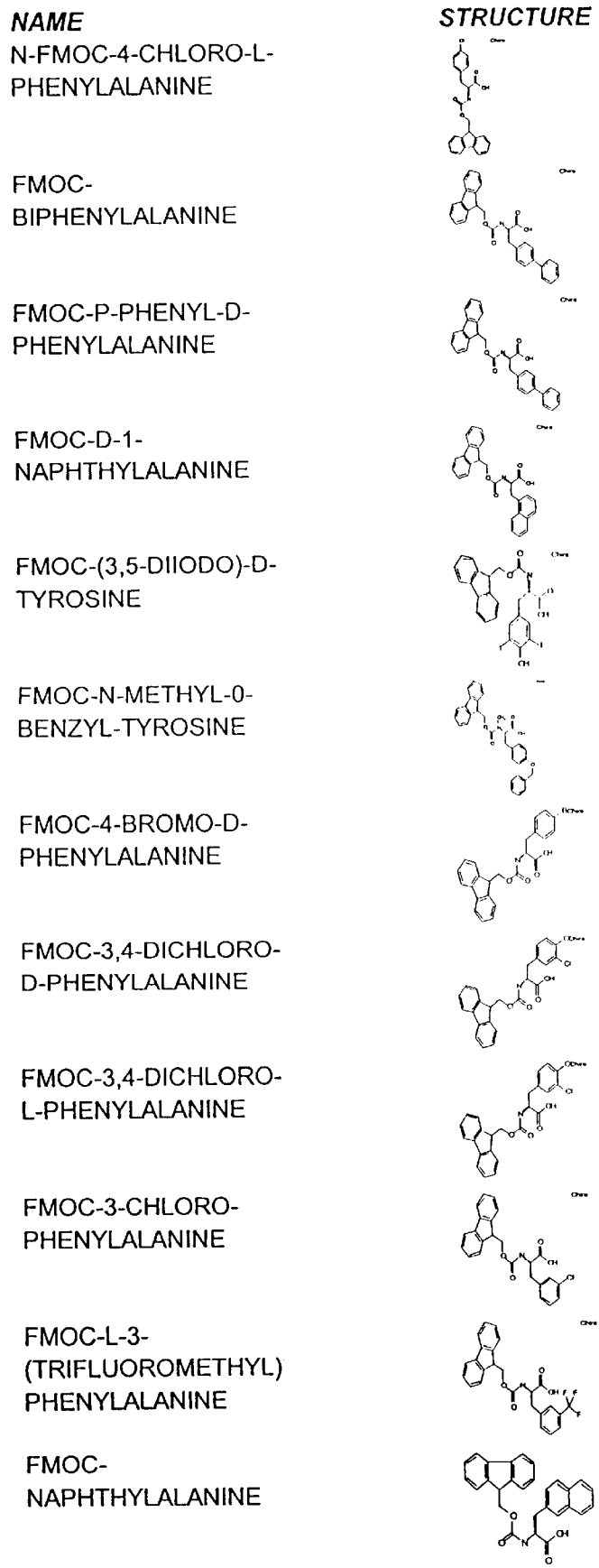

Unless defined otherwise, all technical and scientific terms used herein have the same meaning as is commonly understood by one of skill in the art to which this invention belongs. All patents, patent applications and publications referred to herein are incorporated by reference in their entirety.

As used herein, "plasmin" refers to the trypsin-like serine protease that is responsible for digesting fibrin in blood clots. Plasmin is generated from plasminogen by the action of another protease, plasminogen activator.

As used herein, "plasminogen" refers to the zymogen of plasmin.

As used herein, "plasminogen activator" or "PA" refers to a serine protease that acts on plasminogen to generate plasmin. PA is produced by many normal and invasive cells. Examples of PAs include, but are not limited to, uPA (urokinase, 70 kDa), tissue plasminogen activator (tPA, 55 kDa), and streptokinase.

As used herein, "plasminogen activator inhibitor" or "PAI" refers to an endogenous substance that inhibits the action of plasminogen activator. In particular, "PAI-1" refers to plasminogen activator inhibitor type 1, which is the fast acting form of PAI.

As used herein, a PAI-mediated pathology or pathological condition, refers to a condition in which PAI, particularly, PAI-1 is implicated. Such conditions include, but are not limited to, thrombosis, including thrombosis associated with diabetes or obesity, inflammation, tumor growth, metastasis and cardiovascular disorders.

As used herein, reference to an acidic group refers to a molecular fragment that is spatially and/or electronically capable of mimicking a carboxylic acid or that has acidic properties.

As used herein, thyroid hormone family is a class of compounds that upon administration results in an alteration of the thyroid function.

As used herein, chemically stable means that the compound is stable enough to be formulated for pharmaceutical use. Such chemical stability is well known to those of skill in the art and can be determined by well known routine methods. Whether a given compound is chemically stable enough to be formulated for pharmaceutical use depends on a number of factors including, but not limited to, the type of formulation and route of administration desired, the disease to be treated, and the method of preparing the pharmaceutical formulation.

As used herein, the $IC_{50}$ refers to an amount, concentration or dosage of a particular test compound that achieves a 50% inhibition of a maximal response, such as antagonism of PAI.

As used herein, $EC_{50}$ refers to a dosage, concentration or amount of a particular test compound that elicits a dose-dependent response at 50% of maximal expression of a particular response that is induced, provoked or potentiated by the particular test compound.

As used herein, pharmaceutically acceptable derivatives of a compound include salts, esters, enol ethers, enol esters, acids, bases, solvates, hydrates or prodrugs thereof that may be readily prepared by those of skill in this art using known methods for such derivatization and that produce compounds that may be administered to animals or humans without substantial toxic effects and that either are pharmaceutically active or are prodrugs. For example, acidic groups can be esterified or neutralized.

As used herein, treatment means any manner in which one or more of the symptoms of a condition, disorder or disease are ameliorated or otherwise beneficially altered. Treatment also encompasses any pharmaceutical use of the compositions herein, such as use for treating cancer.

As used herein, amelioration of the symptoms of a particular disorder by administration of a particular pharmaceutical composition refers to any lessening, whether permanent or temporary, lasting or transient that can be attributed to or associated with administration of the composition.

As used herein, a prodrug is a compound that, upon in vivo administration, is metabolized or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, em, Nogrady (1985) *Medicinal Chemistry A Biochemical Approach*, Oxford University Press, New York, pages 388–392).

It is to be understood that the compounds provided herein may contain chiral centers. Such chiral centers may be of either the (R) or (S) configuration, or may be a mixture thereof. Thus, the compounds provided herein may be enantiomerically pure, or be stereoisomeric or diastereomeric mixtures. In the case of amino acid residues, such residues may be of either the L- or D-form. The preferred configuration for naturally occurring amino acid residues is L. It is to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

As used herein, substantially pure means sufficiently homogeneous to appear free of readily detectable impurities as determined by standard methods of analysis, such as thin layer chromatography (TLC), gel electrophoresis, high performance liquid chromatography (HPLC) and mass spectrometry (MS), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

As used herein, alkyl, alkenyl and alkynyl carbon chains, if not specified, contain from 1 to 20 carbons, preferably 1 to 16 carbons, and are straight or branched. Alkenyl carbon chains of from 2 to 20 carbons preferably contain 1 to 8 double bonds, and the alkenyl carbon chains of 1 to 16 carbons preferably contain 1 to 5 double bonds. Alkynyl carbon chains of from 2 to 20 carbons preferably contain 1 to 8 triple bonds, and the alkynyl carbon chains of 2 to 1 6 carbons preferably contain 1 to 5 triple bonds. Exemplary alkyl, alkenyl and alkynyl groups herein include, but are not limited to, methyl, ethyl, propyl, isopropyl, isobutyl, n-butyl, sec-butyl, tert-butyl, isopentyl, neopentyl, tert-penytyl and isohexyl. The alkyl, alkenyl and alkynyl groups, unless otherwise specified, may be optionally substituted, with one or more groups, preferably alkyl group substituents that may be the same or different. As used herein, lower alkyl, lower alkenyl, and lower alkynyl refer to carbon chains having less than about 6 carbons. As used herein, "alk(en)(yn)yl" refers to an alkyl group containing at least one double bond and at least one triple bond.

As used herein, an "alkyl group substituent" includes halo, haloalkyl, preferably halo lower alkyl, aryl, hydroxy, alkoxy, aryloxy, alkyloxy, alkylthio, arylthio, aralkyloxy, aralkylthio, carboxy alkoxycarbonyl, oxo and cycloalkyl.

As used herein, "aryl" refers to cyclic groups containing from 5 to 19 carbon atoms. Aryl groups include, but are not limited to groups, such as fluorenyl, substituted fluorenyl, phenyl, substituted phenyl, naphthyl and substituted naphthyl, in which the substituent is lower alkyl, halogen, or lower alkoxy. As used herein, "aryl" also refers to aryl-containing groups, including, but not limited to, aryloxy, arylthio, arylcarbonyl and arylamino groups.

As used herein, an "aryl group substituent" includes alkyl, cycloalkyl, cycloalkylalkyl, aryl, heteroaryl optionally substituted with 1 or more, preferably 1 to 3, substituents selected from halo, halo alkyl and alkyl, aralkyl, heteroaralkyl, alkenyl containing 1 to 2 double bonds, alkynyl containing 1 to 2 triple bonds, alk(en)(yn)yl groups, halo, pseudohalo, cyano, hydroxy, haloalkyl and polyhaloalkyl, preferably halo lower alkyl, especially trifluoromethyl, formyl, alkylcarbonyl, arylcarbonyl that is optionally substituted with 1 or more, preferably 1 to 3, substituents selected from halo, halo alkyl and alkyl, heteroarylcarbonyl, carboxy, alkoxycarbonyl, aryloxycarbonyl, aminocarbonyl, alkylaminocarbonyl, dialkylaminocarbonyl, arylaminocarbonyl, diarylaminocarbonyl, aralkylaminocarbonyl, alkoxy, aryloxy, perfluoroalkoxy, alkenyloxy, alkynyloxy, arylalkoxy, aminoalkyl, alkylaminoalkyl, dialkylaminoalkyl, arylaminoalkyl, amino, alkylamino, dialkylamino, arylamino, alkylarylamino, alkylcarbonylamino, arylcarbonylamino, azido, nitro, mercapto, alkylthio, arylthio, perfluoroalkylthio, thiocyano, isothiocyano, alkylsulfinyl, alkylsulfonyl, arylsulfinyl, arylsulfonyl, aminosulfonyl, alkylaminosulfonyl, dialkylaminosulfonyl and arylaminosulfonyl.

As used herein, "aralkyl" refers to an alkyl group in which one of the hydrogen atoms of the alkyl is replaced by an aryl group.

As used herein, "heteroaralkyl" refers to an alkyl group in which one of the hydrogen atoms of the alkyl is replaced by a heteroaryl group.

As used herein, "cycloalkyl" refers to a saturated mono- or multi-cyclic ring system, preferably of 3 to 10 carbon atoms, more preferably 3 to 6 carbon atoms; cycloalkenyl and cycloalkynyl refer to mono- or multicyclic ring systems that respectively include at least one double bond and at least one triple bond. Cycloalkenyl and cycloalkynyl groups may preferably contain 3 to 10 carbon atoms, with cycloalkenyl groups more preferably containing 4 to 7 carbon atoms and cycloalkynyl groups more preferably containing 8 to 10 carbon atoms. The ring systems of the cycloalkyl, cycloalkenyl and cycloalkynyl groups may be composed of one ring or two or more rings which may be joined together in a fused, bridged or spiro-connected fashion, and may be optionally substituted with one or more alkyl group substituents. "Cycloalk(en)(yn)yl" refers to a cycloalkyl group containing at least one double bond and at least one triple bond.

As used herein, "heteroaryl" refers to a monocyclic or multicyclic ring system, preferably of about 5 to about 15 members where one or more, more preferably 1 to 3 of the atoms in the ring system is a heteroatom, that is, an element other than carbon, for example, nitrogen, oxygen and sulfur atoms. The heteroaryl may be optionally substituted with one or more, preferably 1 to 3, aryl group substituents. The heteroaryl group may be optionally fused to a benzene ring. Exemplary heteroaryl groups include, for example, furyl, imidazinyl, pyrrolidinyl, pyrimidinyl, tetrazolyl, thienyl, pyridyl, pyrrolyl, N-methylpyrrolyl, quinolinyl and isoquinolinyl, with pyridyl and quinolinyl being preferred. As used herein, "heteroaryl" also refers to heteroaryl-containing groups, including, but not limited to, heteroaryloxy, heteroarylthio, heteroarylcarbonyl and heteroarylamino.

As used herein, "heterocyclic" refers to a monocyclic or multicyclic ring system, preferably of 3 to 10 members, more preferably 4 to 7 members, even more preferably 5 to 6 members, where one or more, preferably 1 to 3 of the atoms in the ring system is a heteroatom, that is, an element other than carbon, for example, nitrogen, oxygen and sulfur atoms. The heterocycle may be optionally substituted with one or more, preferably 1 to 3 aryl group substituents. Preferred substituents of the heterocyclic group include hydroxy, amino, alkoxy containing 1 to 4 carbon atoms, halo lower alkyl, including trihalomethyl, such as trifluoromethyl, and halogen. As used herein, the term heterocycle may include reference to heteroaryl.

As used herein, the nomenclature alkyl, alkoxy, carbonyl, etc. are used as is generally understood by those of skill in this art. For example, as used herein alkyl refers to saturated carbon chains that contain one or more carbons; the chains may be straight or branched or include cyclic portions or be cyclic. As used herein, alicyclic refers to aryl groups that are cyclic.

Where the number of any given substituent is not specified (em, "haloalkyl"), there may be one or more substituents present. For example, "haloalkyl" may include one or more of the same or different halogens. As another example, "$C_{13}$alkoxyphenyl" may include one or more of the same or different alkoxy groups containing one, two or three carbons.

Where named substituents such as carboxy or substituents represented by variables such as W are separately enclosed in parentheses, yet possess no subscript outside the parentheses indicating numerical value and which follow substituents not in parentheses, e.g., "$C_{1-4}$alkyl(W)(carboxy)", "W" and "carboxy" are each directly attached to $C_{1-4}$alkyl.

As used herein, "halogen" or "halide" refers to F, Cl, Br or I.

As used herein, pseudohalides are compounds that behave substantially similar to halides. Such compounds can be used in the same manner and treated in the same manner as halides ($X^-$, in which X is a halogen, such as Cl or Br). Pseudohalides include, but are not limited to, cyanide, cyanate, thiocyanate, selenocyanate, trifluoromethoxy, and azide.

As used herein, "haloalkyl" refers to a lower alkyl radical in which one or more of the hydrogen atoms are replaced by halogen including, but not limited to, chloromethyl, trifluoromethyl, 1-chloro-2-fluoroethyl and the like.

As used herein, "haloalkoxy" refers to RO— in which R is a haloalkyl group.

As used herein, "sulfinyl" or "thionyl" refers to —S(O)—.
As used herein, "sulfonyl" or "sulfuryl" refers to —S(O)$_2$—.
As used herein, "sulfo" refers to —S(O)$_2$O—.

As used herein, "carboxy" refers to a divalent radical, —C(O)O—.

As used herein, "aminocarbonyl" refers to —C(O)NH$_2$.

As used herein, "alkylaminocarbonyl" refers to —C(O)NHR in which R is hydrogen or alkyl, preferably lower alkyl. As used herein "dialkylaminocarbonyl" as used herein refers to —C(O)NR'R in which R' and R are independently selected from hydrogen or alkyl, preferably lower alkyl; "carboxamide" refers to groups of formula —NR'COR.

As used herein, "diarylaminocarbonyl" refers to —C(O)NRR' in which R and R' are independently selected from aryl, preferably lower aryl, more preferably phenyl.

As used herein, "aralkylaminocarbonyl" refers to —C(O)NRR' in which one of R and R' is aryl, preferably lower aryl, more preferably phenyl, and the other of R and R' is alkyl, preferably lower alkyl.

As used herein, "arylaminocarbonyl" refers to —C(O)NHR in which R is aryl, preferably lower aryl, more preferably phenyl.

As used herein, "alkoxycarbonyl" refers to —C(O)OR in which R is alkyl, preferably lower alkyl.

As used herein, "aryloxycarbonyl" refers to —C(O)OR in which R is aryl, preferably lower aryl, more preferably phenyl.

As used herein, "alkoxy" and "alkylthio" refer to RO— and RS—, in which R is alkyl, preferably lower alkyl.

As used herein, "aryloxy" and "arylthio" refer to RO— and RS—, in which R is aryl, preferably lower aryl, more preferably phenyl.

As used herein, "alkylene" refers to a straight, branched or cyclic, preferably straight or branched, bivalent aliphatic hydrocarbon group, preferably having from 1 to about 20 carbon atoms, more preferably 1 to 12 carbons, even more preferably lower alkylene. The alkylene group is optionally substituted with one or more "alkyl group substituents." There may be optionally inserted along the alkylene group one or more oxygen, sulphur or substituted or unsubstituted nitrogen atoms, where the nitrogen substituent is alkyl as previously described. Exemplary alkylene groups include methylene (—CH$_2$—), ethylene (—CH$_2$CH$_2$—), propylene (—(CH$_2$)$_3$—), cyclohexylene (—C$_6$H$_{10}$—), methylenedioxy (—O—CH$_2$—O—) and ethylenedioxy (—O—(CH$_2$)$_2$—O—). The term "lower alkylene" refers to alkylene groups having 1 to 6 carbons. Preferred alkylene groups are lower alkylene, with alkylene of 1 to 3 carbon atoms being particularly preferred.

As used herein, "alkenylene" refers to a straight, branched or cyclic, preferably straight or branched, bivalent aliphatic hydrocarbon group, preferably having from 2 to about 20 carbon atoms and at least one double bond, more preferably 1 to 12 carbons, even more preferably lower alkenylene. The alkenylene group is optionally substituted with one or more "alkyl group substituents." There may be optionally inserted along the alkenylene group one or more oxygen, sulphur or substituted or unsubstituted nitrogen atoms, where the nitrogen substituent is alkyl as previously described. Exemplary alkenylene groups include —CH=CH—CH=CH— and —CH=CH—CH$_2$—. The term "lower alkenylene" refers to alkenylene groups having 2 to 6 carbons. Preferred alkenylene groups are lower alkenylene, with alkenylene of 3 to 4 carbon atoms being particularly preferred.

As used herein, "alkynylene" refers to a straight, branched or cyclic, preferably straight or branched, bivalent aliphatic hydrocarbon group, preferably having from 2 to about 20 carbon atoms and at least one triple bond, more preferably 1 to 12 carbons, even more preferably lower alkynylene. The alkynylene group is optionally substituted with one or more "alkyl group substituents." There may be optionally inserted along the alkynylene group one or more oxygen, sulphur or substituted or unsubstituted nitrogen atoms, where the nitrogen substituent is alkyl as previously described. Exemplary alkynylene groups include —C≡C—C≡C—, —C≡C— and —C≡C—CH$_2$—. The term "lower alkynylene" refers to alkynylene groups having 2 to 6 carbons. Preferred alkynylene groups are lower alkynylene, with alkynylene of 3 to 4 carbon atoms being particularly preferred.

As used herein, "alk(en)(yn)ylene" refers to a straight, branched or cyclic, preferably straight or branched, bivalent aliphatic hydrocarbon group, preferably having from 2 to about 20 carbon atoms and at least one triple bond, and at least one double bond; more preferably 1 to 12 carbons, even more preferably lower alk(en)(yn)ylene. The alk(en)(yn)ylene group is optionally substituted with one or more "alkyl group substituents." There may be optionally inserted along the alkynylene group one or more oxygen, sulphur or substituted or unsubstituted nitrogen atoms, where the nitrogen substituent is alkyl as previously described. Exemplary alk(en)(yn)ylene groups include —C=C—(CH$_2$)$_n$—C≡C—, where n is 1 or 2. The term "lower alk(en)(yn)ylene" refers to alk(en)(yn)ylene groups having up to 6 carbons. Preferred alk(en)(yn)ylene groups are lower alk(en)(yn)ylene, with alk(en)(yn)ylene of 4 carbon atoms being particularly preferred.

As used herein, "arylene" refers to a monocyclic or polycyclic, preferably monocyclic, bivalent aromatic group, preferably having from 5 to about 20 carbon atoms and at least one aromatic ring, more preferably 5 to 12 carbons, even more preferably lower arylene. The arylene group is optionally substituted with one or more "alkyl group substituents." There may be optionally inserted around the arylene group one or more oxygen, sulphur or substituted or unsubstituted nitrogen atoms, where the nitrogen substituent is alkyl as previously described. Exemplary arylene groups include 1,2-, 1,3- and 1,4-phenylene. The term "lower arylene" refers to arylene groups having 5 or 6 carbons. Preferred arylene groups are lower arylene.

As used herein, "heteroarylene" refers to a bivalent monocyclic or multicyclic ring system, preferably of about 5 to about 15 members where one or more, more preferably 1 to 3 of the atoms in the ring system is a heteroatom, that is, an element other than carbon, for example, nitrogen, oxygen and sulfur atoms. The heteroarylene group may be optionally substituted with one or more, preferably 1 to 3, aryl group substituents.

As used herein, "alkylidene" refers to a divalent group, such as =CR'R", which is attached to one atom of another group, forming a double bond. Exemplary alkylidene groups are methylidene (=CH$_2$) and ethylidene (=CHCH$_3$). As used herein, "aralkylidene" refers to an alkylidene group in which either R' or R" is an aryl group. "Cycloalkylidene" groups are those where R' and R" are linked to form a carbocyclic ring. "Heterocyclylidene" groups are those where at least one of R' and R" contain a heteroatom in the chain, and R' and R" are linked to form a heterocyclic ring.

As used herein, "amido" refers to the bivalent group —C(O)NH—. "Thioamido" refers to the bivalent group —C(S)NH—. "Oxyamido" refers to the bivalent group —OC(O)NH—. "Thiaamido" refers to the bivalent group —SC(O)NH—. "Dithiaamido" refers to the bivalent group —SC(S)NH—. "Ureido" refers to the bivalent group —HNC(O)NH—. "Thioureido" refers to the bivalent group —HNC(S)NH—.

As used herein, "semicarbazide" refers to —NHC(O)NHNH—. "Carbazate" refers to the bivalent group —OC(O)NHNH—. "Isothiocarbazate" refers to the bivalent group —SC(O)NHNH—. "Thiocarbazate" refers to the bivalent group —OC(S)NHNH—. "Sulfonylhydrazide" refers to the group —SO$_2$NHNH—. "Hydrazide" refers to the bivalent group —C(O)NHNH—. "Azo" refers to the bivalent group —N=N—. "Hydrazinyl" refers to the bivalent group —NH—NH—.

As used herein, the term "amino acid" refers to α-amino acids which are racemic, or of either the D- or L-configuration. The designation "d" preceding an amino acid designation (eq., dAla, dSer, dVal, etc.) refers to the D-isomer of the amino acid. The designation "dl" preceding an amino acid designation (em, dlPip) refers to a mixture of the L- and D-isomers of the amino acid.

As used herein, when any particular,group, such as phenyl or pyridyl, is specified, this means that the group is unsubstituted or is substituted. Preferred substituents where not specified are halo, halo lower alkyl, and lower alkyl.

As used herein, the abbreviations for any protective groups, amino acids and other compounds, are, unless indicated otherwise, in accord with their common usage, recognized abbreviations, or the IUPAC-IUB Commission on Biochemical Nomenclature (see, *Biochem.* 1972, 11, 942). For example, DMF=N,N-dimethylformamide, DMAc=N,N-di-methylacetamide; THF=tetrahydrofuran; TRIS=tris(hydroxymethyl)-aminomethane.

B. Compounds Useful as PAI Antagonists

Compounds and compositions useful as plasminogen activator inhibitor (PAI) antagonists are provided. The compositions contain compounds that are active in assays that measure PAI-1 antagonist activity. The compounds and compositions provided herein are thus useful in treatment, prevention, or amelioration of one or more symptoms of disease states in which PAI, particularly PAI-1, is implicated.

In one embodiment, the compounds for use in the compositions and methods provided herein have formula M-X'-J; where X' is selected from (i) or (ii) as follows:

(i) X' is a divalent group having any combination of the following groups: arylene, heteroarylene excluding benzo[b]thienylene, cycloalkylene, $C(R^{15})_2$, —$C(R^{15})$=$C(R^{15})$—, >C=$C(R^{23})(R^{24})$, >$C(R^{23})(R^{24})$, —C≡C—, O, $S(A)_u$, $P(D)_v(R^{15})$, $P(D)_v(ER^{15})$, $N(R^{15})$, >$N^+(R^{23})(R^{24})$ and C(E); where u is 0, 1 or 2; v is 0, 1, 2 or 3; A is O or $NR^{15}$; D is S or O; and E is S, O or $NR^{15}$; which groups may be combined in any order; or (ii) X' is a trivalent, tetravalent, pentavalent or hexavalent group having any combination of the following groups: arylene, heteroarylene, cycloalkylene, $C(R^{15})_2$, —$C(R^{15})$=$C(R^{15})$—, —C≡C—, O, $S(A)_u$, $P(D)_v$ $(R^{15})$, $P(D)_v(GR^{15})$, $N(R^{15})$, >$N^+(R^{23})(R^{24})$, $C(R^{16})_2$, $C(R^{15})(R^{16})$, —$C(R^{16})$=$C(R^{15})$—, —$C(R^{16})$=C $(R^{16})$—, $S(NR^{16})$, $P(D)_v(R^{16})$, $P(D)_v(GR^{16})$, $N(R^{16})$ or C(G); where u is 0, 1 or 2; v is 0, 1, 2 or 3; A is O or $NR^{15}$; D is S or O; and G is S, O, $NR^{15}$ or $NR^{16}$; which groups may be combined in any order, and forms one or more fused rings with M and/or J;

each $R^{15}$ is a monovalent group independently selected from the group consisting of hydrogen and $X^2$—$R^{18}$;

each $X^2$ is a divalent group independently having any combination of the following groups: a direct link, arylene, heteroarylene, cycloalkylene, $C(R^{17})_2$, —$C(R^{17})$=$C(R^{17})$—, >C=$C(R^{23})(R^{24})$, >$C(R^{23})$ $(R^{24})$, —C≡C—, O, $S(A)_u$, $P(D)_v(R^{17})$, $P(D)_v$ $(ER^{17})$, $N(R^{17})$, $N(COR^{17})$, >$N^+(R^{23})(R^{24})$ and C(E); where u is 0, 1 or 2; v is 0, 1, 2 or 3; A is O or $NR^{17}$; D is S or O; and E is S, O or $NR^{17}$; which groups may be combined in any order;

$R^{17}$ and $R^{18}$ are each independently selected from the group consisting of hydrogen, halo, pseudohalo, cyano, azido, nitro, $SiR^{27}R^{28}R^{25}$, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy and $NR^{19}R^{20}$;

$R^{19}$ and $R^{20}$ are each independently selected from hydrogen, alkyl, alkenyl, alkynyl, cycloalkyl, aryl, aralkyl, heteroaryl, heteroaralkyl and heterocyclyl;

h is 0, 1 or 2;

each $R^{16}$ is a divalent group independently having any combination of the following groups: arylene, heteroarylene, cycloalkylene, $C(R^{17})_2$, —$C(R^{17})$=C $(R^{17})$—, —C≡C—, O, $S(A)_u$, $P(D)_v(R^{17})$, $P(D)_v$ $(GR^{17})$, $N(R^{17})$, $N(COR^{17})$, >$N^+(R^{23})(R^{24})$, $C(R^{21})_2$, $C(R^{17})(R^{21})$, —$C(R^{21})$=$C(R^{17})$—, —$C(R^{21})$=$C(R^{17})$—, $S(NR^{21})$, $P(D)_v(R^{21})$, $P(D)_v$ $(GR^{21})$, $N(R^{21})$, $N(COR^{21})$ or C(G); where u is 0, 1 or 2; v is 0, 1, 2 or 3; A is O or $NR^{17}$; D is S or O; and G is S, O, $NR^{17}$ or $NR^{21}$; which groups may be combined in any order;

each $R^{21}$ is a divalent group and each is independently selected from alkylene, alkenylene, alkynylene, arylene, heteroarylene, heterocyclylene, cycloalkylene, cycloalkenylene, alkylenoxy, arylenoxy, aralkylene, aralkenylene, aralkynylene, heteroaralkylene, heteroaralkenylene, heteroaralkynylene, aralkylenoxy, and heteroaralkylenoxy;

$R^{23}$ and $R^{24}$ are selected from (i) or (ii) as follows:
(i) $R^{23}$ and $R^{24}$ are independently selected from the group consisting of hydrogen, alkyl, alkenyl, alkynyl, cycloalkyl, aryl and heteroaryl; or
(ii) $R^{23}$ and $R^{24}$ together form alkylene, alkenylene or cycloalkylene;

M and J are each independently selected from (i) or (ii):
(i) monocyclic or polycyclic cycloalkyl, heterocyclyl, aryl, heteroaryl, or two or more fused or bridged cycloalkyl, heterocyclyl, aryl or heteroaryl rings; or
(ii) one of M or J is alkyl, alkenyl, alkynyl, cycloalkyl, or heterocyclyl, and the other is selected as in (i);

with the proviso that at least one of M and J is substituted with at least one acidic group;

M and J are each independently unsubstituted or substituted with one or more substituents independently selected from $R^{15}$;

M and J are optionally substituted with and bridged by one or more divalent groups selected from $R^{16}$;

M and/or J are optionally substituted with and form a ring with one or more divalent groups selected from $R^{16}$;

$R^{25}$, $R^{27}$ and $R^{28}$ are each independently a monovalent group selected from hydrogen, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy and $NR^{19}R^{20}$;

each q is independently selected to be an integer from 2 to 20; each t is independently selected to be an integer from 1 to 20; each s is independently selected to be an integer from 5 to 16;

$R^{15}$, $R^{16}$ $R^{17}$, $R^{18}$, $R^{19}$, $R^{20}$, $R^{21}$, $R^{23}$, $R^{24}$, $R^{25}$, $R^{27}$ and $R^{28}$ may be substituted with one or more substituents each independently selected from $Z^2$, wherein $Z^2$ is selected from alkyl, alkenyl, alkynyl, aryl, cycloalkyl, cycloalkenyl, hydroxy, $S(O)_hR^{35}$, $NR^{35}R^{36}$, $COOR^{35}$, $COR^{35}$, $CONR^{35}R^{36}$, $OC(O)$ $NR^{35}R^{36}$, $N(R^{35})C(O)R^{36}$, alkoxy, aryloxy, heteroaryl, heterocyclyl, heteroaryloxy, heterocyclyloxy, aralkyl, aralkenyl, aralkynyl, heteroaralkyl, heteroaralkenyl, heteroaralkynyl, aralkoxy, heteroaralkoxy, alkoxycarbonyl, carbamoyl, thiocarbamoyl, alkoxycarbonyl, carboxyaryl, halo, pseudohalo, haloalkyl and carboxamido;

$R^{35}$ and $R^{36}$ are each independently selected from among hydrogen, halo, pseudohalo, cyano, azido, nitro, trialkylsilyl, dialkylarylsilyl, alkyldiarylsilyl, triarylsilyl, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy, amino, amido, alkylamino, dialkylamino, alkylarylamino, diarylamino and arylamino;

wherein, if X' is O or $CH_2$, the compound does not exhibit substantial thyroid hormone activity; and wherein the resulting compound has activity as a plasminogen activator inhibitor (PAI) antagonist; and wherein the resulting compound is chemically stable so that it can be formulated for pharmaceutical use.

In another embodiment, the compound has the formula MJ, where M and J together form a fused multicyclic, preferably a fused bicyclic, tricyclic or tetracyclic, ring system where M and J are each independently selected from cycloalkyl, heterocyclyl, aryl and heteroaryl, with the proviso that at least one of M and J is substituted with at least one acidic group;

M and J are each independently unsubstituted or substituted with one or more substituents independently selected from $R^{15}$, as defined above;

M and/or J are optionally substituted with and form a ring with one or more divalent groups selected from $R^{16}$, as defined above;

wherein the resulting compound has activity as a plasminogen activator inhibitor (PAI) antagonist; and wherein the resulting compound is chemically stable so that it can be formulated for pharmaceutical use.

Other compounds for use in the compositions and methods provided herein are ethers and thioethers and other linked heteroaryl and aryl compounds that have the formula M-X'-J, where X' is a direct link, O, S, $(CH_2)_d$, $(CH_2)_dO$ or $(CH_2)_dS$ or other linkage as described below, where d is an integer from 1 to 12, preferably 1–6; and M and J are each independently selected from one or more fused or linked aryl or heteroaryl, preferably aryl, more preferably phenyl, and are substituted with at least one acidic group preferably selected from a carboxylic acid, sulfonic acid, sulfinic acid, phenols, phosphonic acid, phosphinic acid or boronic acid group. Preferred acidic groups are phenol, carboxylic acid and sulfonic acid groups, more preferably $(CH_2)_aCOOH$, $(CH_2)_bCH(NRR')COOH$ and $(CH_2)_cSO_3H$ where R and R' are each independently hydrogen or an amino acid blocking or protecting group (see, e.g., Greene, T. W. *Protective Groups in Organic Synthesis* (1981) John Wiley & Sons, New York) including, but not limited to, tertbutoxycarbonyl (BOC), benzyloxycarbonyl (Cbz), 9-fluorenylmethoxycarbonyl (Fmoc), para-toluenesulfonyl (tosyl), 2,2,2-trichloroethoxycarbonyl, 2-trimethylsilylethoxycarbonyl, formyl, acetyl, benzyloxymethyl, benzyloxymethoxycarbonyl, unsubstituted or substituted benzoyl, unsubstituted or substituted benzyl, unsubstituted or substituted triphenylmethyl (trityl), or unsubstituted or substituted benzylidene; or R and R' together form phthaloyl, succinimidyl or maleimidyl; a is an integer from 0 to 6, b is an integer from 1 to 4, preferably 1 or 2; and c is an integer from 0 to 4, preferably 0.

M and J include rings that have from 3 to 20 members, preferably from 5 (for the cyclic and heteroaryl) to 7 members in each ring. M and J may be substituted further with one or more groups such as halide, pseudohalide, nitro, hydroxy, alkoxy, aryloxy, cycloalkoxy, haloalkyl, haloalkoxy, aryl, heteroaryl, heterocyclyl, alkyl or cycloalkyl. The aryl, heteroaryl, heterocyclyl and cycloalkyl substituents may be further substituted with $C_{1-20}$alkyl-L-, $C_{2-20}$alkenyl-L-, or $C_{2-20}$alkynyl-L-, where L is a direct link, amido, carboxy, carbonyl, carbamoyl, sulfonyl, carbamide, ureido, sulfonamide, hydrazinyl, hydrazide, semicarbazide, carbazate, thiocarbazate, isothiocarbazate or sulfonyl hydrazide.

Among the compounds for use in the compositions and methods herein are compounds of formula M-X'-J, or pharmaceutically acceptable derivatives thereof, in a pharmaceutically acceptable carrier, where:

X' includes, but is not limited to straight or branched chain alkylene, alkenylene, and alkynylene groups, alkylenoxy, arylene, arylenoxy, heteroarylene, heteroarylenoxy, ether, thioether, cycloalkylene, ester, alkylenoxycarbonyl, ketone, carbonyl, carboxyl, amido, amino, phosphine, sulfoxide, sulfonamide, sulfone, phosphinesulfonamides, phosphineoxides, phosphinesulfoxides, phosphoramidates, phosphinamidates, ureido, carbamates, and combinations thereof, and is optionally substituted with one or more substituents each independently selected from $R^{15}$; X' can be optionally selected from among these groups, to form a fused ring with M and/or J. X' is any of these groups or any suitable group such that the resulting compound has PAI-1 antagonist activity, preferably at a concentration less than about 100 μM, particularly in an assay exemplified herein. Typically X' will include less than 50, preferably less than 20, more preferably less than 10 members. X' may also form a fused ring with M and/or J. X' is optionally substituted with $R^{15}$.

In particular, X' includes, for example, a direct link, alkyl, alkynyl, $(C(R^{15})_2)_d$, —O—, —S—, $N(R^{15})$, $(S(O)_u)$ $(S(O)_2)_w$, $C(O)$, $(C(O))_w$, $(C(S(O)_u)_w(C(O)O)_w$, $(C(R^{15})_2)_d$ O, $(C(R^{15})_2)_dS(O)_u$, $O(C(R^{15})2)_d$, $S(O)_u(C(R^{15})_2)_d$, $(C(R^5)_2)_d$ $O(C(R^{15})_2)_d$, $(C(R^{15})_2)_dS(O)_u(C(R^{15})_2)_d$, $N(R^{15})(C(R^{15})_2)_d$, $(C(R^{15})_2)_dNR^{15}$, $(C(R^{15})_2)_dN(R^{15})(C(R^{15})_2)_d$, $(S(R^{15})(O_n)_w$, $(C(R^{15})_2)_d$, $(C(R^{15})_2)_dO(C(R^{15})_2)_d$, $(C(R^{15})_2)_d(C(O)O)_w(C(R^{15})_2)_d$, $(C(O)O)_w(C(R^{15})_2)_d$, $(C(R^{15})_2)_d(C(O)O)_w$, $(C(S)(R^{15})_w$, $(C(O))_w(CR^{15}_2)_d$, $(CR^{15})_d$ $(C(O))_w(CR^{15})_d$, $(C(R^{15})_2)_d(C(O))_w$, $N(R^{15})(C(R^{15})_2)_w$, $OC(R^{15})_2C(O)$, $O((R^{15})_2C(O)N(R^{15})$, $(C(R^{15})_2)_w$ $N(R^{15})(C(R^{15})_2)_w$, $(C(R^{15})_2)_wN(R^{15})$, $P(O)_v(R^{15})_x$, $P(O)_u(R^{15})_3$, $P(O)_u (C(R^{15})_2)_d$, and combinations of any of these groups, and includes linkages where X' forms a fused ring with one or both of M and J;

each u is independently 0 to 2;

v+x is 3 or 5;

each d is independently an integer from 1 to 20, preferably 1 to 12, more preferably 1–6, and most preferably 1 to 3;

each w is independently an integer selected from 1 to 6, preferably 1 to 3, more preferably 1 or 2;

each $R^{15}$ is independently hydrogen, alkyl, alkenyl, alkynyl, aryl, cycloalkyl, cycloalkenyl, alkoxy, aryloxy, heteroaryl, heterocycle, arylalkyl, aralkenyl, arylkynyl, heteroaralkyl, heteroaralkenyl, heteroaralkynyl, aryloxy, aralkyloxy, heteroaralkyloxy, alkylthio, alkylsulfinyl, alkylsulfonyl, alkoxycarbonyl, carbamoyl, thiocarbamoyl, alkoxycarbonyl, carboxyaryl, halogen, psuedohalide, haloalkyl, aminocarbonyl, carboxamide, and is preferably hydrogen, halide, lower alkyl, and pseudohalide;

M and J are each independently selected from monocyclic or comprise multiple carbocyclic or heterocyles, aryl, heteroaryl or two or more aryl or heteroaryl rings or one of M or J is alkyl, and at least one of M and J is substituted with at least one acidic group;

and may be further substituted with one or more substituents independently selected from halide, pseudohalide, nitro, hydroxy, alkoxy, aryl, heteroaryl, heterocyclyl, alkyl or cycloalkyl; wherein the aryl, heteroaryl, heterocyclyl and cycloalkyl substituents may be further substituted with $C_t$alkyl-L-, $C_q$alkenyl-L-, or $C_q$alkynyl-L-, where L is a direct link, amido, carboxy, carbonyl, carbamoyl, sulfonyl, carbamide, ureido, sulfonamide, hydrazinyl, hydrazide, semicarbazide, carbazate, thiocarbazate, isothiocarbazate or sulfonyl hydrazide, each q is independently selected to be an integer from 2 to 20, preferably 2 to 10, more preferably 2 to 6;

each t is independently selected to be an integer from 1 to 20, preferably 1 to 10, more preferably 1 to 6;

wherein, if X is O, the resulting compound does not exhibit substantial thyroid hormone activity.

The acidic group is selected from any group that is pharmaceutically suitable and acidic or an acid mimic as defined herein, and includes, but is not limited to, an acidic group such as a carboxylic acid (—COO—), sulfonic acid (—S(O)$_2$O—), sulfinic acid (—S(O)O—), phosphonic acid (—P(O)(OH)O—), phosphinic acid (—P(OH)O—), boronic acid (—B(OH)O—), alcohol, particularly phenolic, groups, and

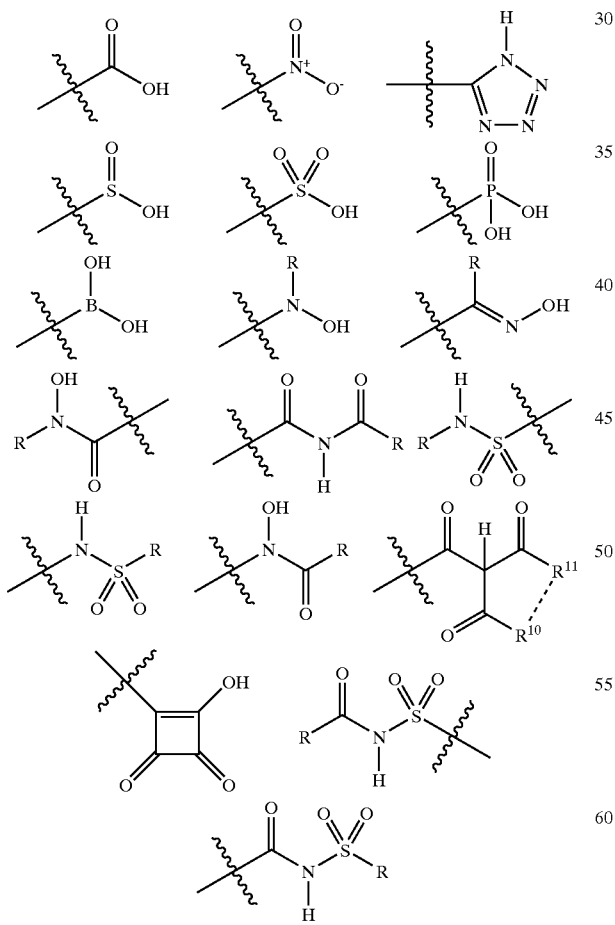

where $R^{10}$ and $R^{11}$ are as defined above, and are preferably independently selected from alkyl, aryl, alkoxy, haloalkyl, haloalkoxy, halo or pseudohalo, which are optionally further substituted with substituents independently selected from alkyl, aryl, alkoxy, haloalkyl, haloalkoxy, halo or pseudohalo, or optionally form a cyclic or heterocyclic group; and R is any group whereby the resulting moiety is acidic, and is preferably H, lower alkyl or aryl.

In certain embodiments, the compounds are substituted aryl and heteroaryl ethers and thioethers that possess at least one acidic moiety, including, but are not limited to the above-noted acidic groups.

In one embodiment, the compounds for use in the compositions and methods provided herein have formula (II):

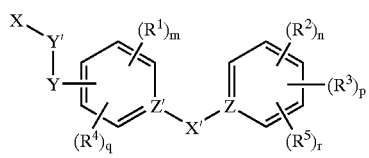

and pharmaceutically acceptable derivatives thereof, where X' is as defined above;

Z and Z' are each carbon; $R^1$ is alkyl, aryl, alkoxy, haloalkyl, haloalkoxy, halide or pseudohalide, preferably halide, more preferably iodo; m is an integer from 0 to 4, preferably from 1 to 4, more preferably 2, 3 or 4, most preferably 2; $R^2$, $R^3$, n and p are selected from (i) and (ii) as follows:

(i) $R^2$ is alkyl, aryl, alkoxy, haloalkyl, haloalkoxy, halide or pseudohalide, preferably halide, more preferably iodo; n is an integer from 0 to 5; $R^3$ is hydroxy or alkoxy, preferably OH; p is an integer from 0 to 3; or (ii) n and p are 1; and $R^2$ and $R^3$ together form, with the carbon to which each is attached, an aryl, aromatic ring, heteroaromatic ring, carbocyclic or heterocyclic ring, which is saturated or unsaturated, containing from about 3 to about 1 6 members, preferably 3 to about 10 members, more preferably 5 to 7 members; in particular, $R^2$ and $R^3$ together form —CH=CH—CH=CH—, —N=CH—CH=CH—, —CH=N—CH=CH—, —CH=CH—O—, —CH=CH—S— or —CH=CH—N($R^{20}$)— where $R^{20}$ is H, alkyl, aryl or aralkyl;

$R^4$ and $R^5$ are each independently selected from —SO$_3$—, —NO$_2$, alkyl, hydroxy, alkoxy, halide, pseudohalide; preferably —SO$_3$—, —NO$_2$ and lower alkyl; more preferably —SO$_3$—, —NO$_2$ and Me; q is an integer from 0 to 1; r is an integer from 0 to 2;

X is H, $C_{1-17}$alkyl-L-, $C_{2-17}$alkenyl-L-, or $C_{2-17}$alkynyl-L-; L is a direct link, amido, carboxy, carbonyl, carbamoyl, sulfonyl, carbamide, ureido, sulfonamide, hydrazinyl, hydrazide, semicarbazide, carbazate, thiocarbazate, isothiocarbazate or sulfonyl hydrazide;

Y' is a direct link; alkylene; a heterocyclylene group; or an acidic group, such as a phenol, carboxylic acid (—C(O)O—), sulfonic acid (—S(O)$_2$O—), sulfinic acid (—S(O)O—), phosphonic acid (—P(O)(OH)O—), phosphinic acid (—P(OH)O—) or boronic acid (—B(OH)O—), a phenol and any set forth above; is preferably a direct link, $C_{6-10}$alkylene, —S(O)$_2$O—,

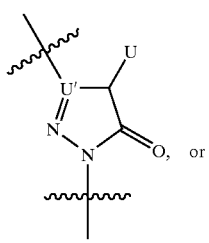

where U' is carbon and is attached to X; $R^9$ is $SO_3H$; w is an integer from 0 to 2; U is hydrogen, aryldiazo or heteroaryldiazo, preferably, hydrogen or phenyldiazo, more preferably H or

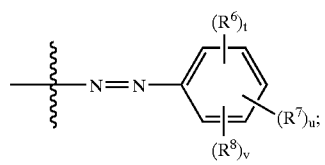

where $R^6$ is hydroxy or alkoxy, preferably OH; t is an integer from 0 to 3; $R^7$ is alkoxy, preferably $C_{1-3}$alkoxy; u is an integer from 0 to 3; $R^8$ is halide or pseudohalide, preferably halide; v is an integer from 0 to 3;

Y is a direct link, $C_{1-4}$alkyl(W)(carboxy), $C_{2-4}$alkenyl(W)(carboxy), $C_{2-4}$alkynyl(W)(carboxy), $C_{1-4}$alkyl(W)(sulfo), $C_{2-4}$alkenyl(W)(sulfo) or $C_{2-4}$alkynyl(W)(sulfo); where W is H, amino or A-D-E-G, where A is $C_{1-4}$alkylene, $C_{2-4}$alkenylene or $C_{2-4}$alkynylene; D is a direct link, amido, ureido, imino, azido, carbamoyl, thio or thionyl; E is a direct link, $C_{1-3}$alkylene, arylene or heteroarylene; and G is H, amino, nitro, cyano, hydrazinyl, thio or sulfonamido.

In certain embodiments, the compounds for use in the compositions and methods provided herein have formula (III):

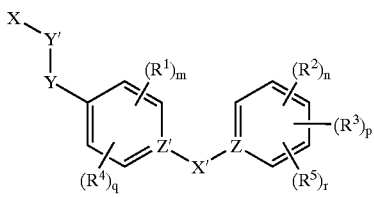

and pharmaceutically acceptable derivatives thereof, where X' is selected as described above;

Z and Z' are each carbon; $R^1$ is alkyl, aryl, alkoxy, haloalkyl, haloalkoxy, halide or pseudohalide, preferably halide, more preferably iodo; m is an integer from 0 to 4; $R^2$, $R^3$, n and p are selected from (i) and (ii) as follows:

(i) $R^2$ is alkyl, aryl, alkoxy, haloalkyl, haloalkoxy, halide or pseudohalide, preferably halide, more preferably iodo; n is an integer from 0 to 5; $R^3$ is hydroxy or alkoxy, preferably OH; p is an integer from 0 to 3; or (ii) n and p are 1; and $R^2$ and $R^3$ together form, with the carbon to which each is attached, an aryl, aromatic ring, heteroaromatic ring, carbocyclic or heterocyclic ring, which is saturated or unsaturated, containing from about 3 to about 16 members, preferably 3 to about 10 members, more preferably 5 to 7 members; in particular, $R^2$ and $R^3$ together form —CH=CH—CH=CH—, —N=CH—CH=CH—, —CH=N—CH=CH—, —CH=CH—O—, —CH=CH—S— or —CH=CH—N($R^{20}$)— where $R^{20}$ is alkyl, aryl or aralkyl;

$R^4$ and $R^5$ are each independently selected from —$SO_3^-$, —$NO_2$, alkyl, hydroxy, alkoxy, halide, pseudohalide; preferably —$SO_3^-$, —$NO_2$ and lower alkyl; more preferably —$SO_3^-$, —$NO_2$ and Me; q is an integer from 0 to 1; r is an integer from 0 to 2;

X is H, $C_{1-17}$alkyl-L-, $C_{2-17}$alkenyl-L-, or $C_{2-17}$alkynyl-L-; L is a direct link, amido, carboxy, carbonyl, carbamoyl, sulfonyl, carbamide, ureido, sulfonamide, hydrazinyl, hydrazide, semicarbazide, carbazate, thiocarbazate, isothiocarbazate or sulfonyl hydrazide;

Y' is a direct link; alkylene; a heterocyclylene group; or an acidic group such as a phenol; carboxylic acid (—COO—), sulfonic acid (—S(O)$_2$O—), sulfinic acid (—S(O)O—), phosphonic acid (—P(O)(OH)O—), phosphinic acid (—P(OH)O—), a phenol, or boronic acid (—B(OH)O—) any acid mimic, including those set forth above; preferably a direct link, $C_{6-10}$alkylene, —S(O)$_2$O—,

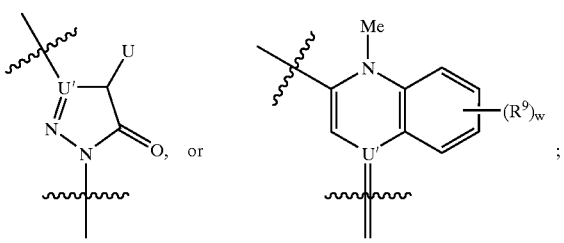

where U' is carbon and is attached to X; $R^9$ is $SO_3H$; w is an integer from 0 to 2; U is hydrogen, aryldiazo or heteroaryldiazo, preferably, hydrogen or phenyldiazo, more preferably H or

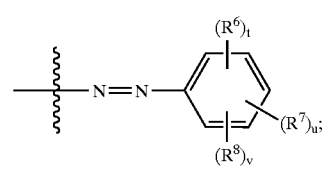

where $R^6$ is hydroxy or alkoxy, preferably OH; t is an integer from 0 to 3; $R^7$ is alkoxy, preferably $C_{1-3}$alkoxy; u is an integer from 0 to 3; $R^8$ is halide or pseudohalide, preferably halide; v is an integer from 0 to 3;

Y is a direct link, $C_{1-4}$alkyl(W)(carboxy), $C_{2-4}$alkenyl(W)(carboxy), $C_{2-4}$alkynyl(W)(carboxy), $C_{1-4}$alkyl(W)(sulfo), $C_{2-4}$alkenyl(W)(sulfo) or $C_{2-4}$alkynyl(W)(sulfo); where W is H, amino or A-D-E-G, where A is $C_{1-4}$alkylene, $C_{2-4}$alkenylene or $C_{2-4}$alkynylene; D is a direct link, amido, ureido, imino, azido, carbamoyl, thio or thionyl; E is a direct link, $C_{1-3}$alkylene, arylene or heteroarylene; and G is H, amino, nitro, cyano, hydrazinyl, thio or sulfonamido.

In certain embodiments herein, the compounds are of formula I with the provisos that (i) if m, n or p are not 0, then q and r are 0; (ii) if q or r are not 0, then m, n and p are 0; (iii) if X is not H, then Y is a direct link; (iv) if Y is not a direct link, then Y' is a direct link; (v) if Y' is not a direct link, then Y is a direct link; (vi) if D is not a direct link, then G is H; (vii) if D is a single bond and G is not H, then E is a single bond; and (viii) if E is not a direct link or C$_{1-3}$alkylene, then G is H.

In other embodiments, the compounds are of formula I with the proviso that X-Y'-Y is not hydrogen.

As noted, preferred compounds for use in the compositions and in the methods do not have significant thyroxine activity, or do not alter thyroxine secretion, when administered to a human. Such activity can be assessed in standard in vitro and in vivo tests, and for purposes herein would be desirably, less than about 30%, preferably less than about 10%, and more preferably, less than about 5%, the activity of thyroxine in such test. Most preferred compounds would not exhibit any thyroxine activity. In some instances, particularly, for treatment of acute disorders for which a small number of doses of the compounds will be administered, compounds that exhibit thyroxine activity and PAI-1 antagonist activity can be employed.

1. X' is O or S

In one embodiment, the compounds for use in the compositions and methods provided herein are aryl ethers and thioethers that have formula (III) and pharmaceutically acceptable derivatives thereof, wherein X' is O or S; and the remaining variables are as described above.

In certain embodiments, the compounds have formula II, or are pharmaceutically acceptable derivatives thereof, wherein:

X' is O or S;

Z and Z' are each carbon;

R$^1$ is halide or pseudohalide, preferably halide, more preferably I and is preferably ortho to Z';

R$^2$ is halide or pseudohalide, preferably halide, more preferably I and is preferably meta to Z;

m is an integer from 0 to 4, preferably 2;

n is an integer from 0 to 4, preferably 2;

R$^3$ is OH and is preferably para to Z;

p is an integer from 0 to 3, preferably 1;

R$^4$ and R$^5$ are each independently selected from —SO$_3^-$, —NO$_2$ and Me; q is an integer from 0 to 1; r is an integer from 0 to 2;

X is H, C$_{1-17}$alkyl-L-, C$_{2-17}$alkenyl-L-, or C$_{2-17}$alkynyl-L-; L is a direct link, amido, carboxy, carbonyl, carbamoyl, sulfonyl, carbamide, ureido, sulfonamide, hydrazinyl, hydrazide, semicarbazide, carbazate, thiocarbazate, isothiocarbazate or sulfonyl hydrazide;

Y' is a direct link, C$_8$alkylene, —S(O)$_2$O—,

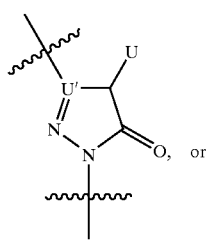 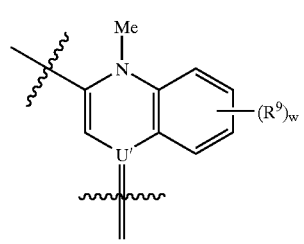

where U' is carbon and is attached to X; R$^9$ is SO$_3$H; w is an integer from 0 to 2; U is H or

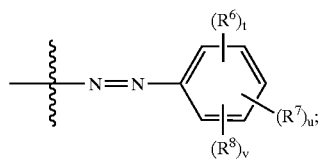

where R$^6$ is OH; t is an integer from 0 to 3; R$^7$ is C$_{1-3}$alkoxy; u is an integer from 0 to 3; R$^8$ is halo; v is an integer from 0 to 3;

Y is a direct link, C$_{1-4}$alkyl(W)(carboxy), C$_{2-4}$alkenyl(W)(carboxy), C$_{2-4}$alkynyl(W)(carboxy), C$_{1-4}$alkyl(W)(sulfo), C$_{2-4}$alkenyl(W)(sulfo) or C$_{2-4}$alkynyl(W)(sulfo); where W is H, amino or A-D-E-G, where A is C$_{1-4}$alkylene, C$_{2-4}$alkenylene or C$_{2-4}$alkynylene; D is a direct link, amido, ureido, imino, azido, carbamoyl, thio or thionyl; E is a direct link, C$_{1-3}$alkylene, arylene or heteroarylene; and G is H, amino, nitro, cyano, hydrazinyl, thio or sulfonamido;

with the provisos that (i) if m, n or p are not 0, then q and r are 0; (ii) if q or r are not 0, then m, n and p are 0; (iii) if X is not H, then Y is a direct link; (iv) if Y is not a direct link, then Y' is a direct link; (v) if Y' is not a direct link, then Y is a direct link; (vi) if D is not a direct link, then G is H; (vii) if D is a single bond and G is not H, then E is a single bond; and (viii) if E is not a direct link or C$_{1-3}$alkylene, then G is H.

a. Compounds Where m, n and p are 0

In a preferred embodiment, the compounds for use in the compositions and methods are of formula (III), wherein m, n and p are 0. In this embodiment, the compounds are preferably sulfonic acid derivatives, more preferably arylsulfonic acid derivatives. In particular, the compounds of this embodiment are biphenyl ethers substituted on one of the phenyl rings with a sulfonic acid group or the sulfonic acid group may be linked to a heteroaryl substituent on one of the phenyl rings. Preferred compounds possess a sulfonic acid group, or pharmaceutically acceptable derivative thereof, ortho or para to the oxygen atom of the biphenyl ether moiety.

Compounds of this embodiment possess a C$_{8-17}$alkyl group, generally an n C$_{10-17}$alkyl group, attached either directly to one of the phenyl rings of the biphenyl ether group or to the biphenyl ether moiety through a sulfonyloxy or heteroaryl substituent. Thus, the compounds of this embodiment are aliphatic arylsulfonates. In this embodiment, Y is preferably a direct link and X-Y' defines a substituent on the Z'-containing ring of the biphenyl ether moiety.

In preferred embodiments, the compounds are of formula (III), or pharmaceutically acceptable derivatives thereof, wherein Z and Z' are each carbon; R$^4$ and R$^5$ are each independently selected from —SO$_3^-$, —NO$_2$ and Me; q is 0 or 1; r is an integer from 0 to 2; X is H, Cl$_{1-7}$alkyl-L-, C$_{2-17}$alkenyl-L-, or C$_{2-17}$alkynyl-L-; L is a direct link, amido, carboxy, carbonyl, carbamoyl, sulfonyl, carbamide, ureido, sulfonamide, hydrazinyl, hydrazide, semicarbazide, carbazate, thiocarbazate, isothiocarbazate or sulfonyl hydrazide; Y' is C$_8$alkylene, —S(O)$_2$O—,

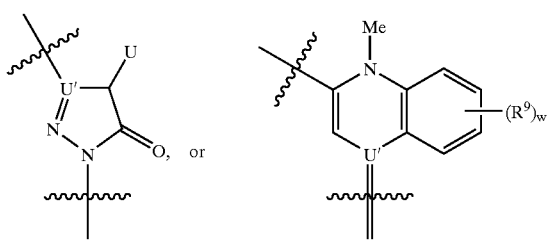

where U' is carbon and is attached to X; $R^9$ is $SO_3H$; w is an integer from 0 to 2, preferably 1; U is H or

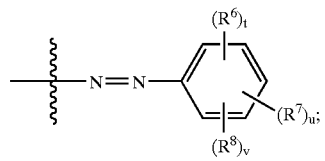

where $R^6$ is OH; t is an integer from 0 to 3, preferably 1; $R^7$ is $C_{1-3}$alkoxy; u is an integer from 0 to 3, preferably 0; $R^8$ is halo, preferably Cl; v is an integer from 0 to 3, preferably 1; and Y is a direct link.

In more preferred embodiments, the compounds are of formula (III), or pharmaceutically acceptable derivatives thereof, wherein Z and Z' are each carbon; $R^4$ and $R^5$ are each independently selected from —$SO_3^-$, —$NO_2$ and Me; q is 0 or 1; r is an integer from 0 to 2; X is H or $C_{10-17}$alkyl-L-; L is a direct link, amido, or sulfonyl hydrazide; Y' is $C_8$alkylene, —$S(O)_2O$—,

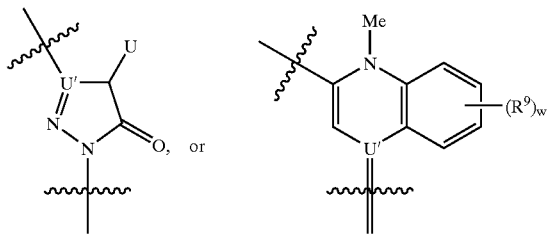

where U' is carbon and is attached to X; $R^9$ is $SO_3H$; w is 1; U is H or

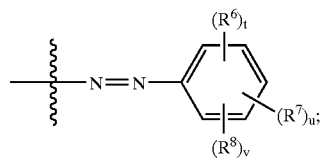

where $R^6$ is OH and is para to the diazo group; t is 1; u is 0; $R^8$ is Cl and is ortho to the diazo group; v is 1; and Y is a direct link.

In the embodiments described in detail above, X is preferably H, n-decyl, n-hexadecyl or n-heptadecyl. In other embodiments, r is 0; $R^4$ is $SO_3H$; and q is 1. In certain embodiments, q is 0; each $R^5$ is independently selected from $SO_3H$, $NO_2$ and Me; and r is 1 or 2.

b. Compounds Where q and r are 0

In another preferred embodiment, the compounds for use in the compositions and methods provided herein are of formula (III), wherein q and r are 0. In this embodiment, the compounds are preferably carboxylic acid derivatives, and are substituted with $(CH_2)_bCOOH$ or $(CH_2)_bCH(W)$—(COOH), where b is 1 or 2; and W is as defined above. Preferred substituents are $CH_2COOH$, $(CH_2)_2COOH$ and $CH_2CH(NH_2)COOH$.

Thus, the compounds of this embodiment are thyroxine analogs and derivatives thereof. In these embodiments, Y' is preferably a direct link and X-Y defines the above carboxyl substituents on the Z'-containing ring of the biphenyl ether moiety.

In more preferred embodiments, the compounds have formula (III), or are pharmaceutically acceptable derivatives thereof, wherein Z and Z' are each carbon; $R^1$ is I and is ortho to Z'; $R^2$ is I and is meta to Z; m is 1 or 2; n is 0, 1 or 2; $R^3$ is OH and is para to Z; p is 1; X is H; Y' is a direct link; and Y is $C_{1-4}$alkyl(W)(carboxy), $C_{2-4}$alkenyl(W)(carboxy), $C_{2-4}$alkynyl(W)(carboxy), $C_{1-4}$alkyl(W)(sulfo), $C_{2-4}$alkenyl(W)(sulfo) or $C_{2-4}$alkynyl(W)(sulfo); where W is H, amino or A-D-E-G, where A is $C_{1-4}$alkylene, $C_{2-4}$alkenylene or $C_{2-4}$alkynylene; D is a direct link, amido, ureido, imino, azido, carbamoyl, thio or thionyl; E is a direct link, $C_{1-3}$alkylene, arylene or heteroarylene; and G is H, amino, nitro, cyano, hydrazinyl, thio or sulfonamido.

In other more preferred embodiments, the compounds have formula (III) wherein Z and Z' are each carbon; $R^1$ is I and is ortho to Z'; $R^2$ is I and is meta to Z; m is 1 or 2; n is 0, 1 or 2; $R^3$ is OH and is para to Z; p is 1; X is H; Y' is a direct link; and Y is $(CH_2)_b$(carboxy) or $(CH_2)_bCH(W)$ (carboxy), where b is 1 or 2; and W is as defined above.

In certain embodiments, the compounds have formula (III) with the provisos that (vi) if D is not a direct link, then G is H; (vii) if D is a single bond and G is not H, then E is a single bond; and (viii) if E is not a direct link or $C_{1-3}$alkylene, then G is H. In other embodiments, the compound is not L-thyroxine.

Preferred groups for X-Y are $CH_2COOH$, $(CH_2)_2COOH$ and $CH_2CH(NRR')COOH$, where R and R' are each independently hydrogen or an amino acid blocking or protecting group (see, eq., Greene, T. W. *Protective Groups in Organic Synthesis* (1981) John Wiley & Sons, New York) including, but not limited to, tert-butoxycarbonyl (BOC), benzyloxycarbonyl (Cbz), 9-fluorenylmethoxycarbonyl (Fmoc), para-toluenesulfonyl (tosyl), 2,2,2-trichloroethoxycarbonyl, 2-trimethylsilylethoxycarbonyl, formyl, acetyl, benzyloxymethyl, benzyloxymethoxycarbonyl, unsubstituted or substituted benzoyl, unsubstituted or substituted benzyl, unsubstituted or substituted triphenylmethyl (trityl), or unsubstituted or substituted benzylidene; or R and R' together form phthaloyl, succinimidyl or maleimidyl. Thus, in particularly preferred embodiments, Z and Z' are each carbon; $R^1$ is I and is ortho to Z'; $R^2$ is I and is meta to Z; m is 1 or 2; n is 0, 1 or 2; $R^3$ is OH and is para to Z; p is 1; Y' is a direct link; and X-Y is $CH_2COOH$, $(CH_2)_2COOH$ or $CH_2CH(NH_2)COOH$.

2. X' is $(CH_2)_dO$ or $(CH_2)_dS$

In another embodiment, the compounds for use in the compositions and methods provided herein are aralkyl aryl, particularly benzyl phenyl, ethers and thioethers that have formula (III) and pharmaceutically acceptable derivatives thereof, wherein:

X' is $(CH_2)_dO$ or $(CH_2)_dS$ where d is an integer from 1 to 6, preferably from 1 to 3, more preferably 1;

Z and Z' are each carbon;

$R^1$ is halide, pseudohalide, alkoxy or alkyl; particularly halide or pseudohalide, preferably halide, more preferably I, and is preferably ortho to Z';

$R^2$ and $R^3$ are selected from (i) or (ii) as follows:
(i) $R^2$ is halide, pseudohalide, alkyl, aryl, heteroaryl, cycloalkyl, alkoxy, aryloxy, heteroaryloxy, cycloalkoxy, haloalkyl or haloalkoxy, preferably halide, more preferably I, and is preferably meta or para to Z; m is an integer from 0 to 4, preferably 2; n is an integer from 0 to 5, preferably 1 or 5, more preferably 1; $R^3$ is OH and is preferably para to Z; p is an integer from 0 to 3, preferably 0 or 1, more preferably 0; or (ii) $R^2$ and $R^3$ together form —CH=CH—CH=CH—, —N=CH— CH=CH— or —CH=N—CH=CH—;

$R^4$ and $R^5$ are each independently selected from —$SO_3^-$, —$NO_2$ and Me; q is an integer from 0 to 1, preferably 0; r is an integer from 0 to 2, preferably 0;

X is H, $C_{1-17}$alkyl-L-, $C_{2-17}$alkenyl-L-, or $C_{2-17}$alkynyl-L-; L is a direct link, amido, carboxy, carbonyl, carbamoyl, sulfonyl, carbamide, ureido, sulfonamide, hydrazinyl, hydrazide, semicarbazide, carbazate, thiocarbazate, isothiocarbazate or sulfonyl hydrazide;

Y' is a direct link, $C_8$alkylene, —$S(O)_2O$—,

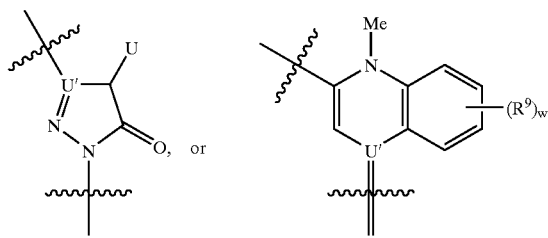

where U' is carbon and is attached to X; $R^9$ is $SO_3H$; w is an integer from 0 to 2; U is H or

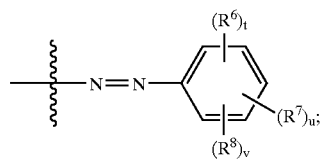

where $R^6$ is OH; t is an integer from 0 to 3; $R^7$ is $C_{1-3}$alkoxy; u is an integer from 0 to 3; $R^8$ is halo; v is an integer from 0 to 3;

Y is a direct link, $C_{1-4}$alkyl(W)(carboxy), $C_{2-4}$alkenyl(W)(carboxy), $C_{2-4}$alkynyl(W)(carboxy), $C_{1-4}$alkyl(W)(sulfo), $C_{2-4}$alkenyl(W)(sulfo) or $C_{2-4}$alkynyl(W)(sulfo), where W is H, amino or A-D-E-G, where A is $C_{1-4}$alkylene, $C_{2-4}$alkenylene or $C_{2-4}$alkynylene; D is a direct link, amido, ureido, imino, azido, carbamoyl, thio or thionyl; E is a direct link, $C_{1-3}$alkylene, arylene or heteroarylene; and G is H, amino, nitro, cyano, hydrazinyl, thio or sulfonamido;

with the provisos that (i) if m, n or p are not 0, then q and r are 0; (ii) if q or r are not 0, then m, n and p are 0; (iii) if X is not H, then Y is a direct link; (iv) if Y is not a direct link, then Y' is a direct link; (v) if Y' is not a direct link, then Y is a direct link; (vi) if D is not a direct link, then G is H; (vii) if D is a single bond and G is not H, then E is a single bond; and (viii) if E is not a direct link or $C_{1-3}$alkylene, then G is H.

In certain embodiments herein, the compound is selected with the proviso that when X' is $CH_2O$, Y-Y'-X is COOH and m, r and q are 0, then at least one of n and p is not 0. In other embodiments, the compound is selected with the proviso that when m, r and q are 0, then at least one of n and p is not 0. In these embodiments, the aryl ring containing Z is substituted with at least one substituent selected from $R^2$ and $R^3$. In other embodiments, the compound is selected with the proviso that it is not 3,5-diiodo-4-(benzyloxy)benzoic acid.

In preferred embodiments, q and r are 0 and the compounds have formula (IV):

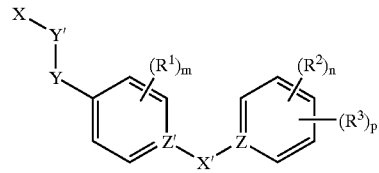

where X', Z, Z', Y, Y', X, $R^1$, $R^2$, $R^3$, m, n and p are as defined above.

In particular, Y' is a direct link, q and r are 0, and the compounds have formula (V):

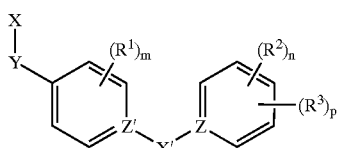

where X', Z, Z', Y, X, $R^1$, $R^2$, $R^3$, m, n and p are as defined above.

In other preferred embodiments, the compounds are of formula (V) where X' is $(CH_2)_dO$, where d is an integer from 1 to 6, preferably 1 to 3, more preferably 1; and Z, Z', Y, X, R', $R^2$, $R^3$, m, n and p are as defined above.

In particular, the compounds are of formula (V), where X' is $CH_2O$. In these embodiments, X-Y is preferably $(CH_2)_a$COOH, $(CH_2)_cSO_3H$, $NO_2$ or tetrazolyl, more preferably $(CH_2)_aCOOH$, $NO_2$ or tetrazolyl, most preferably $(CH_2)_a$COOH, where a is an integer from 0 to 6, preferably 0 to 3, more preferably 0 or 2; and c is an integer from 0 to 4.

Thus, in more preferred embodiments, the compounds are substituted benzyl ethers of para-hydroxy substituted benzoic acids and para-hydroxyphenyl substituted alkanoic acids. In these embodiments, the compounds have formula (VI):

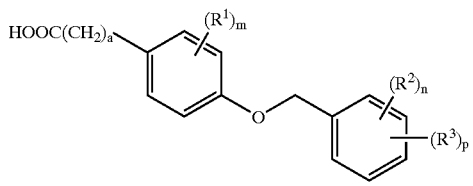

where $R^1$, $R^2$, $R^3$, m, n and p are as defined above, and a is an integer from 0 to 6. In preferred embodiments, R' is halide, pseudohalide, alkoxy or alkyl, particularly halide or pseudohalide, preferably halide, more preferably I; m is an integer from 0 to 4, preferably 1 to 4, more preferably 2; a is an integer from 0 to 6, preferably from 0 to 3, more preferably 0, 1 or 2; and $R^2$, $R^3$, n and p are selected as in (i) or (ii) as follows:

(i) $R^2$ is $NO_2$, CN, C(O)-aryl, C(O)-heteroaryl, haloalkylthio, halide, pseudohalide, alkyl, aryl, heteroaryl, cycloalkyl, alkoxy, aryloxy, heteroaryloxy, cycloalkoxy, haloalkyl or haloalkoxy, preferably halide, more preferably I; n is an integer from 0 to 5, preferably 1 to 5, more preferably 1 or 5, most preferably 1; and p is 0; or (ii) n and p are 1, and R² and R³ together form, with the carbon to which each is attached, an aryl, aromatic ring, heteroaromatic ring, carbocyclic or heterocyclic ring, which is saturated or unsaturated, containing from about 3 to about 16 members, preferably 3 to about 10 members, more preferably 5 to 7 members; in particular, R² and R³ together form —CH=CH—CH=CH—, —N=CH—CH=CH—, —CH=N—CH=CH—, —CH=CH—O—, —CH=CH—S—, or —CH=CH—N(R²⁰)—, where R²⁰ is alkyl, aryl or aralkyl.

In particularly preferred embodiments, R¹ is Cl, Br, or I, preferably I, and is ortho to the oxygen substituent; m is 2; R², R³, n and p are selected from (i) or (ii) as follows:
(i) R² is selected from I, Br, CH₃, C(CH₃)₃, Ph, OCH₃, CF₃, OCF₃, F, NO₂, CN, Cl, C(O)Ph, SCF₃ or 2-fluorophenoxy; n is 1, 2 or 5; and p is 0; or
(ii) n and p are 1; and R² and R³ together form —CH=CH—CH=CH— or —C(CH₃)₂—CH₂—CH₂—C(CH₃)₂—.

In other preferred embodiments, the compounds are of formula (VI) where R², R³, a, n and p are as defined above; m is an integer from 0 to 4, preferably 2; and R¹ is alkenyl, alkynyl, aryl, heteroaryl, aralkyl or heteroaralkyl, preferably alkenyl, aryl or heteroaryl, more preferably alkenyl or aryl; and is unsubstituted or substituted with one or more substituents selected from alkyl, alkenyl, alkynyl, aryl, cycloalkyl, cycloalkenyl, hydroxy, S(O)$_h$R¹⁷, NR¹⁷R¹⁸, COOR¹⁷, COR¹⁷, CONR¹⁷R¹⁸, alkoxy, aryloxy, heteroaryl, heterocyclyl, heteroaryloxy, heterocyclyloxy, arylalkyl, aralkenyl, arylkynyl, heteroaralkyl, heteroaralkenyl, heteroaralkynyl, aralkoxy, heteroaralkoxy, alkoxycarbonyl, carbamoyl, thiocarbamoyl, alkoxycarbonyl, carboxyaryl, halo, pseudohalo, haloalkyl and carboxamido, where h is 0, 1 or 2, and R¹⁷ and R¹⁸ are each independently selected from the group consisting of hydrogen, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy and NR¹⁹R²⁰, where R¹⁹ and R²⁰ are each independently selected from alkyl, alkenyl, alkynyl, cycloalkyl, aryl, aralkyl, heteroaryl, heteroaralkyl and heterocyclyl. In these embodiments, R¹ is preferably located ortho to the oxygen substituent.

In other embodiments herein, the compounds for use in the compositions and methods provided herein have the formula:

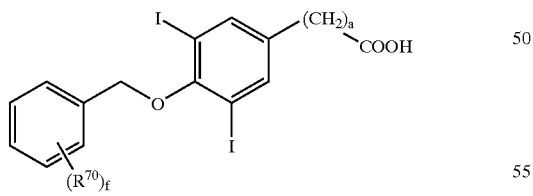

or a pharmaceutically acceptable derivative thereof, where a is an integer from 0 to 6; f is an integer from 1 to 5; each R⁷⁰ is independently halo, pseudohalo, nitro, cyano, azido, hydroxy and X³—R¹⁸; or any two of R⁷⁰ that substitute adjacent carbons on the ring together form, with the carbon atoms to which they are attached, a carbocyclic, aromatic, heterocyclic or heteroaromatic ring containing from 3 to 16 members;

X³ is a divalent group having any combination of the following groups: arylene, heteroarylene, cycloalkylene, C(R⁷)₂, —C(R¹⁷)=C(R¹⁷)—, >C=C(R²³)(R²⁴) >C(R²³)(R²⁴), —C≡C—, O, S(A)$_u$, P(D)$_v$(R¹⁷) P(D)$_x$(ER¹⁷), N(R¹⁷), >N⁺(R²³)(R²⁴) and C(E); where u is 0, 1 or 2; v is 0, 1, 2 or 3; A is O or NR¹⁷; D is S or O; and E is S, O or NR¹⁷; which groups may be combined in any order;

R¹⁷ and R¹⁸ are each independently selected from the group consisting of hydrogen, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy and NR¹⁹R²⁰;

R¹⁹ and R²⁰ are each independently selected from hydrogen, alkyl, alkenyl, alkynyl, cycloalkyl, aryl, aralkyl, heteroaryl, heteroaralkyl and heterocyclyl;

wherein the aryl, heteroaryl, heterocyclyl and cycloalkyl substituents of R⁷⁰ are unsubstituted or substituted with halo, pseudohalo, cyano, azido, NO₂, NR¹⁷R¹⁸, SiR¹⁷R¹⁸R²⁵, COR¹⁷, COOR¹⁷, CONR¹⁷R¹⁸, C$_t$alkyl-L-, C$_q$alkenyl-L-, C$_q$alkynyl-L-, C$_s$aryl-L- or C$_s$heteroaryl-L-, where L is a direct link, amido, carboxy, carbonyl, sulfonyl, ureido, sulfonamido, hydrazinyl, hydrazido, semicarbazido, carbazato, thiocarbazato, isothiocarbazato or sulfonylhydrazido;

R²⁵ is a monovalent group selected from hydrogen, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy and NR¹⁹R²⁰;

each q is independently selected to be an integer from 2 to 20; each t is independently selected to be an integer from 1 to 20; each s is independently selected to be an integer from 5 to 16;

R²³ and R²⁴ are selected from (i) or (ii) as follows:
(i) R²³ and R²⁴ are independently selected from the group consisting of hydrogen, alkyl, alkenyl, alkynyl, cycloalkyl, aryl and heteroaryl; or
(ii) R²³ and R²⁴ together form alkylene, alkenylene or cycloalkylene;

R¹⁷, R¹⁸, R¹⁹, R²⁰, R²³ R²⁴ and R²⁵ may be substituted with one or more substituents each independently selected from Z², wherein Z² is selected from alkyl, alkenyl, alkynyl, aryl, cycloalkyl, cycloalkenyl, hydroxy, S(O)$_h$R¹⁷, NR¹⁷R¹⁸, COOR¹⁷, COR¹⁷, CONR¹⁷R¹⁸, OC(O)NR¹⁷R¹⁸, N(R¹⁷)C(O)R¹⁸, alkoxy, aryloxy, heteroaryl, heterocyclyl, heteroaryloxy, heterocyclyloxy, aralkyl, aralkenyl, aralkynyl, heteroaralkyl, heteroaralkenyl, heteroaralkynyl, aralkoxy, heteroaralkoxy, alkoxycarbonyl, carbamoyl, thiocarbamoyl, alkoxycarbonyl, carboxyaryl, halo, pseudohalo, haloalkyl and carboxamido. In these embodiments, preferred compounds are those that possess and IC₅₀ value of less than 35 μM, preferably less than 17 μM, more preferably less than 10 μM at 10 min in an assay described herein (see, eq., Example 29, assay #2).

In other embodiments, the compounds are substituted benzyl ethers of ortho-hydroxy substituted benzoic acids and ortho-hydroxy-phenyl substituted alkanoic acids. In these embodiments, the compounds have formula (VIa):

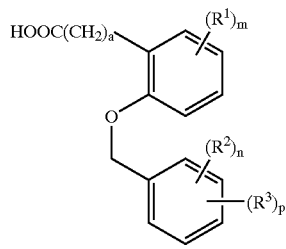

where $R^1$, $R^2$, $R^3$, m, n and p are as defined above, and a is an integer from 0 to 6. In preferred embodiments, $R^1$ is halide, pseudohalide, alkoxy or alkyl, particularly halide or pseudohalide, preferably halide, more preferably I; m is an integer from 0 to 4, preferably 1 to 4, more preferably 2; a is an integer from 0 to 6, preferably from 0 to 3, more preferably 0, 1 or 2; and $R^2$, $R^3$, n and p are selected as in (i) or (ii) as follows:

(i) $R^2$ is $NO_2$, CN, C(O)-aryl, C(O)-heteroaryl, haloalkylthio, halide, pseudohalide, alkyl, aryl, heteroaryl, cycloalkyl, alkoxy, aryloxy, heteroaryloxy, cycloalkoxy, haloalkyl or haloalkoxy, preferably halide, more preferably l; n is an integer from 0 to 5, preferably 1 to 5, more preferably 1 or 5, most preferably 1; and p is 0; or (ii) n and p are 1, and $R^2$ and $R^3$ together form, with the carbon to which each is attached, an aryl, aromatic ring, heteroaromatic ring, carbocyclic or heterocyclic ring, which is saturated or unsaturated, containing from about 3 to about 16 members, preferably 3 to about 10 members, more preferably 5 to 7 members; in particular, $R^2$ and $R^3$ together form —CH=CH—CH=CH—, —N=CH—CH=CH—, —CH=N—CH=CH—, —CH=CH—O—, —CH=CH—S—, or —CH=CH—N($R^{20}$)—, where $R^{20}$ is alkyl, aryl or aralkyl.

In particularly preferred embodiments, R' is Cl, Br, or I, preferably I, and is ortho and para to the oxygen substituent; m is 2; $R^2$, $R^3$, n and p are selected from (i) or (ii) as follows:

(i) $R^2$ is selected from I, Br, $CH_3$, $C(CH_3)_3$, Ph, $OCH_3$, $CF_3$, $OCF_3$, F, $NO_2$, CN, Cl, C(O)Ph, $SCF_3$ or 2-fluorophenoxy; n is 1, 2 or 5; and p is 0; or (ii) n and p are 1; and $R^2$ and $R^3$ together form —CH=CH—CH=CH— or —C($CH_3$)$_2$—$CH_2$—$CH_2$—C($CH_3$)$_2$—.

In other preferred embodiments, the compounds are of formula (VIa) where $R^2$, $R^3$, a, n and p are as defined above; m is an integer from 0 to 4, preferably 2; and $R^1$ is alkenyl, alkynyl, aryl, heteroaryl, aralkyl or heteroaralkyl, preferably alkenyl, aryl or heteroaryl, more preferably alkenyl or aryl; and is unsubstituted or substituted with one or more substituents selected from alkyl, alkenyl, alkynyl, aryl, cycloalkyl, cycloalkenyl, hydroxy, S(O)$_h$$R^{17}$, $NR^{17}R^{18}$, $COOR^{17}$, $COR^{17}$, $CONR^{17}R^{18}$, alkoxy, aryloxy, heteroaryl, heterocyclyl, heteroaryloxy, heterocyclyloxy, arylalkyl, aralkenyl, arylkynyl, heteroaralkyl, heteroaralkenyl, heteroaralkynyl, aralkoxy, heteroaralkoxy, alkoxycarbonyl, carbamoyl, thiocarbamoyl, alkoxycarbonyl, carboxyaryl, halo, pseudohalo, haloalkyl and carboxamido, where h is 0, 1 or 2, and $R^{17}$ and $R^{18}$ are each independently selected from the group consisting of hydrogen, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy and $NR^{19}R^{20}$, where $R^{19}$ and $R^{20}$ are each independently selected from alkyl, alkenyl, alkynyl, cycloalkyl, aryl, aralkyl, heteroaryl, heteroaralkyl and heterocyclyl. In these embodiments, $R^1$ is preferably located ortho to the oxygen substituent.

In other embodiments herein, the compounds for use in the compositions and methods provided herein have the formula:

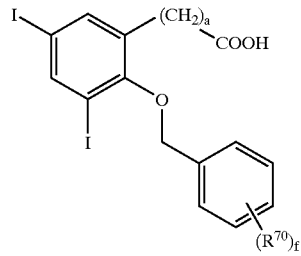

or a pharmaceutically acceptable derivative thereof, where a is an integer from 0 to 6; f is an integer from 1 to 5; each $R^{17}$ is independently halo, pseudohalo, nitro, cyano, azido, hydroxy and $X^3$—$R^{18}$; or any two of $R^{70}$ that substitute adjacent carbons on the ring together form, with the carbon atoms to which they are attached, a carbocyclic, aromatic, heterocyclic or heteroaromatic ring containing from 3 to 16 members;

$X^3$ is a divalent group having any combination of the following groups: arylene, heteroarylene, cycloalkylene, C($R^{17}$)$_2$, —C($R^{17}$)=C($R^{17}$)—, >C=C ($R^{23}$)($R^{24}$), >C($R^{23}$)($R^{24}$), —C≡C—, O, S(A)$_u$, P(D)$_v$ ($R^{17}$), P(D)$_v$(E$R^{17}$), N($R^{17}$), >$N^+$($R^{23}$)($R^{24}$) and C(E); where u is 0, 1 or 2; v is 0, 1, 2 or 3; A is O or $NR^{17}$; D is S or O; and E is S, O or $NR^{17}$; which groups may be combined in any order;

$R^{17}$ and $R^{18}$ are each independently selected from the group consisting of hydrogen, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy and $NR^{19}R^{20}$;

$R^{19}$ and $R^{20}$ are each independently selected from hydrogen, alkyl, alkenyl, alkynyl, cycloalkyl, aryl, aralkyl, heteroaryl, heteroaralkyl and heterocyclyl;

wherein the aryl, heteroaryl, heterocyclyl and cycloalkyl substituents of $R^{70}$ are unsubstituted or substituted with halo, pseudohalo, cyano, azido, $NO_2$, $NR^{17}R^{18}$, $SiR^{17}R^{18}R^{25}$, $COR^{17}$ $COOR^{17}$, $CONR^{17}R^{18}$, $C_t$alkyl-L-, $C_q$alkenyl-L-, $C_q$alkynyl-L-, $C_s$aryl-L- or $C_s$heteroaryl-L-, where L is a direct link, amido, carboxy, carbonyl, sulfonyl, ureido, sulfonamido, hydrazinyl, hydrazido, semicarbazido, carbazato, thiocarbazato, isothiocarbazato or sulfonylhydrazido;

$R^{25}$ is a monovalent group selected from hydrogen, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy and $NR^{19}R^{20}$;

each q is independently selected to be an integer from 2 to 20; each t is independently selected to be an integer from 1 to 20; each s is independently selected to be an integer from 5 to 16;

$R^{23}$ and $R^{24}$ are selected from (i) or (ii) as follows:
(i) $R^{23}$ and $R^{24}$ are independently selected from the group consisting of hydrogen, alkyl, alkenyl, alkynyl, cycloalkyl, aryl and heteroaryl; or
(ii) $R^{23}$ and $R^{24}$ together form alkylene, alkenylene or cycloalkylene;

$R^{17}$, $R^{18}$, $R^{19}$, $R^{20}$, $R^{23}$, $R^{24}$ and $R^{25}$ may be substituted with one or more substituents each independently selected from $Z^2$, wherein $Z^2$ is selected from alkyl, alkenyl, alkynyl, aryl, cycloalkyl, cycloalkenyl, hydroxy, $S(O)_h R^{17}$, $NR^{17}R^{18}$, $COR^{17}$, $COR^{17}$, $CONR^{17}R^{18}$, $OC(O)NR^{17}R^{18}$, $N(R^{17})C(O)R^{18}$, alkoxy, aryloxy, heteroaryl, heterocyclyl, heteroaryloxy, heterocyclyloxy, aralkyl, aralkenyl, aralkynyl, heteroaralkyl, heteroaralkenyl, heteroaralkynyl, aralkoxy, heteroaralkoxy, alkoxycarbonyl, carbamoyl, thiocarbamoyl, alkoxycarbonyl, carboxyaryl, halo, pseudohalo, haloalkyl and carboxamido. In these embodiments, preferred compounds are those that possess and $IC_{50}$ value of less than 35 μM, preferably less than 17 μM, more preferably less than 10 μM at 10 min in an assay described herein (see, e.g., Example 29, assay #2).

In other embodiments, the compounds for use in the compositions and methods provided herein are chroman derivatives of formula:

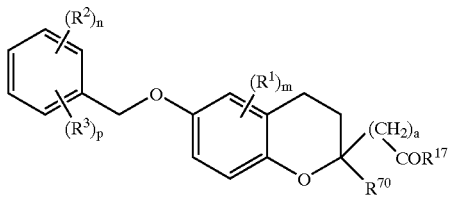

where $R^1$, $R^2$, $R^3$, $R^{17}$, $R^{70}$, a, n and p are selected as above; and m is 1 to 3, with the proviso the that the compound possesses at least one acidic group, as defined herein.

3. X' is —C(O)O—

In certain embodiments herein, the compounds are of formulae (I), (II) or (III) where X' is —C(O)O—. In a preferred embodiment, the compounds for use in the compositions and methods provided herein have formula (VII):

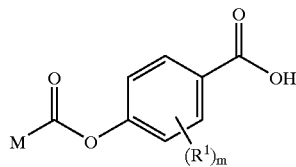

where $R^1$, m and M are as defined above. In particular, M is selected from alkyl, alkenyl, alkynyl, aryl, heteroaryl, heterocyclyl, aralkyl, heteroaralkyl, heterocyclylalkyl, cycloalkyl and cycloalkylalkyl. M is unsubstituted or substituted with one or more substituent independently selected from halo, pseudohalo, nitro, cyano, azido, $S(O)_h R^{17}$, $NR^{17}R^{18}$, $O(CH_2)_t C(O)R^{17}$, $O(CH_2)_i C(O)OR^{17}$, $COR^{17}$, $COOR^{17}$, $CONR^{17}R^{18}$, hydroxy, alkoxy, aryloxy, heteroaryloxy, aralkoxy, heteroaralkoxy, heterocyclyloxy, aryl, aralkyl, heteroaryl, heteroaralkyl, heterocyclyl, heterocyclylalkyl, alkyl, alkenyl, alkynyl, haloalkyl, haloalkoxy or cycloalkyl; i is an integer from 0 to 4; wherein the aryl, heteroaryl, heterocyclyl and cycloalkyl substituents of M are unsubstituted or substituted with halo, pseudohalo, cyano, azido, $NO_2$, $NR^{17}R^{18}$, $SiR^{17}R^{18}R^{19}$, $COR^{17}$, $COOR^{17}{}_1$ $CONR^{17}R^{18}$, $C_t$alkyl-L-, $C_q$alkenyl-L-, $C_q$alkynyl-L-, $C_s$aryl-L- or $C_s$heteroaryl-L-, where L is a direct link, amido, carboxy, carbonyl, sulfonyl, ureido, sulfonamido, hydrazinyl, hydrazido, semicarbazido, carbazato, thiocarbazato, isothiocarbazato or sulfonylhydrazido; each q is independently selected to be an integer from 2 to 20; each t is independently selected to be an integer from 1 to 20; each s is independently selected to be an integer from 5 to 16; and $R^{17}$, $R^{18}$ and $R^{19}$ are as defined above.

In these embodiments, $R^1$ is alkyl, aryl, alkoxy, haloalkyl, haloalkoxy, halide or pseudohalide, preferably halide, more preferably iodo; and m is an integer from 0 to 4, preferably 2. $R^1$ is preferably located ortho to the oxygen substituent, and the compounds have formula (VIIa):

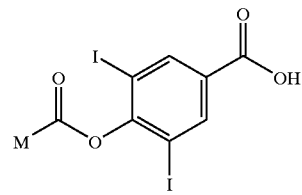

where M is alkyl, alkenyl, alkynyl, aryl, heteroaryl, heterocyclyl, aralkyl, heteroaralkyl, heterocyclylalkyl, cycloalkyl and cycloalkylalkyl. M is unsubstituted or substituted with one or more substituent independently selected from halo, pseudohalo, nitro, cyano, azido, $S(O)_h R^{17}$, $NR^{17}$, $R^{18}$, $O(CH_2)_t C(O)R^{17}$, $O(CH_2)_i C(O)OR^{17}$, $COR^{17}$, $COOR^{17}$, $CONR^{17}R^{18}$, hydroxy, alkoxy, aryloxy, heteroaryloxy, aralkoxy, heteroaralkoxy, heterocyclyloxy, aryl, aralkyl, heteroaryl, heteroaralkyl, heterocyclyl, heterocyclylalkyl, alkyl, alkenyl, alkynyl, haloalkyl, haloalkoxy or cycloalkyl; i is an integer from 0 to 4; wherein the aryl, heteroaryl, heterocyclyl and cycloalkyl substituents of M are unsubstituted or substituted with halo, pseudohalo, cyano, azido, $NO_2$, $NR^{17}R^{18}$, $SiR^{17}R^{18}R^{19}$, $COR^{17}$, $COOR^{17}$, $CONR^{17}R^{18}$, $C_t$alkyl-L-, $C_q$alkenyl-L-, $C_q$alkynyl-L-, $C_s$aryl-L- or $C_s$heteroaryl-L-, where L is a direct link, amido, carboxy, carbonyl, sulfonyl, ureido, sulfonamido, hydrazinyl, hydrazido, semicarbazido, carbazato, thiocarbazato, isothiocarbazato or sulfonylhydrazido; each q is independently selected to be an integer from 2 to 20; each t is independently selected to be an integer from 1 to 20; each s is independently selected to be an integer from 5 to 16; and $R^{17}$, $R^{18}$ and $R^{19}$ are as defined above.

In another preferred embodiment, the compounds for use in the compositions and methods provided herein have formula (VIIb):

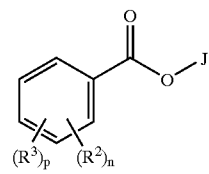

where $R^2$, $R^3$, n, p and J are as defined above.

In other embodiments, the compounds have formula (VIIb) where n is 1; $R^3$ is OH; p is 2; and $R^2$ is halide or pseudohalide, preferably halide, more preferably iodo. In these embodiments, $R^3$ is para to the —C(O)O— linker and each $R^2$ is preferably ortho to $R^3$. Thus, in these preferred embodiments, the compounds have formula (VIIc):

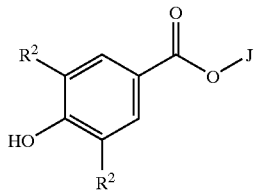

where $R^2$ and J are selected as above. $R^2$ is preferably iodo, and the compounds are esters of 3,5-diiodo-4-hydroxybenzoic acid.

In certain embodiments, the compounds of formulae (VIIb) and (VIIc) are selected with the proviso that J is not lower alkyl or a saturated heterocyclic group. In these embodiments, J is preferably aryl, heteroaryl, aralkyl, heteroaralkyl or higher (em, $C_{7-20}$) alkyl.

4. X' is $>C=C(R^{23})(R^{24})$

In other embodiments herein, the compounds have formulae (I), (II) or (III) where X' is $>C=C(R^{23})(R^{24})$. In a preferred embodiment, X' is $>C=C(R^{23})(R^{24})$ and the compounds for use in the compositions and methods have formula (VIII):

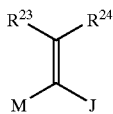

where M, J, $R^{23}$ and $R^{24}$ are selected as described above. In particular, $R^{23}$ and $R^{24}$ together form alkylene, alkenylene, cycloalkylene, arylene or heteroarylene; M and J are each independently monocyclic or polycyclic cycloalkyl, heterocyclyl, aryl, heteroaryl, or two or more fused or bridged cycloalkyl, heterocyclyl, aryl or heteroaryl rings, with the proviso that at least one of M and J is substituted with at least one acidic group; M and J are each independently unsubstituted or substituted with one or more substituents independently selected from halo, pseudohalo, nitro, cyano, azido, $S(O)_hR^{17}$, $NR^{17}R^{18}$, $O(CH_2)_iC(O)R^{17}$, $O(CH_2)_iC(O)OR^{17}$, $COR^{17}$, $COOR^{17}$, $CONR^{17}R^{18}$, hydroxy, alkoxy, aryloxy, heteroaryloxy, aralkoxy, heteroaralkoxy, heterocyclyloxy, aryl, aralkyl, heteroaryl, heteroaralkyl, heterocyclyl, heterocyclylalkyl, alkyl, alkenyl, alkynyl, haloalkyl, haloalkoxy or cycloalkyl; i is an integer from 0 to 4; wherein the aryl, heteroaryl, heterocyclyl and cycloalkyl substituents of M and J are unsubstituted or substituted with halo, pseudohalo, cyano, azido, $NO_2$, $NR^{17}R^{18}$, $SiR^{17}R^{18}R^{19}$, $COR^{17}$, $COOR^{17}$, $CONR^{17}R^{18}$, $C_t$alkyl -L, $C_q$alkenyl-L-, $C_q$alkynyl-L-, $C_s$aryl-L- or $C_s$heteroaryl-L-, where L is a direct link, amido, carboxy, carbonyl, sulfonyl, ureido, sulfonamido, hydrazinyl, hydrazido, semicarbazido, carbazato, thiocarbazato, isothiocarbazato or sulfonylhydrazido; each q is independently selected to be an integer from 2 to 20; each t is independently selected to be an integer from 1 to 20; each s is independently selected to be an integer from 5 to 16.

In more preferred embodiments, $R^{23}$ and $R^{24}$ together form alkenylene and the compound is a phenolphthalein derivative of formula (VIIIa):

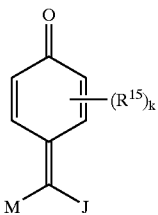

where M, J, and $R^{15}$ are as defined above; and k is an integer from 0 to 4, preferably 2. In more preferred embodiments, $R^{15}$ is iodo and is located ortho to the carbonyl group; k is 2; and the compounds have formula (VIIIb):

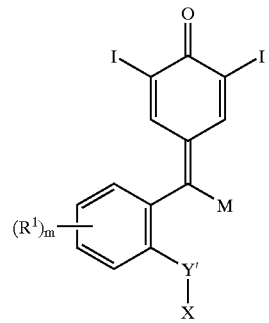

where $R^1$, m, and M are as defined above; and Y'-X form an acidic group, as defined herein, and preferably form COOH or $SO_3H$.

5. Fused Ring Compounds

In other embodiments, j is 0 and X' is absent. The compounds in these embodiments are fused bicyclic, tricyclic or tetracyclic compounds of formula (IX): MJ; where M and J together form a fused bicyclic, tricyclic or tetracyclic ring system where M and J are each independently selected from cycloalkyl, heterocyclyl, aryl and heteroaryl, with the proviso that at least one of M and J is substituted with at least one acidic group; M and J are each independently unsubstituted or substituted with one or more substituents independently selected from halo, pseudohalo, nitro, cyano, azido, $S(O)_hR^{17}$, $NR^{17}R^{18}$, $O(CH_2)_iC(O)R^{17}$, $O(CH_2)_iC(O)OR^{17}$, $COR^{17}$, $COOR^{17}$, $CONR^{17}R^{18}$, hydroxy, alkoxy, aryloxy, heteroaryloxy, aralkoxy, heteroaralkoxy, heterocyclyloxy, aryl, aralkyl, heteroaryl, heteroaralkyl, heterocyclyl, heterocyclylalkyl, alkyl, alkenyl, alkynyl, haloalkyl, haloalkoxy or cycloalkyl; h is 0, 1 or 2; i is an integer from 0 to 4; where the aryl, heteroaryl, heterocyclyl and cycloalkyl substituents of M and J are unsubstituted or substituted with halo, pseudohalo, cyano, azido, $NO_2$, $NR^{17}R^{18}$, $SiR^{17}R^{18}R^{19}$, $COR^{17}$, $COOR^{17}$, $CONR^{17}R^{18}$, $C_t$alkyl-$C_q$alkenyl-L-, $C_q$alkynyl-L-, $C_s$aryl-L- or $C_s$heteroaryl-L-, where L is a direct link, amido, carboxy, carbonyl, sulfonyl, ureido, sulfonamido, hydrazinyl, hydrazido, semicarbazido, carbazato, thiocarbazato, isothiocarbazato or sulfonylhydrazido; $R^{17}$ and $R^{18}$ are each independently selected from the group consisting of hydrogen, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy and $NR^{19}R^{20}$; $R^{19}$ and $R^{20}$ are each independently selected from alkyl, alkenyl, alkynyl, cycloalkyl, aryl, aralkyl, heteroaryl, heteroaralkyl and heterocyclyl; each q is independently selected to be an integer from 2 to 20; each t is independently selected to be an integer from 1 to 20; and each s is independently selected to be an integer from 5 to 16.

In more preferred embodiments, the compounds are naphthyl derivatives that have formula (IXa):

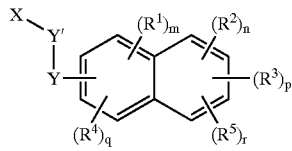

where $R^1$, $R^2$, $R^3$, $R^4$, $R^5$, Y, Y', X, m, n, p, q and r are as defined above. In particular, Y–Y'-X forms an acidic group, as defined herein, and is preferably OH, COOH, $SO_3H$ or $P(O)(OH)_2$, more preferably OH or COOH.

In other embodiments, the compounds are fused benzoheterocyclyl compounds. In these embodiments, the heterocyclyl group is a five or six membered heterocyclic ring containing from 1 to 3, preferably 1 or 2, more preferably 1, heteroatoms selected from O, N and S, more preferably O. In one embodiment, the heterocyclyl group is a six membered heterocycle containing one oxygen atom, including a pyran, dihydropyran or tetrahydropyran. Thus, compounds of this embodiment include those that have the formula:

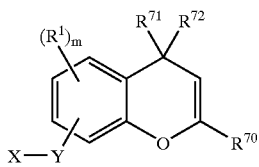

where $R^1$, m, X, Y and $R^{70}$ are as defined above; and $R^{71}$ and $R^{72}$ are selected from (i) or (ii) as follows:
  (i) $R^{71}$ and $R^{72}$ are independently selected from the group consisting of hydrogen, alkyl, alkenyl, alkynyl, cycloalkyl, aryl and heteroaryl; or
  (ii) $R^{71}$ and $R^{72}$ together form oxo, thia, $NR^{17}$, alkylene, alkenylene or cycloalkylene.

In certain embodiments herein, $R^{71}$ and $R^{72}$ are selected from oxo thia, $NR^{17}$, alkylene, alkenylene or cycloalkylene, preferably from oxo and thia, particularly oxo. Thus, in these embodiments, the compounds have the formula:

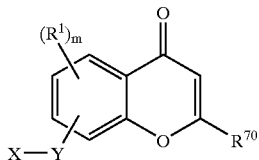

where $R^1$, $R^{70}$, X, Y and m are selected as above. In particular, $R^{70}$ is aryl or heteroaryl, more particularly aryl, preferably phenyl. Each $R^1$ is hydroxy, halo or pseudohalo, preferably hydroxy or halo, more preferably hydroxy or iodo, and is located ortho to Y-X. Y-X is preferably OH; and m is preferably 3.

In other embodiments, the compounds are selected with the proviso that $R^{70}$ is not phenyl. In further embodiments, the compounds are selected with the proviso that $R^{71}$ and $R^{72}$ together do not form oxo. In another embodiment, the compounds are selected with the proviso the n and p are not both 2. In certain embodiments, the compounds are selected with the proviso that the compound is not 5,7-dihydroxy-6,8-diiodo-2-phenylchromen-4-one.

6. Silylated Compounds

Certain of the compounds provided herein are silylated compounds. The compounds of these embodiments are generally silyl ester and ether derivatives of the compounds provided herein. In one embodiment, the compounds have formulae (X):

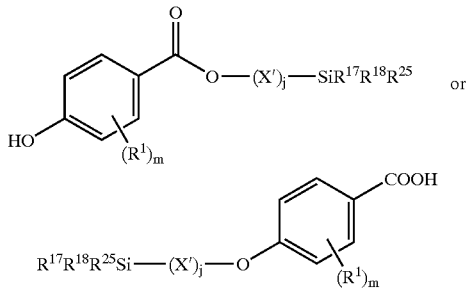

where $R^1$, m, X', j, $R^{17}$, $R^{18}$ and $R^{25}$ are as defined above. In preferred embodiments, $R^{17}$, $R^{18}$ and $R^{25}$ are selected from alkyl and aryl; $R^1$ is halo or pseudohalo, preferably halo, more preferably iodo; and the compounds are silyl ester derivatives of iodo-substituted-4-hydroxybenzoic acids, particularly 3,5-diiodo-4-hydroxybenzoic acid.

7. X' is —C(O)— or —CH(OH)— or Derivatives Thereof a. X' is —C(O)— or a Derivative Thereof

In a preferred embodiment, X' is —C(O)— or derivatives thereof, including, but not limited to, —C($NR^{15}$)—, —C($OR^{30}$)($OR^{31}$)—, —C($SR^{30}$)($SR^{31}$)—, and —C($OR^{30}$)($SR^{31}$)—, where $R^{15}$ is a monovalent group selected from the group consisting of hydrogen, alkyl, alkenyl, alkynyl, aryl, cycloalkyl, cycloalkenyl, hydroxy, $S(O)_hR^{17}$, $NR^{17}R^{18}$ $COOR^{17}$, $COR^{17}$, $CNR^{17}R^{18}$, alkoxy, aryloxy, heteroaryl, heterocyclyl, heteroaryloxy, heterocyclyloxy, arylalkyl, aralkenyl, arylkynyl, heteroaralkyl, heteroaralkenyl, heteroaralkynyl, aralkoxy, heteroaralkoxy, alkoxycarbonyl, carbamoyl, thiocarbamoyl, alkoxycarbonyl, carboxyaryl, halo, pseudohalo, haloalkyl and carboxamido; $R^{17}$ and $R^{18}$ are each independently selected from the group consisting of hydrogen, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy and $NR^{19}R^{20}$; $R^{19}$ and $R^{20}$ are each independently selected from alkyl, alkenyl, alkynyl, cycloalkyl, aryl, aralkyl, heteroaryl, heteroaralkyl and heterocyclyl; and $R^{30}$ and $R^{31}$ are each independently selected from alkyl, alkenyl, alkynyl, aryl, heteroaryl, aralkyl, heteroaralkyl, heterocyclyl, cycloalkyl and cycloalkylalkyl; or $R^{30}$ and $R^{31}$ together form alkylene, alkenylene, arylene, heteroarylene, aralkylene, heteroaralkylene, heterocyclylene, cycloalkylene or cycloalkylalkylene. In these embodiments, the compounds for use in the compositions and methods provided herein are preferably benzophenone derivatives that possess at least one acidic group on at least one of the phenyl rings.

The preferred compounds of this embodiment have formula (XI):

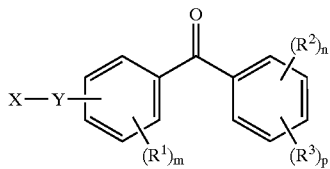

where Y-X forms an acidic group, as defined herein; and $R^1$, $R^2$, $R^3$, m, n and p are as defined above.

In more preferred embodiments, the compounds have formula (XIa):

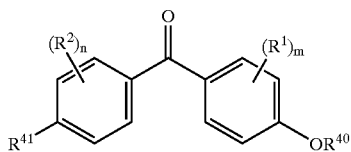

where $R^1$, $R^2{}_1$ m and n are as defined above; $R^{40}$ is hydrogen, alkyl, alkenyl, alkynyl, aryl, heteroaryl, aralkyl, heteroaralkyl, heterocyclyl, cycloalkyl or cycloalkylalkyl; and $R^{41}$ is selected from hydrogen, $NO_2$, alkoxy, $O(CH_2)_i C(O)R^{17}$, $O(CH_2)_i C(O)OR^{17}$, alkyl, alkenyl, alkynyl, aryl, heteroaryl, aralkyl, heteroaralkyl, heterocyclyl, cycloalkyl or cycloalkylalkyl, where i is an integer from 0 to 4 and $R^{17}$ is hydrogen, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy and $NR^{19}R^{20}$; $R^{19}$ and $R^{20}$ are each independently selected from alkyl, alkenyl, alkynyl, cycloalkyl, aryl, aralkyl, heteroaryl, heteroaralkyl and heterocyclyl; provided that at least one of $OR^{40}$ and $R^{41}$ is an acidic group, as defined herein.

In certain embodiments, $R^1$ is ortho to $OR^{40}$ and m is 2. In these embodiments, $R^1$ is preferably halo, pseudohalo, aryl, alkenyl, alkynyl, heteroaryl, aralkyl or heteroaralkyl, more preferably halo, aryl or alkenyl, most preferably iodo, phenyl or alkenyl. $R^{41}$ is preferably, in certain embodiments, an alkyl, alkenyl, aryl or aralkyl group substituted with an acidic group, as defined herein, preferably —COOH.

In other embodiments, $R^{41}$ is an acidic group, as defined herein, including hydroxy, carboxy, $NO_2$ and tetrazolyl. In these embodiments, the compounds preferably have formula (XIa) where $R^{41}$ is hydroxy, carboxy, $NO_2$ or tetrazolyl.

In other embodiments, X' is —C(O)— and the compound is a thiolbenzophenone derivative of formula (XIb):

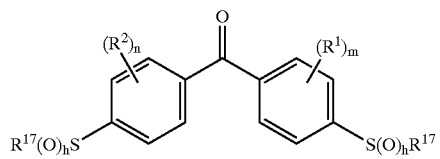

where $R^1$, $R^2$, $R^{17}$, m, n and h are as defined above, with the proviso that at least one of $S(O)_h R^{17}$ is an acidic group, as defined herein. In certain embodiments, the compounds have formula (XIb) where m and n are 2, and the $R^1$ and $R^2$ substituents are located ortho to the $S(O)_h R^{17}$ groups on each phenyl ring. In these embodiments, $R^1$ and $R^2$ are independently selected from halo, pseudohalo, aryl, alkenyl, alkynyl, heteroaryl, aralkyl or heteroaralkyl, more preferably halo, aryl or alkenyl, most preferably iodo, phenyl or alkenyl.

In certain embodiments, the compounds are benzophenone derivatives of formula (XIc):

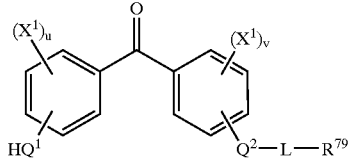

where each $X^1$ is independently selected from halo, pseudohalo, nitro, cyano, alkyl, haloalkyl, aryl or heteroaryl;

$Q^1$ is O, S, S(O), $SO_2$ or $S(O)_2O$;

$Q^2$ is O, S, S(O), $SO_2$, $S(O)_2O$ or $NR^{17}$;

L is a direct link, $CH_2$, $(CH_2)_p C(O)$, $(CH_2)_p C(O)O$ or $(CH_2)_p C(O)NR^{17}$, where p is an integer from 0 to 6, preferably 0 to 3, more preferably 0;

u is an integer from 0 to 4, preferably 0 to 2, more preferably 2;

V is an integer from 0 to 4, preferably 0 to 2, more preferably 2;

where u+v is not 0;

$R^{17}$ is as defined above;

$R^{79}$ is defined as in either (i) or (ii) below:
(i) when L is not a direct link or $CH_2$, $R^{79}$ is hydrogen, alkyl, alkenyl, alkynyl, $Q^2H$, aryl or heteroaryl; or
(ii) when L is a direct link or $CH_2$, $R^{79}$ is aryl excluding unsubstituted phenyl, heteroaryl, alkenyl or alkynyl.

In preferred embodiments, the compounds of formula (XIc) have the formula (XId):

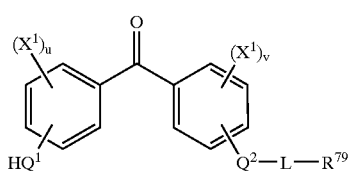

where $X^1$, $Q^1$, $Q^2$, L, u, v, $R^{17}$ and $R^{79}$ are as defined above. In the compounds of formula (XId), $Q^2$-L-$R^{79}$ is hydroxycarbonylmethoxy, 3-iodobenzyloxy, phenoxycarbonylmethoxy, benzyloxycarbonyloxy or 9-fluorenyloxy. Each $X^1$ is preferably independently halo, pseudohalo or nitro, more preferably iodo or nitro. Each $X^1$ is preferably located ortho to $Q^1$ or $Q^2$. $Q^1H$ is preferably OH.

In the above embodiments, the compounds for use in the compositions and methods provided herein are also those where X' is —$C(NR^{15})$—, —$C(OR^{30})(OR^{31})$—, —$C(SR^{30})(SR^{31})$—, and —$C(OR^{30})(SR^{31})$—, where $R^{15}$, $R^{30}$ and $R^{31}$ are as defined above. Thus, the compounds of these embodiments have the following formulae:

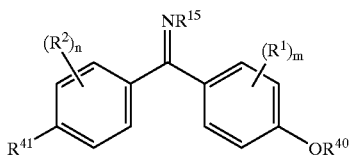

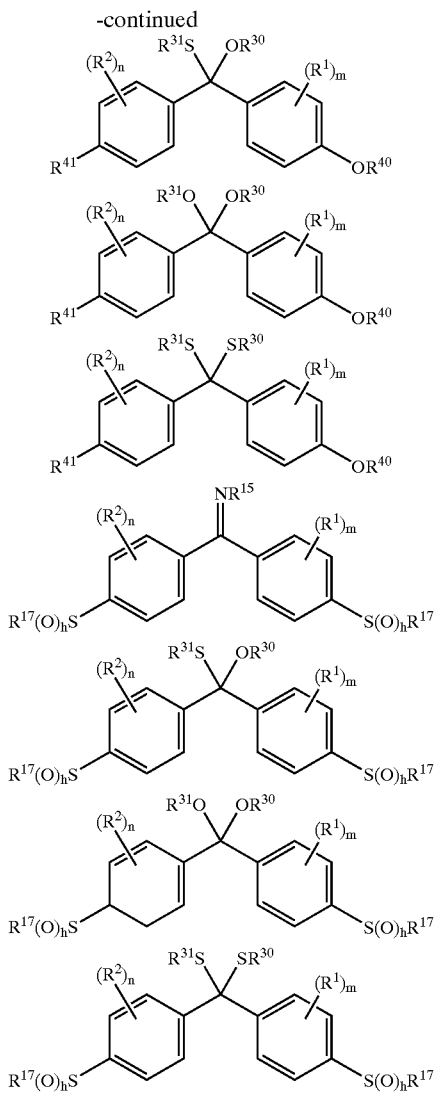

where $R^1$, $R^2$, $R^{15}$, $R^{30}$, $R^{31}$, $R^{40}$, $R^{41}$, h, m and n are as defined above.

In other embodiments, the compounds have the formula:

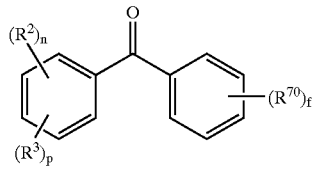

where $R^2$, $R^3$, $R^{70}$, f, n and p are selected as above.

In certain embodiments, $R^2$ is halo or pseudlohalo, particularly halo, preferably iodo and is ortho to $R^3$, which is para to the carbonyl group. In these embodiments, n is preferably 2 and p is preferably 1. $R^{70}$ is preferably halo, pseudohalo, alkoxy, aryloxy, aralkoxy, heteroaryloxy or heteroaralkoxy, more preferably halo, pseudohalo or alkoxy, particularly halo or alkoxy. In other embodiments, $R^{70}$ is fluoro, particularly when f is 1, or methoxy, particularly when f is 2.

In another embodiment, the compounds for use in the compositions and methods provided herein have the formula:

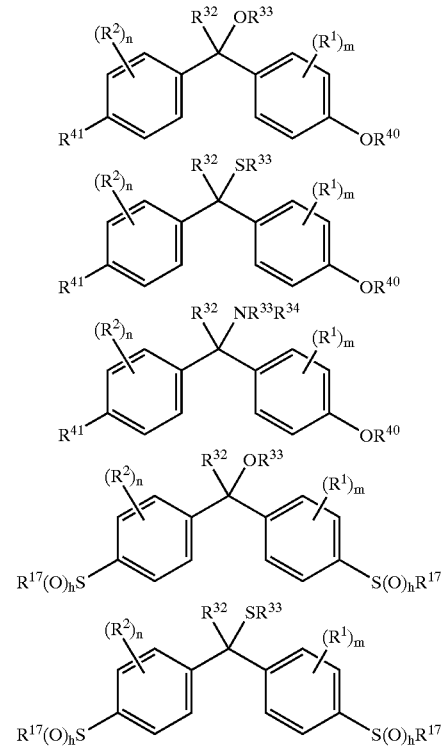

where $R^2$, $R^3$, n and p are selected as above; and $R^{75}$ is selected from alkyl, preferably $C_{3-12}$alkyl, more preferably $C_{3-8}$alkyl, alkenyl, alkynyl, aryl, heteroaryl, cycloalkyl, cycloalkenyl, aralkyl, heteroaralkyl, cycloalkylalkyl and cycloalkenylalkyl. In certain embodiments, $R^{75}$ is alkyl, alkenyl or alkynyl, preferably alkyl, more preferably $C_{3-12}$alkyl, most preferably $C_{3-6}$alkyl. In other embodiments, $R^{75}$ is propyl, butyl, pentyl or octyl, particularly n-propyl, n-butyl, n-pentyl or n-octyl. In certain embodiments, $R^{75}$ is has 5–12, preferably 7–12, more preferably 8–12, carbons in the chain. $R^2$ is halo or pseudohalo, particularly halo, preferably iodo and is ortho to $R^3$, which is para to the carbonyl group. In these embodiments, n is preferably 2 and p is preferably 1.

b. X' is —CH(OH)— or a Derivative Thereof

In other embodiments, X' is —CH(OH)— or a derivative thereof, such as —CR$^{32}$(OR$^{33}$)—, —CR$^{32}$(SR$^{33}$)— or —CR$^{32}$(NR$^{33}$R$^{34}$) where $R^{32}$, $R^{33}$ and $R^{34}$ are each independently selected from among hydrogen, alkyl, alkenyl, alkynyl, aryl, heteroaryl, aralkyl, heteroaralkyl, heterocyclyl, cycloalkyl and cycloalkylalkyl. In these embodiments, the compounds for use in the compositions and methods provided herein have the formulae:

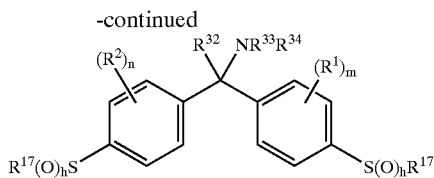

where $R^1$, $R^2$, $R^{17}$, $R^{32}$, $R^{33}$, $R^{34}$, h, m and n are as defined above.

In certain embodiments, the compounds are chosen from:

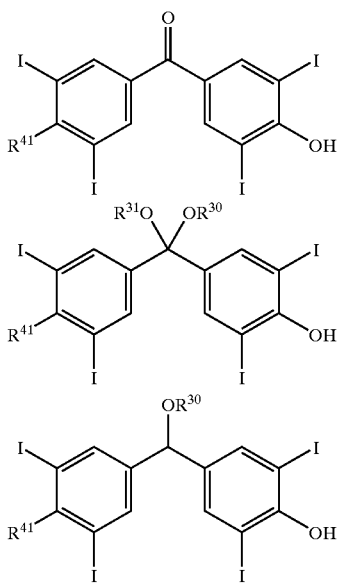

where $R^{30}$ and $R^{31}$ are selected as above; and $R^{41}$ is selected as above, and is preferably alkoxy, $O(CH_2)_iC(O)R^{17}$, $O(CH_2)_iC(O)OR^{17}$, where i is an integer from 0 to 4 and $R^{17}$ is hydrogen, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy and $NR^{19}R^{20}$; $R^{19}$ and $R^{20}$ are each independently selected from alkyl, alkenyl, alkynyl, cycloalkyl, aryl, aralkyl, heteroaryl, heteroaralkyl and heterocyclyl. $R^{41}$ is most preferably, in these embodiments, alkoxy.

In another embodiment, the compounds for use in the compositions and methods provided herein have the formula:

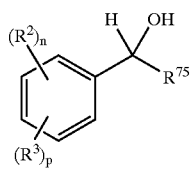

where $R^2$, $R^3$, n and p are selected as above; and $R^{75}$ is selected from alkyl, preferably $C_{3-12}$alkyl, more preferably $C_{3-8}$alkyl, alkenyl, alkynyl, aryl, heteroaryl, cycloalkyl, cycloalkenyl, aralkyl, heteroaralkyl, cycloalkylalkyl and cycloalkenylalkyl. In certain embodiments, $R^{17}$ is alkyl, alkenyl or alkynyl, preferably alkyl, more preferably $C_{3-12}$alkyl, most preferably $C_{3-8}$alkyl. In other embodiments, $R^{75}$ is propyl, butyl, pentyl or octyl, particularly n-propyl, n-butyl, n-pentyl or n-octyl, preferably n-octyl. In certain embodiments, $R^{75}$ has 5–12, preferably 7–12, more preferably 8–12, carbons in the chain. $R^2$ is halo or pseudohalo, particularly halo, preferably iodo and is ortho to $R^3$, which is para to the carbonyl group. In these embodiments, n is preferably 2 and p is preferably 1.

8. X' is —C(O)NH—

Certain of the compounds for use in the compositions and methods provided herein are of formulae (I), (II) or (III) where X' is —C(O)NH—. In preferred embodiments, the compounds are those where X' is —C(O)NH— and one of M and J is aryl, preferably phenyl. Thus, in these embodiments, the compounds have formula (XII):

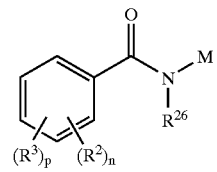

where M, $R^2$, $R^3$, n and p are as defined above; and $R^{26}$ is hydrogen or alkyl, preferably containing from 1 to 20, more preferably 1 to 10, most preferably 1 to 5 or 6 carbons in the chain.

In more preferred embodiments, n is 2; p is 1; $R^2$ is halo, pseudohalo, alkenyl, alkynyl, aryl, heteroaryl, aralkyl or heteroaralkyl, preferably halo, alkenyl or aryl, more preferably iodo, alkenyl or phenyl, and is located ortho to $R^3$; $R^3$ is preferably OH and is located para to the amido group. Thus, in these embodiments, the compounds have formula (XIIa):

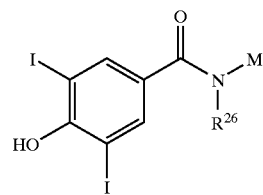

where M is as defined above; and $R^{26}$ is hydrogen or alkyl, preferably containing from 1 to 20, more preferably 1 to 10, most preferably 1 to 5 or 6 carbons in the chain.

In other embodiments, the compounds have formula (XII) or (XIIa) where M and $R^{26}$ are each independently aryl, heteroaryl, aralkyl or heteroaralkyl, particularly aralkyl or heteroaralkyl. In certain embodiments, M and $R^{26}$ are each aralkyl, preferably benzyl.

9. X' is —C(O)C(O)— or derivatives thereof

In other embodiments, the compounds provided herein for use in the compositions and methods are those of formulae (I), (II) or (III) where X' is —C(O)C(O)—. In these embodiments, one of M and J is preferably an aryl or heteroaryl group. More preferably, both of M and J are aryl or heteroaryl, most preferably aryl. The compounds of this embodiment preferably have formula (XIII):

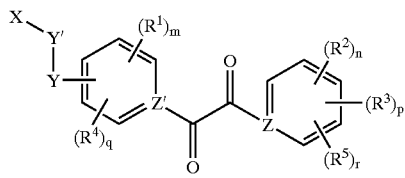

where $R^1$, $R^2$, $R^3$, $R^4$, $R^5$, X, Y, Y', Z, Z', m, n, p, q and r are as defined above.

The preferred compounds of these embodiments have formula (XIIIa):

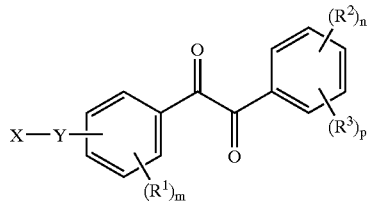

where Y-X forms an acidic group, as defined herein; and $R^1$, $R^2$, $R^3$, m, n, and p are as defined above.

In more preferred embodiments, the compounds have formula (XIIIb):

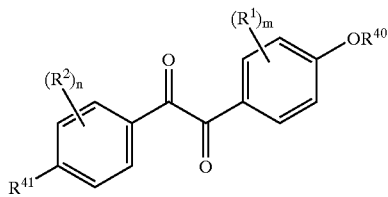

where $R^1$, $R^2$, $R^{40}$, $R^{41}$, m and n are as defined above.

In certain embodiments, $R^1$ is ortho to $OR^{40}$ and m is 2. In these embodiments, $R^1$ is preferably halo, pseudohalo, aryl, alkenyl, alkynyl, heteroaryl, aralkyl or heteroaralkyl, more preferably halo, aryl or alkenyl, most preferably iodo, phenyl or alkenyl. $R^{41}$ is preferably, in certain embodiments, an alkyl, alkenyl, aryl or aralkyl group substituted with an acidic group, as defined herein, preferably —COOH.

In other embodiments, $R^{41}$ is an acidic group, as defined herein, including hydroxy, carboxy, $NO_2$ and tetrazolyl. In these embodiments, the compounds preferably have formula (XIIIa) where $R^{41}$ is hydroxy, carboxy, $NO_2$ or tetrazolyl.

In other embodiments, X' is —C(O)C(O)— and the compound is a thiolbenzil derivative of formula (XIIIc):

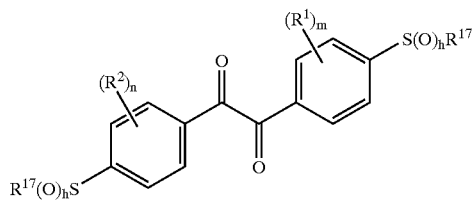

where $R^1$, $R^2$, $R^{17}$, m, n and h are as defined above, with the proviso that at least one of $S(O)_h R^{17}$ is an acidic group, as defined herein. In certain embodiments, the compounds have formula (XIIIb) where m and n are 2, and the $R^1$ and $R^2$ substituents are located ortho to the $S(O)_h R^{17}$ groups on each phenyl ring. In these embodiments, $R^1$ and $R^2$ are independently selected from halo, pseudohalo, aryl, alkenyl, alkynyl, heteroaryl, aralkyl or heteroaralkyl, more preferably halo, aryl or alkenyl, most preferably iodo, phenyl or alkenyl.

In a preferred embodiment, the compounds for use in the compositions and methods provided herein have the formula:

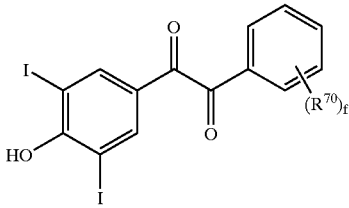

or a pharmaceutically acceptable derivative thereof, where f is an integer from 1 to 5; each $R^{70}$ is independently halo, pseudohalo, nitro, cyano, azido, hydroxy and $X^3$—$R^{18}$; or any two of $R^{70}$ that substitute adjacent carbons on the ring together form, with the carbon atoms to which they are attached, a carbocyclic, aromatic, heterocyclic or heteroaromatic ring containing from 3 to 16 members;

$X^3$ is a divalent group having any combination of the following groups: arylene, heteroarylene, cycloalkylene, $C(R^{17})_2$, —$C(R^{17})$=$C(R^{17})$—, >C=C($R^{23}$)($R^{24}$), >C($R^{23}$)($R^{24}$), —C≡C—, O, $S(A)_u$, $P(D)_v(R^{17})$, $P(D)_v(ER^{17})$, $N(R^{17})$, >$N^+(R^{23})(R^{24})$ and C(E); where u is 0, 1 or 2; v is 0, 1, 2 or 3; A is O or $NR^{17}$; D is S or O; and E is S, O or $NR^{17}$; which groups may be combined in any order;

$R^{17}$ and $R^{18}$ are each independently selected from the group consisting of hydrogen, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy and $NR^{19}R^{20}$;

$R^{19}$ and $R^{20}$ are each independently selected from hydrogen, alkyl, alkenyl, alkynyl, cycloalkyl, aryl, aralkyl, heteroaryl, heteroaralkyl and heterocyclyl;

wherein the aryl, heteroaryl, heterocyclyl and cycloalkyl substituents of $R^{70}$ are unsubstituted or substituted with halo, pseudohalo, cyano, azido, $NO_2$, $NR^{17}R^{18}$, $SiR^{17}R^{18}R^{25}$, $COR^{17}$, $COOR^{17}$, $CONR^{17}R^{18}$, $C_t$alkyl-L-, $C_q$alkenyl-L-, $C_q$alkynyl-L-, $C_s$aryl-L- or $C_s$heteroaryl-L-, where L is a direct link, amido, carboxy, carbonyl, sulfonyl, ureido, sulfonamido, hydrazinyl, hydrazido, semicarbazido, carbazato, thiocarbazato, isothiocarbazato or sulfonylhydrazido;

$R^{25}$ is a monovalent group selected from hydrogen, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy and $NR^{19}R^{20}$;

each q is independently selected to be an integer from 2 to 20; each t is independently selected to be an integer from 1 to 20; each s is independently selected to be an integer from 5 to 16;

$R^{23}$ and $R^{24}$ are selected from (i) or (ii) as follows:
(i) $R^{23}$ and $R^{24}$ are independently selected from the group consisting of hydrogen, alkyl, alkenyl, alkynyl, cycloalkyl, aryl and heteroaryl; or (ii) $R^{23}$ and $R^{24}$ together form alkylene, alkenylene or cycloalkylene;

$R^{17}$, $R^{18}$, $R^{19}$, $R^{20}$, $R^{23}$, $R^{24}$ and $R^{25}$ may be substituted with one or more substituents each independently selected from $Z^2$, wherein $Z^2$ is selected from alkyl, alkenyl, alkynyl, aryl, cycloalkyl, cycloalkenyl, hydroxy, $S(O)_h R^{17}$, $NR^{17}R^{18}$, $COOR^{17}$, $COR^{17}$, $CONR^{17}R^{18}$, $OC(O)NR^{17}R^{18}$, $N(R^{17})C(O)R^{18}$, alkoxy, aryloxy, heteroaryl, heterocyclyl, heteroaryloxy, heterocyclyloxy, aralkyl, aralkenyl, aralkynyl, heteroaralkyl, heteroaralkenyl, heteroaralkynyl, aralkoxy, heteroaralkoxy, alkoxycarbonyl, carbamoyl, thiocarbamoyl, alkoxycarbonyl, carboxyaryl, halo, pseudohalo, haloalkyl and carboxamido.

In the above embodiments, the compounds for use in the compositions and methods provided herein are also those where X' has two of the following groups: —C(O)—, —C($NR^{15}$)—, —C($OR^{30}$)($OR^{31}$)—, —C($SR^{30}$)($SR^{31}$)—, —C($OR^{30}$)($SR^{31}$)—, —$CR^{32}$($OR^{33}$)—, —$CR^{32}$($SR^{33}$)— or —$CR^{32}$($NR^{33}R^{34}$), where $R^{15}$, $R^{30}$, $R^{31}$, $R^{32}$, $R^{33}$ and $R^{34}$ are as defined above. Thus, in these embodiments, the compounds include benzil imines, diimines, ketals, diketals, thioketals and hemiketals, and reduced derivatives thereof.

10. Compounds Where M or J is Alkyl

Also contemplated for use in the compositions and methods provided herein are compounds of formula M-X'-J where X' and one of M and J are selected as described above; and the other of M and J is alkyl, alkenyl or alkynyl, including straight and branched chains, or is cycloalkyl or cycloalkylalkyl. In these embodiments, the alkyl, alkenyl, alkynyl, cycloalkyl or cycloalkylalkyl group preferably contains from 2 to 50, preferably from 3 or 4 to 40, more preferably from 5 or 6 to 25, most preferably from 5 or 6 to 20 carbons in the chain(s) or ring(s). The alkyl, alkenyl, alkynyl, cycloalkyl or cycloalkylalkyl groups are unsubsituted or substituted with an acidic group, as defined herein, preferably a carboxylic acid group or derivative thereof of formula —$COR^{15}$, where $R^{51}$ is hydrogen, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy or $NR^{19}R^{20}$; and $R^{19}$ and $R^{20}$ are each independently selected from alkyl, alkenyl, alkynyl, cycloalkyl, aryl, aralkyl, heteroaryl, heteroaralkyl and heterocyclyl.

In certain of these embodiments, the compounds have formula (XIV):

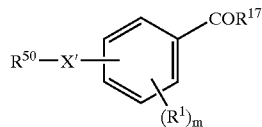

where $R^1$, $R^{17}$, X' and m are selected as described above; and $R^{50}$ is selected from alkyl, alkenyl or alkynyl, including straight and branched chains, or is cycloalkyl or cycloalkylalkyl, where the alkyl, alkenyl, alkynyl, cycloalkyl or cycloalkylalkyl group contain from 2 to 50, preferably from 3 or 4 to 40, more preferably from 5 or 6 to 25, most preferably from 5 or 6 to 12 carbons in the chain(s) or ring(s). The alkyl, alkenyl, alkynyl, cycloalkyl or cycloalkylalkyl groups are unsubsituted or substituted with an acidic group, as defined herein, preferably a carboxylic acid group or derivative thereof of formula —$COR^{60}$, where $R^{60}$ is hydrogen, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy or $NR^{19}R^{20}$; and $R^{19}$ and $R^{20}$ are each independently selected from alkyl, alkenyl, alkynyl, cycloalkyl, aryl, aralkyl, heteroaryl, heteroaralkyl and heterocyclyl.

In particular embodiments, m is 2 and $R^1$ is located ortho to X'-$R^{50}$, which is located para to $COR^{17}$. $R^1$ is, in these embodiments, preferably halo, pseudohalo, alkyl, alkenyl, alkynyl, aryl, heteroaryl, aralkyl or heteroaralkyl, more preferably halo, pseudohalo, alkenyl, alkynyl, aryl or heteroaryl, particularly halo, alkenyl or aryl, most preferably iodo, alkenyl or phenyl. X' is preferably O or $(CH_2)_d O$.

In the above embodiments, $R^{17}$, $R^{50}$ and $R^{60}$ are selected such that the compound has at least one acidic group, as defined herein.

In certain embodiments, $R^{50}$ is selected from the following groups:

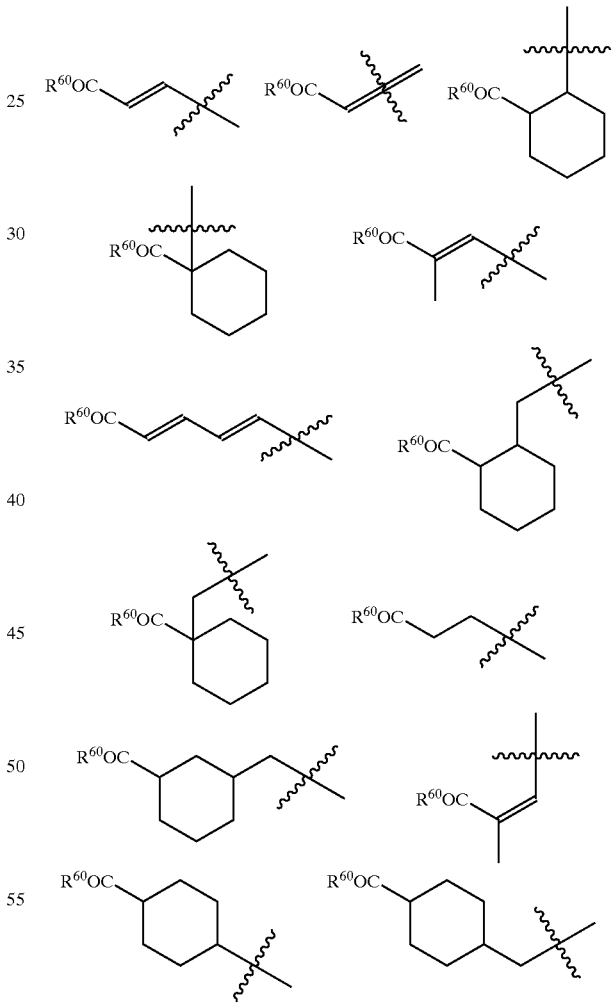

In other embodiments, the compounds have formula (XIV) where $R^{50}$ is cycloalkylalkyl; X' is $CH_2O$; and $R^1$, $R^{17}$ and m are selected as above. In particular, $R^{17}$ is OH, $R^1$ is iodo, and m is 2. In these embodiments, $R^{50}$ is preferably cyclohexylmethyl.

In certain embodiments herein, the compounds have formula (XIV), with the proviso that when $R^{17}$ is OH, X' is CH$_2$O, R$^1$ is iodo, and m is 2; then R$^{50}$ is not cyclohexyl. In other embodiments, the compounds have formula (XIV), with the proviso that when X' is CH$_2$O, then R$^{50}$ is not cyclohexyl. In further embodiments, the compounds have formula (XIV), with the proviso that when X' is CH$_2$O and R$^{17}$ is OH, then R$^{50}$ is not cyclohexyl. In another embodiment, the compounds have formula (XIV), with the proviso that the compound is not 4-cyclohexylmethoxy-3,5-diiodobenzoic acid.

11. X' is —C(O)OCH$_2$—

In other embodiments, the compounds are of formulae (I), (II) or (III), where X' is —C(O)OCH$_2$—. In a preferred embodiment, the compounds have the formula:

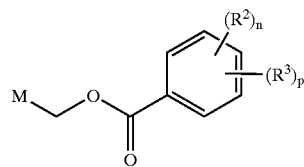

where M, R$^2$, R$^3$, n and p are as defined above. In more preferred embodiments, the compounds have the formula:

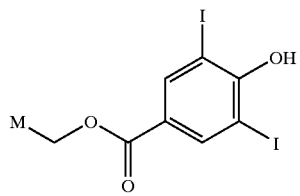

where M is selected as described above.

In other embodiments herein, the compounds have the formula:

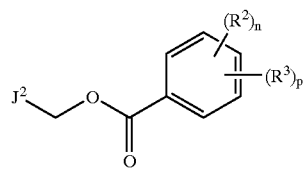

where J$^2$ is a monocyclic or polycyclic cycloalkyl, aryl, heteroaryl, heterocyclyl, or two or more fused or bridged cycloalkyl, heterocyclyl, aryl or heteroaryl rings, or alkyl, alkenyl, alkynyl or cycloalkyl. In these embodiments, R$^2$ is preferably iodo, n is an integer from 1 to 4, R$^3$ is preferably OH and p is 1. Thus, in preferred embodiments, the compounds have the formula:

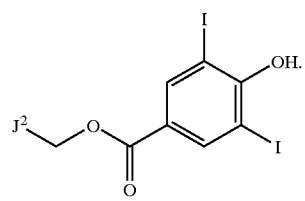

J$^2$ is preferably monocyclic aryl or heteroaryl, more preferably 3-benzyloxyphenyl or 2-iodophenyl.

12. X' is SO$_2$

In certain embodiments, the compounds for use in the compositions and methods provided herein are those where X' is SO$_2$. In preferred embodiments, the compounds are sulfone derivatives of formulae:

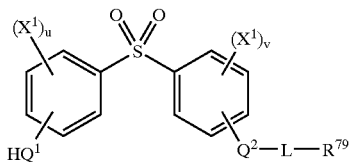

where each X$^1$ is independently selected from halo, pseudohalo, nitro, cyano, alkyl, haloalkyl, aryl or heteroaryl;

Q$^1$ is O, S, S(O), SO$_2$ or S(O)$_2$O;

Q$^2$ is O, S, S(O), SO$_2$, S(O)$_2$O or NR$^{17}$;

L is a direct link, CH$_2$, (CH$_2$)$_p$C(O), (CH$_2$)$_p$C(O)O or (CH$_2$)$_p$C(O)NR$^{17}$, where p is an integer from 0 to 6, preferably 0 to 3, more preferably 0;

u is an integer from 0 to 4, preferably 0 to 2, more preferably 2;

v is an integer from 0 to 4, preferably 0 to 2, more preferably 2;

where u+v is not 0;

R$^{17}$ is as defined above;

R$^{79}$ is defined as in either (i) or (ii) below:
(i) when L is not a direct link or CH$_2$, R$^{79}$ is hydrogen, alkenyl, alkynyl, Q$^2$H, aryl or heteroaryl; or
(ii) when L is a direct link or CH$_2$, R$^{79}$ is aryl, heteroaryl, alkenyl or alkynyl.

In more preferred embodiments, the compounds have the formula:

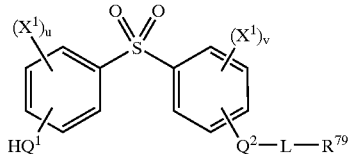

where X', Q$^1$, Q$^2$$_1$, L, u, v, R$^{17}$ and R$^{79}$ are as defined above. In the compounds of formula (XId), Q$^2$-L-R$^{79}$ is hydroxycarbonylmethoxy, 3-iodobenzyloxy, phenoxycarbonylmethoxy, benzyloxycarbonyloxy or 9-fluorenyloxy. Each X' is preferably independently halo, pseudohalo or nitro, more preferably iodo or nitro. Each X$^1$ is preferably located ortho to Q$^1$ or Q$^2$. Q$^1$H is preferably OH.

13. X' is —C(O)CH$_2$O—

In certain embodiments, the compounds for use in the compositions and methods provided herein are those where X' is —C(O)CH$_2$O—. In preferred embodiments, the compounds are benzoylalkoxy derivatives of formula:

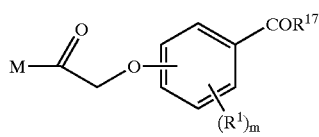

where R$^1$, R$^{17}$, M and m are as defined above, provided that COR$^{17}$ is an acidic group, as defined herein.

In other embodiments herein, R$^{17}$ is OH and the compounds are benzoic acid derivatives of formula:

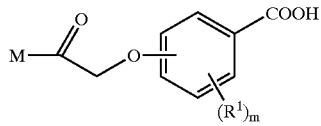

where $R^1$, M and m are as defined above. In other embodiments, M is aryl or heteroaryl, particularly aryl including phenyl, and the compounds have the formula:

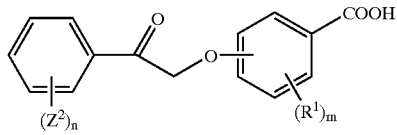

where $R^1$, $Z^2$, n and m are as defined above. $R^1$ is, in certain embodiments, halo or pseudohalo; and $Z^2$ is halo, pseudohalo, or alkylenedioxy. In other embodiments, $R^1$ is halo, particularly iodo; and $Z^2$ is halo, particularly bromo, or any two $Z^2$ groups that substitute adjacent carbons on the ring may form propylenedioxy, ethylenedioxy or methylenedioxy, particularly propylenedioxy.

In another embodiment, the group M—C(O)CH$_2$O— is in the para position relative to the COR$^{17}$ group and the compounds have the

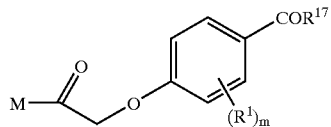

where $R^1$, $R^{17}$, M and m are as defined above, provided that COR$^{17}$ is an acidic group, as defined herein.

In other embodiments, the compounds have the formula:

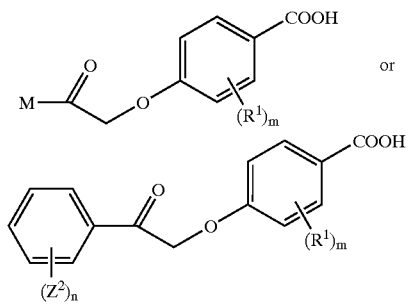

where $R^1$, $Z^2$, M, n and m are as defined above.

In certain embodiments, m is 2 and $R^1$ is halo or pseudohalo, particularly halo, more particularly iodo. $R^1$ is, in other embodiments, positioned ortho to the —C(O)CH$_2$O— group.

14. X' is —CH$_2$—

In other embodiments, the compounds for use in the compositions and methods provided herein are those where X' is —CH$_2$—. In these embodiments, the compounds have the formula:

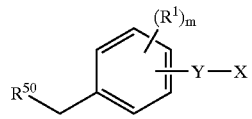

where $R^1$, $R^{50}$, X, Y and m are selected as above.

$R^{50}$, in certain embodiments, is alkyl, alkenyl or alkynyl, including straight and branched chains, or is cycloalkyl or cycloalkylalkyl, where the alkyl, alkenyl, alkynyl, cycloalkyl or cycloalkylalkyl group contain from 2 to 50, preferably from 3 or 4 to 40, more preferably from 5 or 6 to 25, most preferably from 5 or 6 to 12 carbons in the chain(s) or ring(s). In particular, $R^{50}$ is a straight chain alkyl group having from 5 or 6 to 12 carbons, particularly 5 to 9 carbons. $R^{50}$ is, in certain embodiments, n-heptyl.

In these embodiments, p is preferably 1 and n is preferably 2. $R^1$ is preferably located ortho to X-Y, and is in particular halo or pseudohalo, preferably halo, particularly iodo. Thus, the compounds, in these embodiments, have the formula:

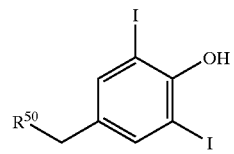

where $R^{50}$ is selected as above.

15. X' is —CH═

In certain embodiments herein, the compounds for use in the compositions and methods provided are those where X' is —CH═. In these embodiments, one of M and J is a divalent group, including an alkylidene, cycloalkylidene or heterocyclylidene group. Thus, in these embodiments, the compounds have the formula:

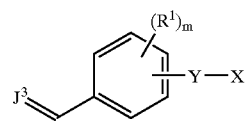

where $R^1$, Y, X and m are as defined above; and $J^3$ is a divalent group including alkylidene, cycloalkylidene and heterocyclylidene. In certain embodiments, $J^3$ is alkylidene or heterocyclylidene. In other embodiments, $J^3$ is methoxycarbonylmethylidene (i.e., ═CHCOOMe) or 1,3-dihydroindol-2-on-3-ylidene.

In another embodiment, $R^1$ is halo or pseudohalo, preferably halo, more preferably iodo, and is located ortho to Y-X. Y-X is preferably OH, and the compounds have the formula:

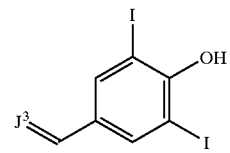

where $J^3$ is selected as above.

16. X' is a Direct Link

In another embodiment, X' is a direct link and the compounds for use in the compositions and methods provided herein have the formula M-J. In these embodiments, M and J are each independently selected from cycloalkyl, heterocyclyl, aryl and heteroaryl, with the proviso that at least one of M and J is substituted with at least one acidic group; M and J are each independently unsubstituted or substituted with one or more substituents independently selected from halo, pseudohalo, nitro, cyano, azido, $S(O)_h$ $R^{17}$, $NR^{17}R^{18}$, $O(CH_2)_tC(O)R^{17}$, $O(CH_2)_tC(O)OR^{17}$, $COR^{17}$, $COOR^{17}$, $CONR^{17}R^{18}$, hydroxy, alkoxy, aryloxy, heteroaryloxy, aralkoxy, heteroaralkoxy, heterocyclyloxy, aryl, aralkyl, heteroaryl, heteroaralkyl, heterocyclyl, heterocyclylalkyl, alkyl, alkenyl, alkynyl, haloalkyl, haloalkoxy or cycloalkyl; h is 0, 1 or 2; i is an integer from 0 to 4; where the aryl, heteroaryl, heterocyclyl and cycloalkyl substituents of M and J are unsubstituted or substituted with halo, pseudohalo, cyano, azido, $NO_2$, $NR^{17}R^{18}$, $SiR^{17}R^{18}R^{19}$, $COR^{17}$, $COOR^{17}$, $CONR^{17}R^{18}$, $C_q$alkyl-L-, $C_q$alkenyl-L-, $C_q$alkynyl-L-, $C_s$aryl-L- or $C_s$heteroaryl-L-, where L is a direct link, amido, carboxy, carbonyl, sulfonyl, ureido, sulfonamido, hydrazinyl, hydrazido, semicarbazido, carbazato, thiocarbazato, isothiocarbazato or sulfonylhydrazido; $R^{17}$ and $R^{18}$ are each independently selected from the group consisting of hydrogen, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy and $NR^{19}R^{20}$; $R^{19}$ and $R^{20}$ are each independently selected from alkyl, alkenyl, alkynyl, cycloalkyl, aryl, aralkyl, heteroaryl, heteroaralkyl and heterocyclyl; each q is independently selected to be an integer from 2 to 20; each t is independently selected to be an integer from 1 to 20; and each s is independently selected to be an integer from 5 to 16.

In more preferred embodiments, the compounds are biphenyl derivatives that have formula:

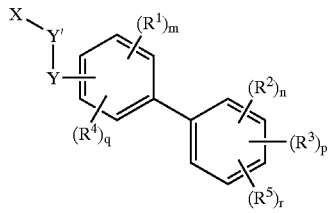

where $R^1$, $R^2$, $R^3$, $R^4$, $R^{15}$, Y, Y', X, m, n, p, q and r are as defined above. In particular, Y-Y'-X forms an acidic group, as defined herein, and is preferably OH, COOH, $SO_3H$ or $P(O)(OH)_2$, more preferably OH or COOH.

In certain embodiments, $R^2$ is halo or pseudohalo, preferably halo, more preferably iodo, and is located ortho to $R^3$. $R^3$ is preferably OH, and the compounds have the formula:

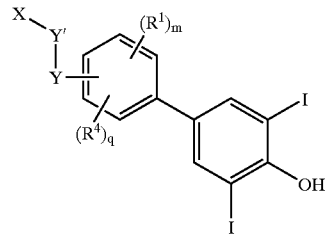

where $R^1$, $R^4$, X, Y, Y', m and q are selected as above.

In certain embodiments, the compounds have either of the formulae:

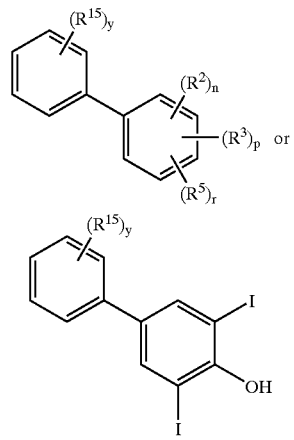

where $R^2$, $R^3$, $R^5$, $R^{15}$, n, p and r are selected as above; and y is an integer from 0 to 5, in particular, y is 0, 1 or 2, particularly 1. $R^{15}$ is selected, in other embodiments, from halo, pseudohalo, nitro and isothiocyanato. In certain embodiments, $R^{15}$ is nitro or cyano.

17. X' is heterocyclylene-$(CH_2)_z$—,

In other embodiments, X' is heterocyclylene-$(CH_2)_z$—, where z is an integer from 0 to 6, preferably 1, 2 or 3, particularly 1. Thus, in these embodiments, the compounds have the formula M-heterocyclylene-$(CH_2)_z$— J, where M and J are selected as above.

In one embodiment, M and J are each independently aryl or heteroaryl groups, particuarly aryl groups, more particularly phenyl groups, and the compounds have the formula:

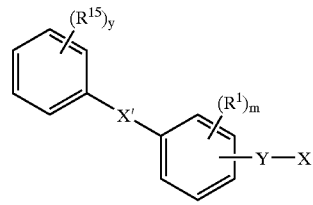

where $R^1$, X, Y, $R^{15}$, y and m are selected as above; and X' is -heterocyclylene-$(CH_2)_z$—, where z is an integer from 0 to 6, preferably 1, 2 or 3, particularly 1.

In another embodiment, $R^1$ is halo or pseudohalo, preferably halo, more preferably iodo, and is located ortho to Y-X. Y-X is preferably OH, and the compounds have the formula:

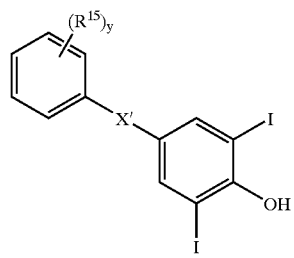

where $R^{15}$ and y are selected as above; and X' is -heterocyclylene-$(CH_2)_z$—, where z is an integer from 0 to 6, preferably 1, 2 or 3, particularly 1.

In certain embodiments, y is 0 and X' is -heterocyclylene—$CH_2$—, particularly tetrazolylene-$CH_2$—, more particularly 1,3-tetrazolylene-$CH_2$—.

18. X' is —CH=CH— or —C≡C—

In other embodiments, X' is —CH=CH— or —C≡C—, particularly —C≡C—. Thus, in these embodiments, the compounds have the formula M—CH=CH—J or M—C≡C—J, particularly M—C≡C—J, where M and J are selected as above.

In one embodiment, M and J are each independently aryl or heteroaryl groups, particuarly aryl groups, more particularly phenyl groups, and the compounds have the formula:

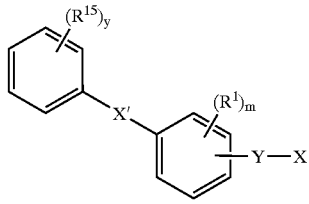

where $R^1$, X, Y, $R^{15}$, V and m are selected as above; and X' is —CH=CH— or —C≡C—, particularly —C≡C—.

In another embodiment, $R^1$ is halo or pseudohalo, preferably halo, more preferably iodo, and is located ortho to Y-X. Y-X is preferably OH, and the compounds have the formula:

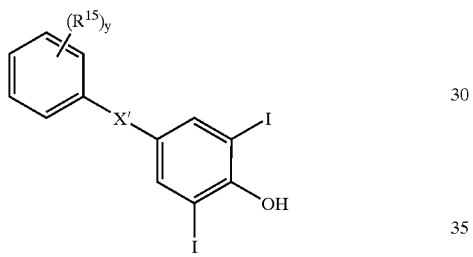

where $R^{15}$ and y are selected as above; and X' is —CH=CH— or —C≡C—, particularly —C≡C—.

In certain embodiments, y is 0 and X' is —CH=CH— or —C≡C—, particularly —C≡C—.

19. Other Compounds

Other compounds contemplated herein for use in the compositions and methods include those of formula (XV):

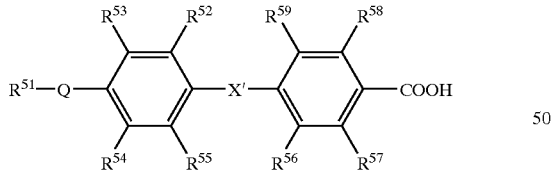

or a pharmaceutically acceptable derivative thereof, where X' is O, S, CH$_2$, carboxy or absent; Q is O or S; $R^{51}$ is methyl or ethyl; $R^{52}$, $R^{53}$, $R^{54}$ and $R^{55}$ are each independently selected from the group consisting of H, alkyl, alkenyl, alkynyl, hydroxy, alkoxy and halo; and $R^{56}$, $R^{57}$, $R^{58}$ and $R^{59}$ are each independently selected from the group consisting of H, alkyl, alkenyl, alkynyl, hydroxy, alkoxy, halo, NO$_2$ and NH$_2$.

Compounds of this embodiment include those where $R^{56}$ and $R^{59}$ are both iodo. Presently preferred compounds of this embodiment include 3,5-diiodo-4-(4'-ethoxyphenoxy) benzoic acid, 3,5-diiodo-4-(4'-propoxyphenoxy)benzoic acid, 3,5-diiodo-4-(4'-butoxyphenoxy)benzoic acid, 3,5-diiodo-4-(4'-hydroxyphenoxy)benzoic acid, 3,5-diiodo-4-(4'-iodophenoxy)benzoic acid, 3,5-diiodo-4-(3'-methoxyphenoxy)benzoic acid, 3,5-diiodo-4-(2'-chloro-4'-methoxyphenoxy)benzoic acid, 3,5-diiodo-4-(3',4'-dimethoxyphenoxy)benzoic acid and 3,5-diiodo-4-(4'-trifluoromethoxyphenoxy)benzoic acid.

20. Preferred Compounds

Presently preferred compounds for use in the compositions and/or methods provided herein include benzophenones, benzils, benzyl ethers, benzoate ester and amides, particularly those listed in FIG. 1 that have an IC$_{50}$ less than about 100 µM (see, the Examples for assay conditions). Exemplary synthetic schemes and syntheses are set forth in the examples. Of the compounds set forth in FIG. 1, those with an IC$_{50}$ less than about 100 µM are presently preferred.

Other compounds include, but are not limited to, thyroxine analogs; and

5-[4,5-dihydro-5-oxo-3-[(1-oxooctadecyl)amino]-1 H-pyrazol-1-yl]-2-phenoxybenzensulfonic acid, i.e.,

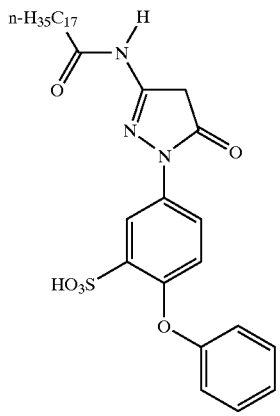

5-{4-[(2-chloro-4-hydroxyphenyl)azo]-3-octadecanamido-5-oxo-pyrazolin-1-yl}-2-phenoxybenzenesulfonic acid, i.e.,

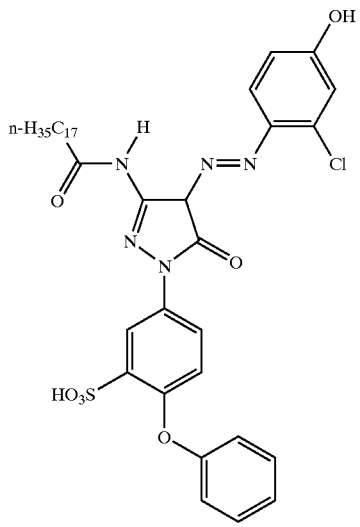

sodium 5-[4,5-dihydro-5-oxo-3-[(1-oxooctadecyl) amino]-1H-pyrazol-1-yl]-2-phenoxybenzensulfonate, i.e., 1-(3-sulfo-4-phenoxy)phenyl-3-heptadecylpyrazolin-5-one, i.e.,

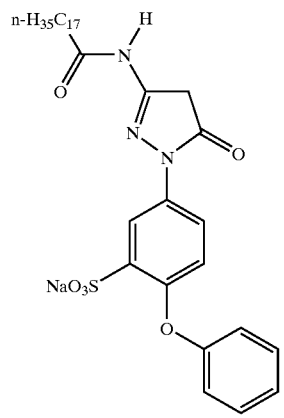

sodium 4-[4-(decyloxysulfonyl)phenyl]oxybenzenesulfonate, i.e.,

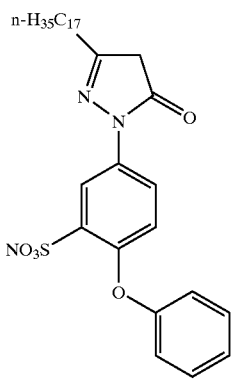

5-nitro-2-(4-(1,1,3,3-tetramethylbutyl)phenoxy)benzenesulfonic acid, i.e.,

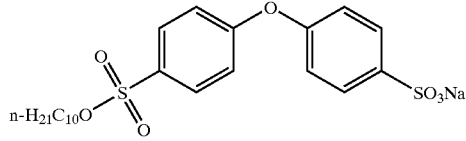

1-hexadecanesulfonic (1-methyl-6-sulfo-(2-(4-tolyloxy)phenyl)-4-quinolylidene)hydrazide, i.e.,

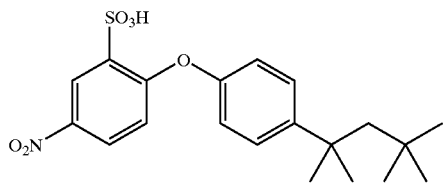

3,3′,5,5′-tetraiodothyropropionic acid, i.e.,

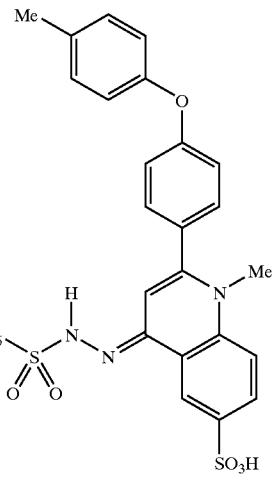

3,3′,5-triiodothyroacetic acid, i.e.,

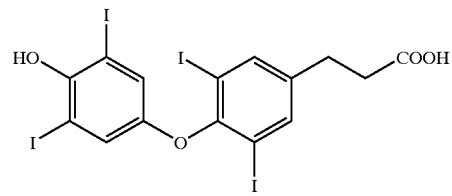

3,3′,5,5′-tetraiodothyroacetic acid, i.e.,

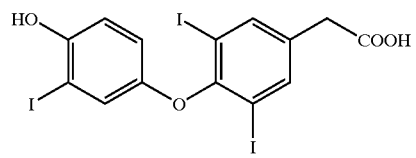

3,3′,5-triiodothyropropionic acid, i.e.,

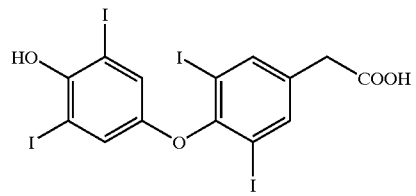

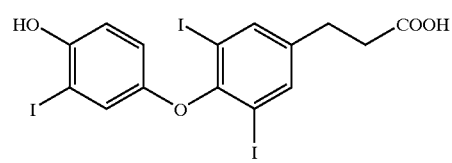

L-3,3',5'-triiodothyronine, i.e.,

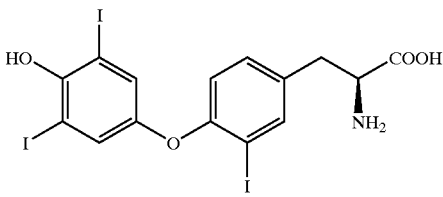

3,5-diiodothyropropionic acid, i.e.,

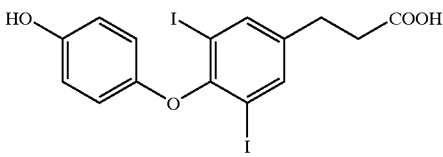

and L-thyroxine, i.e.,

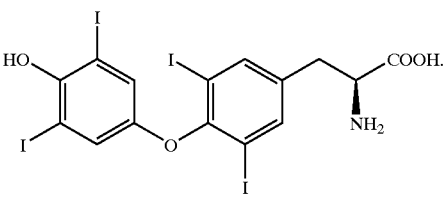

Other exemplary compounds for use in the compositions and methods provided herein include:

3,5-diiodo-4-(3-bromobenzyloxy)benzoic acid, i.e.,

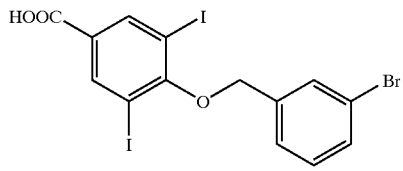

and 3-(3,5-diiodo-4-(3-iodobenzyloxy)phenyl)propionic acid, i.e.,

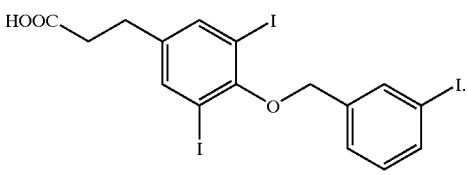

Other compounds for use in the compositions and methods provided herein include 3,5-diiodo-4-(3-iodobenzyloxy)benzoic acid; 3,5-diiodo-4-(4-iodobenzyloxy)benzoic acid; 3,5-diiodo-4-(benzyloxy)benzoic acid; 3,5-diiodo-4-(2-bromobenzyloxy)benzoic acid; 3,5-diiodo-4-(4-bromobenzyloxy)benzoic acid; 3,5-diiodo-4-(2-methylbenzyloxy)benzoic acid; 3,5-diiodo-4-(3-methylbenzyloxy)benzoic acid; 3,5-diiodo-4-(4-methylbenzyloxy)benzoic acid; 3,5-diiodo-4-(4-tert-butylbenzyloxy)benzoic acid; 3,5-diiodo-4-(naphth-2-ylmethoxy)benzoic acid; 3,5-diiodo-4-(biphen-2-yloxy)benzoic acid; 3,5-diiodo-4-(3-methoxybenzyloxy)benzoic acid; 3,5-diiodo-4-(3-trifluoromethylbenzyloxy)benzoic acid; 3,5-diiodo-4-(3-trifluoromethoxybenzyloxy)benzoic acid; 3,5-diiodo-4-(3-fluorobenzyloxy)benzoic acid; 3,5-diiodo-4-(2,3,4,5,6-pentafluorophenyl-methoxy)benzoic acid; 3-(3,5-diiodo-4-(4-iodobenzyloxy)phenyl)propionic acid; 3-(3,5-diiodo-4-(benzyloxy)phenyl)propionic acid; 3-(3,5-diiodo-4-(3-bromobenzyloxy)phenyl)propionic acid; 3,5-dibromo-4-(3-iodobenzyloxy)-benzoic acid; 3,5-dichloro-4-(3-iodobenzyloxy)benzoic acid; and 3-(3,5-diiodo-4-(4-bromobenzyloxy)phenyl)propionic acid.

Other presently preferred compounds include (4-hydroxy-3-iodo-5-nitrophenyl)-phenyl-methanone; 3,5-diiodo-4-(3-iodo-benzyloxy)-benzoic acid; 3,5-diiodo-4(4-Iodo-benzyloxy)-benzoic acid; 4-benzyloxy-3,5-diiodo-benzoic acid; 3,5-diiodo-4-(2-bromo-benzyloxy)-benzoic acid; 3,5-diiodo-4-(3-bromo-benzyloxy)-benzoic acid; 3,5-diiodo-4-(4-bromo-benzyloxy)-benzoic acid; 3,5-diiodo-4-(2-methyl-benzyloxy)-benzoic acid; 3,5-diiodo-4-(3-methyl-benzyloxy)-benzoic acid; 3,5-diiodo-4-(4-methyl-benzyloxy)-benzoic acid; 4-(4-tert-butyl-benzyloxy)-3,5-diiodo-benzoic acid; 3,5-diiodo-4-(naphthalen-2-ylmethoxy)-benzoic acid; 4-(biphenyl-2-ylmethoxy)-3,5-diiodo-benzoic acid; 3,5-diiodo-4-(3-methoxy-benzyloxy)-benzoic acid; 3,5-diiodo-4-(3-trifluoromethyl-benzyloxy)-benzoic acid; 3,5-diiodo-(3-trifluoromethoxy-benzyloxy)-benzoic acid; 4-(3-fluoro-benzyloxy)-3,5-diiodo-benzoic acid; 3,5-diiodo-4-pentafluorophenylmethoxy-benzoic acid; 3,5-dibromo-4-(3-iodo-benzyloxy)-benzoic acid; 3,5-dichloro-4-(3-iodo-benzyloxy)-benzoic acid; 4-(4-tert-butyl-benzyloxy)-3,5-dimethoxy-benzoic acid; 3-[3,5-diiodo-4-(3-iodo-benzyloxy)-phenyl]-propionic acid; 3-[3,5-diiodo-4-(4-iodo-benzyloxy)-phenyl]-propionic acid; 3-(4-benzyloxy-3,5-diiodo-phenyl)-propionic acid; 3-[4-(3-bromo-benzyloxy)-3,5-diiodo-phenyl]-propionic acid; 3-[4-(4-bromo-benzyloxy)-3,5-diiodo-phenyl]-propionic acid; 3,5-dibromo-4-(4-tert-butyl-benzyloxy)-benzoic acid; [3,5-diiodo-4-(3-iodo-benzyloxy)-phenyl]-acetic acid; [3,5-diiodo-4-(4-iodo-benzyloxy)-phenyl]-acetic acid; (4-benzyloxy-3,5-diiodo-phenyl)-acetic acid; [4-(3-bromo-benzyloxy)-3,5-diiodo-phenyl]-acetic acid; 4-(2-nitro-benzyloxy)-3,5-diiodo-benzoic acid; 4-(3-nitro-benzyloxy)-3,5-diiodo-benzoic acid; 4-(4-nitro-benzyloxy)-3,5-diiodo-benzoic acid; 4-(2-cyano-benzyloxy)-3,5-diiodo-benzoic acid; 4-(3-cyano-benzyloxy)-3,5-diiodo-benzoic acid; 4-(4-cyano-benzyloxy)-3,5-diiodo-benzoic acid; (4-hydroxy-3,5-diiodo-phenyl)-phenyl-methanone; (4-benzoyl-2,6-diiodo-phenoxy)-acetic acid; 4-hydroxy-3,5-diiodo-benzoic acid 2-iodo-benzyl ester; 2-acetylamino-3-[3,5-diiodo-4-(3-iodo-benzyloxy)-phenyl]-propionic acid; bis-(4-hydroxy-3,5-diiodophenyl)-methanone; 4-(2-fluorobenzyloxy)-3,5-diiodo-benzoic acid; 4-(4-fluorobenzyloxy)-3,5-diiodobenzoic acid; 4-(2-chlorobenzyloxy)-3,5-diiodobenzoic acid; 4-(3-chlorobenzyloxy)-3,5-diiodobenzoic acid; [4-(4-hydroxy-3,5-diiodo-benzoyl)-2,6-diiodo-phenoxy]-aceticacid benzyl ester; 4-(4-chlorobenzyloxy)-3,5-diiodobenzoic acid; [4-[(6,7-dihydro-5,5,8,8-tetramethyl)naphthyl-2-methoxy]-3,5-diiodobenzoic acid; 4-(1,6-dichloro-benzyloxy)-3,5-diiodobenzoic acid; 4-(1,6-difluoro-benzyloxy)-3,5-diiodobenzoic acid; 4-[4-(trifluoromethoxy)-benzyloxy]-3,5-diiodobenzoic acid; 4-[2-(trifluoromethyl)-benzyloxy]-3,5-diiodobenzoic acid; 4-[4-(trifluoromethyl)-benzyloxy]-3,5-diiodobenzoic acid; 4-[(2-fluoro-4-bromo)benzyloxy]-3,5-diiodobenzoic acid; 4-(2-iodo)benzyloxy-3,5-diiodobenzoic acid; 4-(3-benzoyl)benzyloxy-3,5-diiodobenzoic acid; 4-(2-methoxy-5-nitro)benzyloxy-3,5-diiodobenzoic acid; 4-(3,5-dimethoxy)benzyloxy-3,5-diiodobenzoic acid; [4-(4-hydroxy-3,5-diiodo-benzoyl)-2,6-diiodo-phenoxy]-acetic acid; 4-(3-methylnaphthyl-2-methoxy)-3,5-diiodobenzoic acid; 4-[N-

[(2-benzoyl)phenyl]-methoxyamidyl]-3,5-diiodobenzoic acid; 4-[4-(trifluoromethyl)thio]-benzyloxy-3,5-diiodobenzoic acid; 4-[2-(trifluoromethyl)thio]-benzyloxy-3,5-diiodobenzoic acid; [4-(4-carboxymethyoxy-3,5-diiodobenzoyl)-2,6-diiodo-phenoxy]-acetic acid; 4-(adamantyl-1-acetoxy)-3,5-diiodobenzoic acid; 4-(4-chloro)benzyloxy-3,5-dichlorobenzoic acid; 4-(naphthyl-2-methoxy)-3,5-dichlorobenzoic acid; 4-(4-iodo)benzyloxy-3,5-dibromobenzoic acid; 4-(naphthyl-2-methoxy)-3,5-dibromobenzoic acid; 1,2-bis-(4-hydroxyphenyl)-ethane-1,2-dione; 4-(9H-fluoren-9-yloxy)-3,5-diiodobenzoic acid; 4-[(1-bromo-6-fluoro)naphthyl-2-methoxy]-3,5-diiodobenzoic acid; 1,2-bis-(4-hydroxy-3,5-diiodophenyl)-ethane-1,2-dione; (4-fluorophenyl)-(4'-hydroxy-3,5-diiodophenyl)-methanone; 4-[3-(2-fluoro)phenoxybenzyloxy]-3,5-diiodobenzoic acid; 4-[2-(trifluoromethoxy)-benzyloxy]-3,5-diiodobenzoic acid; 4-(10-carboxy-decyloxy)-3,5-diiodobenzoic acid; 4-(4-tert-butylbenzyloxy)-3,5-dichlorobenzoic acid; 4-(2-phenylbenzyloxy)-3,5-dibromobenzoic acid; {4-[(4-hydroxy-3,5-diiodophenyl)-oxo-acetyl]-2,6-diiodophenoxy}-acetic acid benzyl ester; 4-allyloxy-3,5diiobenzoic acid; {4-[(4-hydroxy-3,5-diiodophenyl)-oxo-acetyl]-2,6-diiodophenoxy}-acetic acid; 4-(2-phenyl)benzyloxy-3,5-dichlorobenzoic acid; 4-hydroxy-3,5-diiodobenzoic acid 2-trimethylsilyl-1-ethoxymethoxy ester; 3,3',5,5'-tetraiodo-4,4'-sulfonyldiphenol; 4-[(1',4'-tetramethyl)cyclohexyl-2',3'-(2-ethyl)benzoylmethoxy]-3,5-diiodobenzoic acid; 4-hexadecyloxy-3,5-diiodobenzoic acid; [4-(4-hydroxy-3,5-diiodo-benzenesulfonyl)-2,6-diiodophenoxy]-acetic acid benzyl ester; [4-(4-hydroxy-3,5-diiodo-benzenesulfonyl)-2,6-diiodophenoxy]-acetic acid phenyl ester; 4-[3,5-diiodo-4-(3-iodo-benzyloxy)-benzenesulfonyl]-2,6-diiodo-phenol; 4-hydroxy-3,5-diiodobenzoic acid phenoxycarbonylmethyl ester; 4-hydroxy-3,5-diiodobenzoic acid [4-chloro-2-(2-chlorobenzoyl)phenylcarbamoyl]-methyl ester; [3,5-diiodo-4-(3-iodobenzyloxy)phenyl]-(4-hydroxy-3,5-diiodophenyl)methanone; [4-(4-hydroxy-3,5-diiodobenzoyl)2,6-diiodophenoxy]acetic acid phenyl ester; 1-[3,5-diiodo-4-(3-iodobenzyloxy)phenyl]-2-(4-hydroxy-3,5-diiodophenyl) ethane-1,2-dione; {4-[(4-hydroxy-3,5-diiodophenyl)oxoacetyl]-2,6-diiodophenyoxy}acetic acid phenyl ester; carbonic acid benzyl ester 4-(4-hydroxy-3,5-diiodobenzoyl)-2,6-diiodophenyl ester; 4-hydroxy-3,5-diiodobenzoic acid 3-benzyloxy-benzyl ester; [4-(9H-fluoren-9-yloxy)-3,5-diiodophenyl]-(4-hydroxy-3,5-diiodophenyl)methanone; and 3-[3,5-diiodo-4-(3-iodobenzyloxy)phenyl]-3-(4-hydroxy-3,5-diiodophenyl)-3H-isobenzofuran-1-one.

Other compounds of interest herein include N-benzyl-4-hydroxy-3,5-diiodo-N-methylbenzamide; N-benzyl-4-hydroxy-3,5-diiodo-N-ethylbenzamide; 1-(4-hydroxy-3,5-diiodophenyl)-2-phenylethanone; 1-(4-hydroxy-3,5-diiodophenyl)hexan-1-one; (4-hydroxy-3,5-diiodophenyl)-(4-hydroxyphenyl)methanone; (4-hydroxy-3,5-diiodophenyl)-(4-iodophenyl)methanone; 1,3,5,7-tetraiodonaphthalene-2,6-diol; 1,3,5,7-tetraiodo-6-(3-iodobenzyloxy)naphthalen-2-ol; 1,3,5,7-tetraiodo-6-methoxynaphthalen-2-ol; 4-{[1,3]dithian-2-yl}-4-(4-hydroxy-3,5-diiodophenyl)-2,6-diiodophenol; 4-[1,3]dithian-2-yl-2,6-diiodophenol; (4-hydroxy-3,5-diiodophenyl)-(4-methoxyphenyl)methanone; 2,6-diiodo-4-(4-methoxybenzenesulfonyl)phenol; (3,5-diiodo-4-methoxyphenyl)-(4-hydroxy-3,5-diiodophenyl)methanone; 4-(3,5-diiodo-4-methoxybenzenesulfonyl)-2,6-diiodophenol; and 3-(3,5-diiodo-4-methoxyphenyl)-3-(4-hydroxy-3,5-diiodophenyl)-3H-isobenzofuran-1-one.

Further compounds of interest herein include cyclohexylmethyl 4-hydroxy-3,5-diiodobenzoate; 3-(3,5-diiodo-4-methoxyphenyl)-3-(4-hydroxy-3,5-diiodophenyl)-3H-isobenzofuran-1-one; (2-fluorophenyl)-(4-hydroxy-3,5-diiodophenyl)methanone; 1-(4-hydroxy-3,5-diiodophenyl)-nonan-1-one; 1-(4-hydroxy-3,5-diiodophenyl)hexan-1-one; 4-(2-cyclohexylethoxy)-4-hydroxy-3,5-diiodobenzoic acid; (2,4-dimethoxyphenyl)-(4-hydroxy-3,5-diiodophenyl)methanone; 4'-hydroxy-3',5'-diiodobephenyl-4-carbonitrile; n-butyl 4-hydroxy-3,5-diiodobenzoate; 4-(N-benzyl-N-ethylcarbamoyl)-2,6-diiodophenyl 4-hydroxy-3,5-diiodobenzoate; 2,6-diiodo-[4-(1-benzyl)triazolyl]phenol; methyl 3-(4-hydroxy-3,5-diiodophenyl)acrylate; benzyl 4-hydroxy-3,5-diiodobenzoate; 3-(2-oxo-2-phenylethoxycarbonyl)allyl 4-hydroxy-3,5-diiodobenzoate; 1-methyl-1-hexyl 4-hydroxy-3,5-diiodobenzoate; heptyl 4-hydroxy-3,5-diiodobenzoate; 2,6-diiodo-4-octylphenol; 2,4,4-trimethylpentyl 4-hydroxy-3,5-diiodobenzoate; 3-[3,5-diiodo-4-(2-iodobenzyloxy)phenyl]propionic acid; 2,6-dichloro-4-phenylethynylphenol; 3-(4-hydroxy-3,5-diiodobenzylidene)-1,3-dihydroindol-2-one; 2-(4-t-butyl) benzyloxy-3,5-diiodobenzoic acid; 1-(4-hydroxy-3,5-diiodophenyl)butan-1-one; 4-[2-(3,4-dihydro-2H-benzo[b][1,4]dioxepin-7-yl)-2-oxoethoxy]-3,5-diiodobenzoic acid; 4-[2-(4-bromophenyl)-2-oxoethoxy]-3,5-diiodobenzoic acid; 2,6-diiodo-4-(4-nitrophenyl)phenol; 4-(1-hydroxynonyl)-2,6-diiodophenol; 2-methyl-6-(3-iodobenzyloxy)-5,7,8-trimethylchroman-2-carboxylic acid; 6-(2-iodobenzyloxy)2,5,7,8-tetramethylchroman-2-carboxylic acid; 4-cyclohexylmethoxy-3,5-diiodobenzoic acid; 1-(4-hydroxy-3,5-diiodophenyl)pentan-1-one; 5,7-dihydroxy-6,8-diiodo-2-phenylchromen-4-one; and N,N-dibenzyl-4-hydroxy-3,5-diiodobenzamide.

C. Preparation of the Compounds

The preparation of the above compounds is described below. Examplary protocols are provided in the Examples, and serve as models upon which syntheses of similar compounds may be readily devised. Hence, any compound or similar compound may be synthesized according to a method discussed in general below or by only minor modification of the methods by selecting appropriate starting materials. Additionally, certain compounds described herein may be obtained from commercial sources known to those of skill in the art (see, em, Aldrich Chemical Company, Milwaukee, Wis.; Sigma, St. Louis, Mo.; Fluka Chemical Corp., Milwaukee, Wis.).

Certain compounds, such as biphenyl ether sulfonic acids, provided herein may be prepared by methods well known to those of skill in the art. For example, sulfonation of the biphenyl ether nucleus using, e.g., concentrated sulfuric acid, fuming sulfuric acid, $SO_3$ or $ClSO_3H$ is well known (see, e.g., Nelson, in Olah, "Friedel-Crafts and Related Reactions", vol. 3, pp. 1355–1392, Interscience, New York (1964) and Gilbert "Sulfonation and Related Reactions", pp 62–83 and 87–124, Interscience, New York (1965)). Sulfonation will occur preferentially at the positions ortho and para to the oxygen atom. Sulfonation of diphenyl ether with $SO_2Cl_2$ provides a bis(sulfonyl chloride). Reaction of this derivative with one equivalent of an alcohol, eq., decanol, provides a monosulfonic ester-sulfonic acid derivative. Nitration (by treatment with, e.g., concentrated nitric and sulfuric acids, or with a mixture of nitric acid and water, acetic acid or acetic anhydride, see, e.g., Olah and Kuhn, in Olah, "Friedel-Crafts and Related Reactions", vol. 3, pp. 1355–1392, Interscience, New York (1964)) and Friedel-Crafts alkylation (by treatment with, e.g., an alkene and a catalyst such as AlCl$_3$ or a mineral acid (i.e., sulfuric acid), see, e.g., Bonvino et al. (1981) *Tetrahedron* 37:61 5)) of diaryl ethers are also well known, and also provides ortho and para substitution. Thus, nitration, alkylation and sulfonation of a diaryl ether can be used to prepare certain compounds provided herein.

Alternatively, reaction of a chloro-substituted arylsulfonic acid with an aryloxy anion gives the diaryl ether sulfonic acids provided herein. For example, reaction of 5-nitro-2-chlorobenzenesulfonic acid with sodium phenoxylate affords 4-nitro-2-sulfodiphenyl ether. Other compounds provided herein may be prepared by appropriate choice of starting materials.

Certain of the compounds provided herein 1-aryl-3-amino-5-pyrazolone derivatives. These compounds are well known to those of skill in the art (see, e.q., British Patent Specification 1209945). The compounds may be prepared by reaction of the appropriate arylhydrazine with a compound of formula H$_2$NC(O)CH$_2$COOR or RC(O)NHC(O)CH$_2$CO—OR with loss of ROH and water to provide the desired compounds (see, e.g., March, "Advanced Organic Chemistry", 3rd ed., p. 804, John Wiley & Sons, Inc., New York (1985)). Alternatively, reaction of the arylhydrazine with a-cyanoacetate provides a 1-aryl-3-amino-5-pyrazolone. Acylation of the amino group affords the compounds provided herein.

Other compounds provided herein are 1-aryl-3-amino-4-(aryldiazo)-5-pyazolone derivatives. These compounds are also well known to those of skill in the art (see, e.g., British Patent Specification 1209945). Reaction of the above 1-aryl-3-amino-5-pyrazolone compounds with a diazatized aniline derivative affords the desired 4-aryidiazo derivatives.

Further compounds provided herein include alkylsulfonylhydrazone derivatives of 4-quinolones. These compounds are well known in the art (see, e.g., International Patent Application Publication No. WO 94/07492). Preparation of these compounds may be achieved by reaction of the appropriate quinolone with the corresponding alkylsulfonylhydrazide. The requisite quinolone derivatives may be prepared by standard methods.

Other compounds provided herein may be prepared by the methods described in International Patent Application Publication No. WO 96/11904, Evans et al. ((1998) *Tetrahedron Lett*. 39(19):2937–2940), Salamonczyk et al. ((1997) *Tetrahedron Lett*. 38(40):6965–6968, and Bell et al. ((1997) *Can. J. Chem*. 75(6):873–883, or minor modifications of these methods. These references are incorporated by reference herein in their entirety.

Briefly, iodination of tyrosine with by treatment with, for example, NaI and NaIO$_3$ in acetic acid, followed by NaHSO$_3$ to remove excess I$_2$ provides a tyrosine derivative that is iodinated at one or both of the positions ortho to the hydroxyl group. Protection of the amino functionality by, e.g., acetylation with acetic anhydride, followed by esterification of the carboxyl group with, e.g., ethanol and an acid catalyst, e.g., sulfuric acid, provides an iodinated derivative of N-acetyltyrosine ethyl ester. Oxidative coupling of this iodinated derivative using air under pressure of 20 atmospheres with MnSO$_4$ and H$_3$BO$_4$ in ethanol with a piperidine additive affords an N-acetylthyroxine ethyl ester derivative. Hydrolysis of the N-acetyl group and the ethyl ester with HCl and acetic acid provides the desired thyroxine derivative.

Alternatively, the compounds provided herein may be synthesized by copper(II)-promoted coupling of arylboronic acids and phenols. Briefly, an iodinated tyrosine derivative, as described above, may be coupled with an arylboronic acid by reaction with Cu(OAc)$_2$ in the presence of powdered 4 Å molecular sieves at ambient temperature. Addition of an amine base, such as triethylamine, and chromatographic purification provides the desired diaryl ether derivative.

As a further alternative, the thyroxine derivatives provided herein may be synthesized from a para-hydroxybenzyl alcohol, or iodinated derivatives thereof. Reaction of the para-hydroxybenzyl alcohol with NaBiO$_3$ (2 equiv.) in ethyl acetate/acetic acid/water provides the corresponding 4-oxocyclohexadienylidene epoxide (e.g., 1-oxa-spiro[2,5] bicycloocta-4,7-dien-6-one). Reaction of this compound with tyrosine, or an iodinated derivative thereof, in dimethyl formamide at pH=8 in borate buffer affords the desired thyroxine and thyroxine derivatives.

Still other compounds provided herein are benzyl ether derivatives of phenolic carboxylic acids. These compounds may be prepared by reaction of one equivalent of the phenolic carboxylic acid with 2.5 equivalents of the desired benzyl halide and three equivalents of cesium carbonate in dimethylformamide. The resulting benzyl ether-ester is saponified using LiOH in water/tetrahydrofuran to afford the benzyl ether-carboxylic acid derivatives provided herein.

Iodination of phenols to afford the diiodo phenols provided herein may be achieved by reaction with iodine and potassium iodide in water in the presence of a buffer such as TRIS (tris(hydroxymethyl)aminomethane).

The silylated compounds provided herein may be synthesized by a variety of methods known to those of skill in the art. In particular, silyl esters and ethers may be prepared by reaction of the corresponding acid or alcohol with a silyl halide, triflate or imidazole.

Any of the compounds provided herein may be prepared using a combinatorial approach, using, e.g., either Wang resin (4-(hydroxymethyl)phenoxymethylcopoly-(styrene-1% divinylbenzene (DVB))) or Rink resin (4-(α-amino-2, 4-dimethoxybenzyl)phenoxymethyl polystyrene crosslinked with 1% DVB). In the preparation certain of the compounds provided herein, these resins may be used as illustrated below:

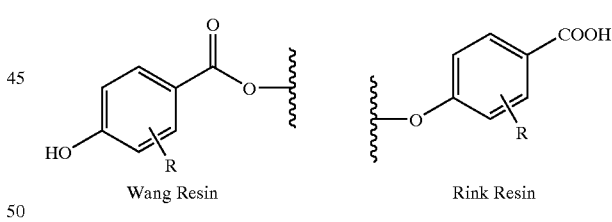

Wang Resin             Rink Resin where, in the case of the Wang resin, the phenolic group may be derivatized, and in the case of the Rink resin, the carboxylic acid group may be derivatized. In both cases, if R is a reactive group, such as a halide, particularly an iodide, then this functionality may be altered using any of a variety of methods well known to those of skill in the art, such as S$_N$Ar reactions, Stille couplings, Suzuki couplings and Heck couplings. Any of these methods may also be conducted in solution phase in a non-combinatorial approach to prepare specific compounds provided herein.

Certain of the compounds provided herein are phenolic ether derivatives. These compounds may be prepared by reacting the parent phenol with a reactive halo compound, such as a benzylic halide or an α-halocarbonyl compound, in the presence of a base such as cesium carbonate in a polar solvent such as dimethylformamide.

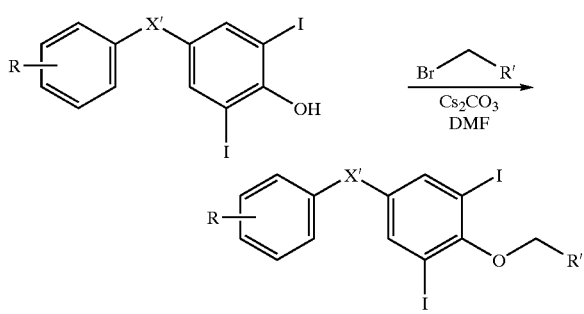

Certain of the compounds provided herein are carboxamide derivatives. These compounds may be synthesized from the corresponding carboxylic acid and an appropriate amine. Generally, the reaction is carried out in the presence of an amide or peptide coupling reagent, such as 1-(3-dimethylaminopropyl)-3-ethylcarbodiimide hydrochloride (EDC), dicyclohexylcarbodiimide (DCC) or 1-hydroxybenzotriazole (HOBt).

Other compounds may be prepared by nucleophilic aromatic substitution reactions, using an appropriate nucleophile, including, but not limited to, an alkoxide, an amine anion, or an azide, and an appropriate substrate, such as an aryl fluoride. Thus, certain of the compounds provided herein may be synthesized by the following method:

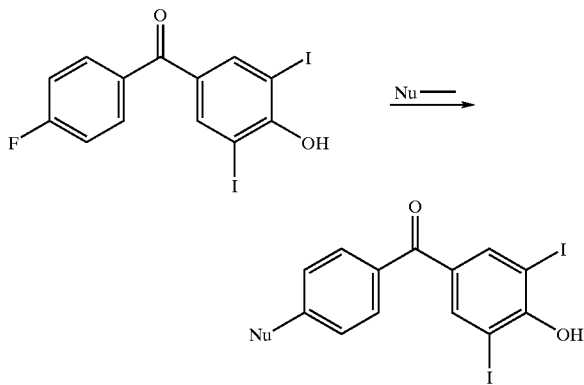

Other compounds are phenolic ester derivatives. These compounds may be prepared by reacting the parent phenol with an acyl halide or anhydride. If the parent phenol has another acidic group, such as a carboxylic acid group, it may be necessary to selectively hydrolyze the resulting anyhydride to arrive at the desired ester-acid.

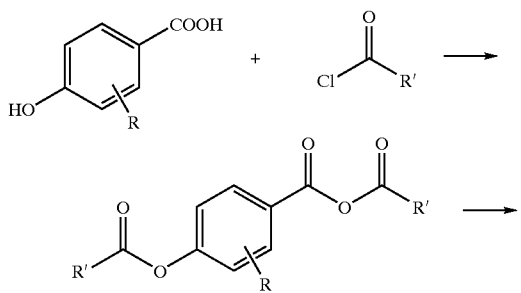

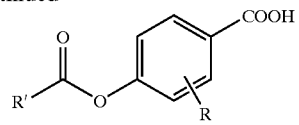

Further compounds provided herein are those where X' comprises a carbonyl derivative. Such compounds may be prepared by standard methods from the corresponding carbonyl compound by, e.g., ketalization, reduction, nucleophilic addition (with, e.g., a Grignard reagent), or other appropriate method.

Other compounds provided herein include compounds where a nitro group is used as an acid-mimicking group. Nitro compounds may be synthesized from the parent compound by methods well known to those of skill in the art. For example, as described in detail above, nitration of aromatic compounds may be achieved by treatment with, e.g., a mixture of nitric and sulfuric acids. Compounds possessing both a nitro and an iodo group may be prepared in one step by treatment with nitric acid and iodine (see, e.g., Example 5).

Certain compounds provided herein utilize a tetrazolyl group as an acid-mimicking group. Methods of synthesis of tetrazoles are well known to those of skill in the art. For example, reaction of the appropriate cyano compound with azide ion affords tetrazoles. The requisite cyano compounds may be prepared from the corresponding carboxylic acid by conversion to the carboxamide followed by dehydration.

D. Formulation of Pharmaceutical Compositions

The pharmaceutical compositions provided herein contain therapeutically effective amounts of one or more PAI antagonists of formula I that are useful in the prevention, treatment, or amelioration of one or more of the symptoms of thrombotic disorders, including, but not limited to, myocardial infarction, deep vein thrombosis and disseminated intravascular coagulation, and cancer, including, but not limited to, tumors, metastatic solid tumors and breast cancer. The compositions contain one or more substituted biaryl ethers that possess at least one acidic moiety, including, but not limited to, a carboxylic acid, sulfonic acid, sulfinic acid, phosphonic acid, phosphinic acid or boronic acid group.

The compounds are preferably formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. Typically the compounds described above are formulated into pharmaceutical compositions using techniques and procedures well known in the art (see, e.g., Ansel *Introduction to Pharmaceutical Dosage Forms, Fourth Edition* 1985, 126).

In the compositions, effective concentrations of one or more compounds or pharmaceutically acceptable derivatives is (are) mixed with a suitable pharmaceutical carrier or vehicle. The compounds may be derivatized as the corresponding salts, esters, enol ethers or esters, acids, bases, solvates, hydrates or prodrugs prior to formulation, as described above. The concentrations of the compounds in the compositions are effective for delivery of an amount, upon administration, that ameliorates one or more of the symptoms of thrombotic disorders, including, but not limited to, myocardial infarction, deep vein thrombosis and disseminated intravascular coagulation, and cancer, including, but not limited to, tumors, metastatic solid tumors and breast cancer. Typically, the compositions are formulated for single dosage administration. To formulate a composition, the weight fraction of compound is dissolved, suspended, dispersed or otherwise mixed in a selected vehicle at an effective concentration such that the treated condition is relieved or ameliorated. Pharmaceutical carriers or vehicles suitable for administration of the compounds provided herein include any such carriers known to those skilled in the art to be suitable for the particular mode of administration.

In addition, the compounds may be formulated as the sole pharmaceutically active ingredient in the composition or may be combined with other active ingredients. Liposomal suspensions, including tissue-targeted liposomes, particularly tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulted compound, pelleted by centrifugation, and then resuspended in PBS.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in known in vitro and in vivo systems (see, e.g., Nilsson (1987) *Fibrinolysis* 1:163–168; U.S. Pat. Nos. 5,750,530, 5,902,812, 5,891,877; Charlton et al. (1996) *Thrombosis and Haemostasis* 75(5):808–815; Charlton et al. (1997) *Fibrinolysis and Proteolysis* 11(1):51–56; Bjorquist et al. (1998) *Biochemistry* 37:1227–1234) and then extrapolated therefrom for dosages for humans.

For example, in one assay, t-PA (25 µL, 100 IU/mL in 1 M acetate buffer, pH 3.9) is added to 25 µL of plasma obtained from normal citrated blood (1 vol of 0.1 mol/L of sodium citrate+9 vol blood, centrifuged at 2000×g for 20 min at 4° C.) and allowed to react with PAI during 10 min at room temperature. The reaction is terminated by addition of 50 µL of acetate buffer and the sample is frozen to eliminate plasmin inhibitors. Before assay, the sample is thawed at 37° C. and diluted 1:40 with Tris buffer.

A chromogenic assay is carried out using the above reagents and solutions in the following amounts. The mixture of plasminogen (native (Glu) type prepared from Cohn supernatant I by affinity chromatography) and S2251 (D-Val-Leu-Lys-pNA, Kabi-Vitrum) is freshly made in Tris buffer before use.

| | |
|---|---|
| Standard dilution plasma, 20 to 25° C. | 200 µL |
| Plasminogen (0.1 mg/mL)/S2251 (0.8 mmol/L), 2 to 8° C. | 200 µL |
| Fibrin(ogen) fragments (0.66 mg/mL), 20 to 25° C. | 100 µL |
| Incubation at 37° C. for 1 h | |
| 20% acetic acid | 100 µL |

In this assay, each compound is incubated with PAI-1 prior to addition to the tPA assay system. Inhibition of PAI-1 results in the production of plasmin from plasminogen. The generated plasmin cleaves the chromogenic substrate, S2251, producing pNA (para-nitroaniline). The pNA is detected spectrophotometrically at 405 nm.

Other chromogenic substrates that may be used in similar assays include, but are not limited to, S2288 (H-D-Ile-Pro-Arg-pNA), S2444 (Glu-Glu-Arg-pNA), S2403 (PyroGlu-Phe-Lys-pNA) and S2238 (H—D-Phe-Pip-Arg-pNA).

Alternatively, Flavigen ($CH_3SO_2$-D-HHT-Gly-Arg-pNA) is used in a tPA/PAI-1 assay system in Tris/Tween® 80 buffer.

The concentration of active compound in the pharmaceutical composition will depend on absorption, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of thrombotic disorders, including, but not limited to, myocardial infarction, deep vein thrombosis and disseminated intravascular coagulation, and cancer, including, but not limited to, tumors, metastatic solid tumors and breast cancer.

Typically a therapeutically effective dosage should produce a serum concentration of active ingredient of from about 0.1 ng/ml to about 50–100 µg/ml. The pharmaceutical compositions typically should provide a dosage of from about 0.001 mg to about 2000 mg of compound per kilogram of body weight per day. Pharmaceutical dosage unit forms are prepared to provide from about 1 mg to about 1000 mg and preferably from about 10 to about 500 mg of the essential active ingredient or a combination of essential ingredients per dosage unit form.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Preferred pharmaceutically acceptable derivatives include acids, bases, enol ethers and esters, salts, esters, hydrates, solvates and prodrug forms. The derivative is selected such that its pharmacokinetic properties are superior to the corresponding neutral compound.

Thus, effective concentrations or amounts of one or more of the compounds described herein or pharmaceutically acceptable derivatives thereof are mixed with a suitable pharmaceutical carrier or vehicle for systemic, topical or local administration to form pharmaceutical compositions. Compounds are included in an amount effective for ameliorating one or more symptoms of, or for treating or preventing thrombotic disorders, including, but not limited to, myocardial infarction, deep vein thrombosis and disseminated intravascular coagulation, and cancer, including, but not limited to, tumors, metastatic solid tumors and breast cancer. The concentration of active compound in the composition will depend on absorption, inactivation, excretion rates of the active compound, the dosage schedule, amount administered, particular formulation as well as other factors known to those of skill in the art.

The compositions are intended to be administered by a suitable route, including orally, parenterally, rectally, topically and locally. For oral administration, capsules and tablets are presently preferred. The compositions are in liquid, semi-liquid or solid form and are formulated in a manner suitable for each route of administration. Preferred modes of administration include parenteral and oral modes of administration. Oral administration is presently most preferred.

Solutions or suspensions used for parenteral, intradermal, subcutaneous, or topical application can include any of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampules, disposable syringes or single or multiple dose vials made of glass, plastic or other suitable material.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous sodium bicarbonate. Derivatives of the compounds, such as prodrugs of the compounds may also be used in formulating effective pharmaceutical compositions.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are typically formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

The composition can contain along with the active ingredient: a diluent such as lactose, sucrose, dicalcium phosphate, or carboxymethylcellulose; a lubricant, such as magnesium stearate, calcium stearate and talc; and a binder such as starch, natural gums, such as gum acaciagelatin, glucose, molasses, polvinylpyrrolidine, celluloses and derivatives thereof, povidone, crospovidones and other such binders known to those of skill in the art. Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, acetate, sodium citrate, cyclodextrine derivatives, sorbitan monolaurate, triethanolamine sodium acetate, triethanolamine oleate, and other such agents. Actual methods of preparing such dosage forms are known, or will be apparent, to those skilled in this art; for example, see Remington's Pharmaceutical Sciences, Mack Publishing Company, Easton, Pa., 15th Edition, 1975. The composition or formulation to be administered will, in any event, contain a quantity of the active compound in an amount sufficient to alleviate the symptoms of the treated subject.

Dosage forms or compositions containing active ingredient in the range of 0.005% to 100% with the balance made up from non-toxic carrier may be prepared. For oral administration, a pharmaceutically acceptable non-toxic composition is formed by the incorporation of any of the normally employed excipients, such as, for example pharmaceutical grades of mannitol, lactose, starch, magnesium stearate, talcum, cellulose derivatives, sodium crosscarmellose, glucose, sucrose, magnesium carbonate or sodium saccharin. Such compositions include solutions, suspensions, tablets, capsules, powders and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of these compositions are known to those skilled in the art. The contemplated compositions may contain 0.001%–100% active ingredient, preferably 0.1–85%, typically 75–95%.

The active compounds or pharmaceutically acceptable derivatives may be prepared with carriers that protect the compound against rapid elimination from the body, such as time release formulations or coatings.

The compositions may include other active compounds to obtain desired combinations of properties. The compounds of formula I, or pharmaceutically acceptable derivatives thereof as described herein, may also be advantageously administered for therapeutic or prophylactic purposes together with another pharmacological agent known in the general art to be of value in treating one or more of the diseases or medical conditions referred to hereinabove, such as beta-adrenergic blocker (for example atenolol), a calcium channel blocker (for example nifedipine), an angiotensin converting enzyme (ACE) inhibitor (for example lisinopril), a diuretic (for example furosemide or hydrochlorothiazide), an endothelin converting enzyme (ECE) inhibitor (for example phosphoramidon), a neutral endopeptidase (NEP)

inhibitor, an HMGCoA reductase inhibitor, a nitric oxide donor, an anti-oxidant, a vasodilator, a dopamine agonist, a neuroprotective agent, a steroid, a beta-agonist, an anticoagulant, or a thrombotic agent. It is to be understood that such combination therapy constitutes a further aspect of the compositions and methods of treatment provided herein.

1. Compositions for Oral Administration

Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

In certain embodiments, the formulations are solid dosage forms, preferably capsules or tablets. The tablets, pills, capsules, troches and the like can contain any of the following ingredients, or compounds of a similar nature: a binder; a diluent; a disintegrating agent; a lubricant; a glidant; a sweetening agent; and a flavoring agent.

Examples of binders include microcrystalline cellulose, gum tragacanth, glucose solution, acacia mucilage, gelatin solution, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

If oral administration is desired, the compound could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. The active ingredient is a compound or pharmaceutically acceptable derivative thereof as described herein. Higher concentrations, up to about 98% by weight of the active ingredient may be included.

Pharmaceutically acceptable carriers included in tablets are binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines. Sugar-coated tablets are compressed tablets to which different layers of pharmaceutically acceptable substances are applied. Film-coated tablets are compressed tablets which have been coated with a polymer or other suitable coating. Multiple compressed tablets are compressed tablets made by more than one compression cycle utilizing the pharmaceutically acceptable substances previously mentioned. Coloring agents may also be used in the above dosage forms. Flavoring and sweetening agents are used in compressed tablets, sugar-coated, multiple compressed and chewable tablets. Flavoring and sweetening agents are especially useful in the formation of chewable tablets and lozenges.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic add, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Diluents include lactose and sucrose. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic adds include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is preferably encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. Re 28,819 and 4,358,603. Briefly, such formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more anitoxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

2. Injectables, Solutions and Emulsions

Parenteral administration, generally characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow-release or sustained-release system, such that a constant level of dosage is maintained (see, e.g., U.S. Pat. No. 3,710,795) is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polyporpoylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses throught the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylceluose, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampoule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. Typically a therapeutically effective dosage is formulated to contain a concentration of at least about 0.1% w/w up to about 90% w/w or more, preferably more than 1% w/w of the active compound to the treated tissue(s). The active ingredient may be administered at once, or may be divided into a number of smaller doses to be administered at intervals of time. It is understood that the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of the claimed formulations.

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

3. Lyophilized Powders

Of interest herein are also lyophilized powders, which can be reconstituted for administration as solutions, emulsions and other mixtures. They may also be reconsitituted and formulated as solids or gels.

The sterile, lyophilized powder is prepared by dissolving a compound of formula I in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, typically, about neutral pH. Subsequent sterile filtration of the solution followed by lyophilization under standard conditions known to those of skill in the art provides the desired formulation. Generally, the resulting solution will be apportioned into vials for lyophilization. Each vial will contain a single dosage (10–1000 mg, preferably 100–500 mg) or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, about 1–50 mg, preferably 5–35 mg, more preferably about 9–30 mg of lyophilized powder, is added per mL of sterile water or other suitable carrier. The precise amount depends upon the selected compound. Such amount can be empirically determined.

4. Topical Administration

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable derivatives thereof may be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will typically have diameters of less than 50 microns, preferably less than 10 microns.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

These solutions, particularly those intended for ophthalmic use, may be formulated as 0.01%–10% isotonic solutions, pH about 5–7, with appropriate salts.

5. Compositions for Other Routes of Administration

Other routes of administration, such as topical application, transdermal patches, and rectal administration are also contemplated herein.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The typical weight of a rectal suppository is about 2 to 3 gm.

Tablets and capsules for rectal administration are manufactured using the same pharmaceutically acceptable substance and by the same methods as for formulations for oral administration.

6. Articles of Manufacture

The compounds or pharmaceutically acceptable derivatives may be packaged as articles of manufacture containing packaging material, a compound or pharmaceutically acceptable derivative thereof provided herein, which is effective for antagonizing PAI, particularly PAI-1, or for treatment, prevention or amelioration of one or more symptoms of thrombotic disorders, including, but not limited to, myocardial infarction, deep vein thrombosis and disseminated intravascular coagulation, and cancer, including, but not limited to, tumors, metastatic solid tumors and breast cancer, and a label that indicates that the compound or pharmaceutically acceptable derivative thereof is used for antagonizing PAI, particularly PAI-1, or for treatment, prevention or amelioration of one or more symptoms of thrombotic disorders, including, but not limited to, myocardial infarction, deep vein thrombosis and disseminated intravascular coagulation, and cancer, including, but not limited to, tumors, metastatic solid tumors and breast cancer.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disorder in which PAI, particularly PAI-1, is implicated as a mediator or contributor to the symptoms or cause.

E. Evaluation of the Activity of the Compounds

Standard physiological, pharmacological and biochemical procedures are available for testing the compounds to identify those that possess biological activities that interfere with, antagonize, inhibit, or otherwise modulate the activity of PAI, particularly PAI-1. For example, the properties of a potential inhibitor may be assessed as a function of its ability to antagonize PAI activity including the ability in vitro to antagonize the activity of PAI-1.

Assays that may be used to evaluate PAI-1 activity are provided herein (see, EXAMPLE 29). Other assays that may be used to evaluate PAI-1 activity are well known to those of skill in the art. See also, e.g., Madison et al. (1989) *Nature* 339:721–723; Madison et al. (1990) *Proc. Natl. Acad. Sci. USA* 87:3530–3533; Madison et al. (1993) *Science* 262:419–421; U.S. Pat. Nos. 5,750,530, 5,902,812, 5,891,877; Charlton et al. (1996) *Thrombosis and Haemostasis* 75(5):808–815; and Charlton et al. (1997) *Fibrinolysis and Proteolysis* 11(1):51–56.

For example, in one assay, t-PA (25 μL, 100 IU/mL in 1 M acetate buffer, pH 3.9) is added to 25 μL of plasma obtained from normal citrated blood (1 vol of 0.1 mol/L of sodium citrate+9 vol blood, centrifuged at 2000×g for 20 min at 4° C.) and allowed to react with PAI during 10 min at room temperature. The reaction is terminated by addition of 50 μL of acetate buffer and the sample was frozen to eliminate plasmin inhibitors. Before assay, the sample is thawed at 37° C. and diluted 1:40 with Tris buffer.

A chromogenic assay is carried out using the above reagents and solutions in the following amounts. The mixture of plasminogen (native (Glu) type prepared from Cohn supernatant I by affinity chromatography) and S2251 (D-Val-Leu-Lys-pNA, Kabi-Vitrum) is freshly made in Tris buffer before use.

| | |
|---|---|
| Standard dilution plasma, 20 to 25° C. | 200 μL |
| Plasminogen (0.1 mg/mL)/S2251 (0.8 mmol/L), 2 to 8° C. | 200 μL |
| Fibrin(ogen) fragments (0.66 mg/mL), 20 to 25° C. | 100 μL |
| Incubation at 37° C. for 1 h | |
| 20% acetic acid | 100 μL |

In this assay, each compound is incubated with PAI-1 prior to addition to the tPA assay system. Inhibition of PAI-1 results in the production of plasmin from plasminogen. The generated plasmin cleaves the chromogenic substrate, S2251, producing pNA (para-nitroaniline). The pNA is detected spectrophotometrically at 405 nm.

Other chromogenic substrates that may be used in similar assays include, but are not limited to, S2288 (H-D-Ile-Pro-Arg-pNA), S2444 (Glu-Glu-Arg-pNA), S2403 (PyroGlu-Phe-Lys-pNA) and S2238 (H-D-Phe-Pip-Arg-pNA).

Alternatively, Flavigen ($CH_3SO_2$-D-HHT-Gly-Arg-pNA) is used in a tPA/PAI-1 assay system in Tris/Tween® 80 buffer.

Using such assays, the relative abilities of the compounds provided herein to antagonize or otherwise modulate the activity of PAI, particularly PAI-1, have been and can be assessed. Those that possess the desired in vitro properties, such as specific antagonism of PAI-1, are selected. The selected compounds that exhibit desirable activities may be therapeutically useful in the methods described herein and are tested for such uses employing the above-described assays from which the in vivo effectiveness may be evaluated. Compounds that exhibit the in vitro activities that correlate with the in vivo effectiveness will then be formulated in suitable pharmaceutical compositions and used as therapeutics.

F. Methods of Use of PAI Antagonists

1. Methods of Treating, Preventing or Ameliorating One or More Symptoms of Thrombotic Disorders PAI, particularly PAI-1, has been implicated in the development and progression of thrombotic disorders, including, but not limited to, myocardial infarction, thrombosis associated with diabetes or obesity, reocclusion following thrombolytic therapy, deep vein thrombosis and disseminated intravascular coagulation. Methods using therapeutically effective concentrations one or more of the compounds of formula I, or pharmaceutically acceptable derivatives thereof, for treating, preventing or ameliorating one or more symptoms of thrombotic disorders are provided herein. In particular, methods for using the compounds to treat, prevent or ameliorate one or more symptoms of myocardial infarction, thrombosis associated with diabetes or obesity, reocclusion following thrombolytic therapy, deep vein thrombosis and disseminated intravascular coagulation are provided herein.

Preferably, a medicament containing the compound is administered orally, although administration by other methods, such as, but not limited to, topical, parenteral, intravenous (IV) and local administration may be tolerated in some instances. Generally, the medicament containing the compound is injected into the circulatory system of a subject in order to deliver a dose to the targeted cells. Targeting may be effected by linking the compound to a targeting agent specific for the desired cells, such as, but not limited to, endothelial cells. See, e.g., U.S. Pat. Nos. 5,456,663, 4,764, 359, 5,543,391, 5,820,879, 5,026,558. For example, the compounds provided herein may be encapsulated in a microcapsule, liposome, or biodegradeable material, including, but not limited to, waxes, cellulosic materials, and polyvinyl polymers, that is linked to one or more targeting particles, including, but not limited to, antibodies including monoclonal antibodies, antibody fragments, antigen fragments, certain white blood cells such as phages, and polar lipid groups including sphingosine, ceramide, phophatidyl choline, phosphatidyl glycerol, phosphatidyl ethanolamine, phosphatidyl inositol, phosphatidyl serine cardiolipin, phosphatidic acid, sphingomyelin and other sphingolipids. Other methods of targeting include entrapping a compound provided herein in an encapsulted microparticle composition that, when exposed to a selected target stimulus related to pH, temperature, radiation, or the presence of a selected ligand or ion-channel activator, decondenses to release the compound into the target site. Dosages may be determined empirically, but will typically be in the range of about 0.01 mg to about 100 mg of the compound per kilogram of body weight as a daily dosage.

Methods of modulating the activity of PAI, particularly PAI-1, using the compounds and compositions provided herein are also provided. The compounds and compositions provided herein are active in assays that measure the activity of PAI, specifically PAI-1. Preferred are methods of inhibiting the activity of PAI, in particular PAI-1.

Methods of modulating the interaction of PAs, particularly tPA, with PAI, particularly PAI-1, by administering one or more of the compounds provided herein, or pharmaceutically acceptable derivatives thereof, are provided.

2. Methods of Treating, Preventing or Ameliorating One or More Symptoms of Cancer PAI, particularly PAI-1, has been implicated in the growth and metastasis of certain types of cancers, particularly solid tumors. Methods using therapeutically effective concentrations one or more of the compounds of formula I, or pharmaceutically acceptable derivatives thereof, for treating, preventing or ameliorating one or more symptoms of cancer are provided herein. In particular, methods for using the compounds to treat, prevent or ameliorate one or more symptoms of tumors, solid tumors, metastatic solid tumors and breast cancer are provided herein.

Preferably, a medicament containing the compound is administered orally, although administration by other methods, such as, but not limited to, topical, parenteral, intravenous (IV) and local administration may be tolerated in some instances. Generally, the medicament containing the compound is injected into the circulatory system of a subject in order to deliver a dose to the targeted cells. Targeting may be effected by linking the compound to a targeting agent specific for the desired cells, such as, but not limited to, tumor cells. See, e.g., U.S. Pat. Nos. 5,456,663, 4,764,359, 5,543,391, 5,820,879, 5,026,558. For example, the compounds provided herein may be encapsulated in a microcapsule, liposome, or biodegradeable material, including, but not limited to, waxes, cellulosic materials, and polyvinyl polymers, that is linked to one or more targeting particles, including, but not limited to, antibodies including monoclonal antibodies, antibody fragments, antigen fragments, certain white blood cells such as phages, and polar lipid groups including sphingosine, ceramide, phophatidyl choline, phosphatidyl glycerol, phosphatidyl ethanolamine, phosphatidyl inositol, phosphatidyl serine cardiolipin, phosphatidic acid, sphingomyelin and other sphingolipids. Other methods of targeting include entrapping a compound provided herein in an encapsulted microparticle composition that, when exposed to a selected target stimulus related to pH, temperature, radiation, or the presence of a selected ligand or ion-channel activator, decondenses to release the compound into the target site. Dosages may be determined empirically, but will typically be in the range of about 0.01 mg to about 100 mg of the compound per kilogram of body weight as a daily dosage.

Methods of modulating the interaction of PAs, particularly uPA, with PAI, particularly PAI-1, by administering one or more of the compounds provided herein, or pharmaceutically acceptable derivatives thereof, are provided.

Methods of attenuating metastasis by administration of one or more of the compounds and compositions provided herein are also provided.

Methods of modulating angiogenesis, preferably inhibiting angiogenesis, by administration of one or more of the compounds and compositions provided herein are provided.

The following examples are included for illustrative purposes only and are not intended to limit the scope of the invention. TLC's were performed using glass-bound Silica Gel 60 (F254) plates. HPLC's were performed with a Kromasil C18 column (5 $\mu$m, 150×4.6 mm) with a flow rate of 1 mL/min and a linear gradient of (water+0.01% trifluoroacetic acid): (acetonitrile+0.01% trifluoroacetic acid) according to the reported percentages, over a 20 minute run time. $^1$H NMR spectra were obtained using a Varian Inova 400; tetramethylsilane was used as an internal reference at $\delta 0.00$.

EXAMPLE 1

Synthesis of 4-(3-Bromo-benzyloxy)-3,5-diiodo-benzoic Acid 3-Bromo-benzyl Ester

A suspension of 3,5-diiodo-4-hydroxybenzoic acid (0.39 g, 1.0 mmol), 3-bromobenzyl bromide (0.62 g, 2.5 mmol), and cesium carbonate (0.98 g, 3.0 mmol) in 10 mL DMF was stirred for 15 hours at room temperature. The mixture was then poured into 1 M HCl (100 mL) and a white precipitate formed. The precipitate was isolated by filtration and was recrystallized from hot isopropanol/chloroform, yielding the title compound as bright white crystals (610 mg, 84%). $^1$H NMR (400 MHz, CDCl$_3$): $\delta$ 8.51 (s, 2H), 7.88 (d, J=7.6 Hz, 1H), 7.62 (d, J=8 Hz, 1H), 7.58 (d, J=8.4 Hz, 1H), 7.47–7.34 (m, 3H), 7.26–7.21 (m, 2H), 5.44 (s, 2H), 5.15 (s, 2H). TLC (9:1 Hex:EtOAc), R$_f$ 0.49.

EXAMPLE 2

Synthesis of 3,5-Diiodo-4-(3-bromo-benzyloxy)-benzoic Acid

A 1.2 M solution of lithium hydroxide (0.5 mL, 0.6 mmol) was added to a solution of 4-(3-bromo-benzyloxy)-3,5-diiodo- benzoic acid 3-bromo-benzyl ester (as prepared in Example 1, 363 mg, 0.5 mmol) in 4 mL THF. The biphasic solution was stirred for 17 hours, after which time the reaction mixture was poured into 1 M HCl (15 mL). The resulting white precipitate was isolated by filtration, rinsed with water, and dried in vacuo, yielding the title compound as a white powder (270 mg, 97%). $^1$H NMR (400 MHz, DMSO-d$_6$): $\delta$ 13.39 (br. s, 1H), 8.33 (s, 2H), 7.81 (s, 1H), 7.63–7.61 (m, 2H), 7.44 (appar. t, J=7.8 Hz, 1H), 5.00 (s, 2H). HPLC (30–90), 17.20 min. LRMS (EI–) calc'd for [C$_{14}$H$_9$BrI$_2$O$_3$—H] 556.8, found 556.6.

EXAMPLE 3

Synthesis of 3-[3,5-Diiodo-4-(3-iodo-benzyloxy)-phenyl]-propionic Acid 3-iodo-benzyl Ester A suspension of 3,5-diiodo-4-hydroxyphenylpropionic acid (209 mg, 0.5 mmol), 3-iodobenzyl bromide (371 mg, 1.25 mmol), and cesium carbonate (490 mg, 1.5 mmol) in 5 mL DMF was stirred for 15 hours at room temperature. After that time, 1 M HCl (15 mL) was added and an oil formed. The oil was extracted with ether and methanol was added. Crystals formed in the solution upon cooling, yielding the title compound as white crystals (390 mg, 92%). $^1$H NMR (400 MHz, CDCl$_3$): δ 8.00 (s, 1H), 7.71–7.60 (m, 6H), 7.29–7.26 (m, 1H), 7.16 (appar. t, J=7.8 Hz, 1H), 7.11 (appar. t, J=7.8 Hz, 1H), 5.05 (s, 2H), 4.91 (s, 2H), 2.87 (t, J=7.6 Hz, 2H), 2.67 (t, J=7.6 Hz, 2H). TLC (9:1 Hex:EtOAc), R$_f$ 0.29.

EXAMPLE 4

Synthesis of 3-[3,5-Diiodo-4-(3-iodo-benzyloxy)-phenyl]-propionic Acid

A 1.2 M solution of lithium hydroxide (275 ,L, 0.33 mmol) was added to a solution of 3-[3,5-diiodo-4-(3-iodo-benzyloxy)-phenyl]-propionic acid 3-iodo-benzyl ester (as prepared in Example 2, 213 mg, 0.25 mmol) in 2 mL THF. The biphasic solution was stirred for 14 hours, then 6 mL 0.5 M HCl was added and an oil formed. Methanol (0.5 mL) was added and the oil formed a solid, which was removed by filtration, yielding the title compound as an off-white powder (150 mg, 95%). $^1$H NMR (400 MHz, DMSO-d$_6$): δ 12.15 (s, 1H), 7.96 (s, 1H), 7.76–7.75 (m, 3H), 7.62 (d, J=7.6 Hz, 1H), 7.26 (t, J=7.6 Hz, 1H), 4.87 (s, 2H), 2.75 (t, J=7.2 Hz, 2H), 2.54 (t, J=7.4 Hz). HPLC (40–90), 17.23 min. LRMS (EI−) calc'd for [C$_{16}$H$_{13}$I$_3$O$_3$+CF$_3$COO] 746.8, found 746.8.

EXAMPLE 5

Synthesis of (4-Hydroxy-3-iodo-5-nitrophenyl)-phenyl-methanone

A solution of 4-hydroxybenzophenone (1.98 g, 10 mmol), iodine (10.15 g, 40 mmol), and concentrated nitric acid (5 mL) in 100 mL methanol was stirred for 72 hours at room temperature. Hydrogen peroxide, 30% (4.1 mL, 40 mmol) was then added, and the solution was stirred for another 15 hours. The solvent and excess iodine was removed in vacuo, and the crude product was crystallized from methanol, yielding the title compound as bright orange crystals (2.80 g, 76%). $^1$H NMR (400 MHz, CDCl$_3$): δ 11.70 (s, 1H), 8.61 (d, J=2.4 Hz, 1H), 8.57 (d, J=2.4 Hz, 1H), 7.75 (d, J=8.0 Hz, 2H), 7.67 (t, J=7.4 Hz, 1H), 7.55 (appar. t, J=7.6 Hz, 2H). HPLC (40–90), 12.60 min.

EXAMPLE 6

Synthesis of (4-Hydroxy-3,5-diiodophenyl)-phenyl-methanone

To a stirred solution of 4-hydroxybenzophenone (6.51 g, 32.8 mmol) and TRIS (42.0 g, 347 mmol) in 100 mL water was added dropwise over 4 hours by addition funnel a solution of iodine (16.7 g, 65.8 mmol) and potassium iodide (16.5 mmol, 99.4 mmol) in 85 mL water. The solution was acidified to pH ~1 with conc. HCl and solids formed. The brown powder was isolated by filtration and was dissolved in hot isopropanol and was filtered hot to remove insolubles. Crystals developed in the isopropanol solution, yielding the title compound as wheat-colored crystals (9.97 g, 67%). $^1$H NMR (400 MHz, CDCl$_3$): δ 8.16 (s, 2H), 7.75–7.73 (m, 2H), 7.62 (tt, J=7.4, 1.2 Hz, 1H), 7.53–7.49 (m, 2H), 6.19 (s, 1H). HPLC (40–90), 14.38 min. TLC (95:5:0.5 CH$_2$Cl$_2$:MeOH:AcOH), R$_f$ 0.76. LRMS (EI+) calc'd for [C$_{13}$H$_8$I$_2$O$_2$+H] 450.9, found 450.8.

EXAMPLE 7

Synthesis of (4-Benzoyl-2,6-diiodophenoxy)-acetic Acid Benzyl Ester

To a solution of (4-hydroxy-3,5-diiodophenyl)-phenyl-methanone (as prepared in Example 6, 2.25 g, 5.0 mmol) and benzyl 2-bromoacetate (1.71 g, 7.5 mmol) in 50 mL DMF was added cesium carbonate (4.1 g, 13 mmol). The resulting suspension was stirred for 15 hours, then the reaction mixture was poured into ~150 mL 1 M HCl. A pale oil formed, and the supernatant was removed by decantation. The oil was crystallized from hot isopropanol, yielding the title compound as colorless crystals (1.13 g, 38%). $^1$H NMR (400 MHz, CDCl$_3$): δ 8.18 (s, 2H), 7.77–7.74 (m, 2H), 7.63 (tt, J=7.4, 1.2 Hz, 1H), 7.54–7.50 (m, 2 H), 7.45–7.35 (m, 5H), 5.33 (s, 2H), 4.71 (s, 2H). TLC (4:1 Hex:EtOAc), R$_f$ 0.52. LRMS (EI+) calc'd for [C$_{22}$H$_{16}$I$_2$O$_4$+H] 598.9, found 598.8.

EXAMPLE 8

Synthesis of (4-Benzoyl-2,6-diiodophenoxy)-acetic Acid

A 1.2 M solution of lithium hydroxide (1.5 mL, 1.8 mmol) was added to a solution 4-benzoyl-2,6-diiodophenoxy)-acetic acid benzyl ester (as prepared in Example 7,900 mg, 1.5 mmol) in 12 mL THF. The biphasic solution was stirred for 15 hours, then was poured into 1 M HCl. The resulting oil was extracted with ether, and the organic phase was dried over sodium sulfate and concentrated to an oil in vacuo. The oil was crystallized from isopropanol, yielding the title compound as a white powder (722 mg, 94%). $^1$H NMR (400 MHz, DMSO-d$_6$): δ 13.17 (br. s, 1H), 8.09 (s, 2H), 7.75–7.69 (m, 3H), 7.61–7.57 (m, 2H), 4.54 (s, 2H). HPLC (40–90), 12.07 min. LRMS (EI−) calc'd for [C$_{15}$H$_{10}$I$_2$O$_4$—H] 506.9, found 506.6.

EXAMPLE 9

Synthesis of bis-(4-Hydroxy-3,5-diiodophenyl)-methanone

To a stirred solution of 4,4'-dihydroxybenzophenone (3.51 g, 16.4 mmol) and TRIS (19.9 g, 164 mmol) in 50 mL water was added dropwise via addition funnel a solution of iodine (16.6 g, 65.6 mmol) and potassium iodide (16.6 g, 100 mmol) in 75 mL water. The resulting mixture was stirred for 15 hours, then was acidified to pH ~1 with conc. HCl. The resulting pale yellow precipitate was isolated by filtration, then was triturated with hot isopropanol and was filtered and dried in vacuo, yielding the title compound as a pale cream powder (10.88 g, 93%).$^1$H NMR (400 MHz, DMSO-d$_6$): δ 10.44 (br. s, 2H), 8.02 (s, 4H). HPLC (40–90), 15.57 min. LRMS (EI−) calc'd for [C$_{13}$H$_6$I$_4$O$_3$—H] 716.6, found 716.6.

EXAMPLE 10

Synthesis of [4-(4-Hydroxy-3,5-diiodobenzoyl)-2,6-diiodo-phenoxy]-acetic Acid Benzyl Ester A solution of bis-(4-hydroxy-3,5-diiodophenyl)-methanone (prepared according to Example 9, 3.59 g, 5.0 mmol) and benzyl 2-bromoacetate (1.15 g, 5.0 mmol) in 20 mL DMAc was stirred with cesium carbonate (3.3 g, 10 mmol) for 14 hours. Next was added 1 M HCl, and a yellow oil formed along with a hazy white precipitate. The precipitate was isolated by filtration and was recrystallized from hot isopropanol/chloroform, yielding the title compound as colorless crystals (98 mg, 2.2%). No attempt was made to isolate more product from the oil. $^1$H NMR (400 MHz, CDCl$_3$): δ 8.11 (s, 2H), 8.10 (s, 2H), 7.45–7.35 (m, 5H), 6.22 (s, 1H), 5.33 (s, 2H), 4.72 (s, 2H). HPLC (40–90), 19.17 min. (EI-) calc'd for [C$_{22}$H$_{14}$I$_4$O$_5$—H] 864.7, found 864.6.

EXAMPLE 11

Synthesis of of [4-(4-Hydroxy-3,5-diiodobenzoyl)-2,6-diiodo-phenoxy]-acetic Acid A 1.2 M solution of lithium hydroxide (100pL, 0.12 mmol) was added to a solution of [4-(4-hydroxy-3,5-diiodobenzoyl)-2,6-diiodo-phenoxy]-acetic acid benzyl ester (prepared according to Example 10, 50 mg, 0.043 mmol) in 1 mL THF. The biphasic solution was stirred for 6 hours, after which time 1 M HCl was added. The resulting white precipitate was isolated by filtration, rinsed with water, and dried in vacuo, yielding the title compound as a white powder (42 mg, 94%). $^1$H NMR (400 MHz, DMSO-d$_6$): δ 13.18 (br. s, 1H), 10.57 (br. s, 1H), 8.06 (s, 2H), 8.03 (s, 2H), 4.55 (s, 2H). HPLC (40–90), 12.41 min. LRMS (EI-) calc'd for [C$_{15}$H$_8$I$_4$O$_5$—H] 744.6, found 744.8.

EXAMPLE 12

Synthesis of [4-(4-Benzyloxycarbonylmethoxy-3,5-diiodo-benzoyl)-2,6-diiodo-phenoxy]-acetic Acid Benzyl Ester To a solution of bis-(4-hydroxy-3,5-diiodophenyl)-methanone (prepared according to Example 9, 718 mg, 1.0 mmol) and benzyl 2- bromoacetate (504 mg, 2.2 mmol) in 10 mL DMF was added cesium carbonate (980 mg, 3.0 mmol). The suspension was stirred for 23 hours, then 1 M HCl was added. The pale yellow precipitate was isolated by filtration and triturated with hot isopropanol, then dried in vacuo, yielding the title compound as a pale yellow powder (550 mg, 54%). $^1$H NMR (400 MHz, CDC$_{l3}$): δ 8.12 (s, 4H), 7.42–7.37 (m, 10H), 5.33 (s, 4H), 4.72 (s, 4H). TLC (5:1 CH$_2$Cl$_2$:Hex), R$_f$ 0.21.

EXAMPLE 13

Synthesis of [4-(4-Carboxymethoxy-3,5-diiodo-benzoyl)-2,6-diiodophenoxy]-acetic Acid A 1.2 M solution of lithium hydroxide (300 μL, 0.36 mmol) was added to a solution of [4-(4-benzyloxycarbonylmethoxy-3,5-diiodo-benzoyl)-2,6-diiodo-phenoxy]-acetic acid benzyl ester (prepared according to Example 12, 76 mg, 0.075 mmol) in 2.4 mL THF. The suspension was stirred for 48 hours, after which time the mixture was poured into 1 M HCl. The resulting white precipitate was isolated by filtration, rinsed with water, and dried in vacuo, yielding the title compound as a white powder (52 mg, 83%). $^1$H NMR (400 MHz, DMSO-d$_6$): δ 13.17 (br. s, 2H), 8.09 (s, 4H), 4.55 (s, 4H). HPLC (40–90), 10.29 min. LRMS (EI-) calc'd for [C$_{17}$H$_{10}$I$_4$O$_7$—H] 832.7, found 832.6.

EXAMPLE 14

Synthesis of 4-Hydroxy-3,5-diiodobenzoic acid 2-iodobenzyl Ester

A suspension of 3,5-diiodo-4-hydroxybenzoic acid (1 95 mg, 0.5 mmol, 2-iodo benzyl chloride (320 mg, 1.25 mmol), and cesium carbonate (490 mg, 1.5 mmol) in 5 mL DMF was stirred for 15 hours at room temperature. The mixture was then poured into 1 M HCl (100 mL) and a white precipitate formed. The precipitate was isolated filtration and was recrystallized from hot isopropanol/chloroform, yielding the title compound as bright white crystals (140 mg, 61%). $^1$H NMR (400 MHz, CDC$_{l3}$): δ 8.40 (s, 2H), 7.90 (dd, J=8.0, 1.2 Hz, 1H), 7.44–7.36 (m, 2H), 7.06 (td, J=8.0, 2.0 Hz, 1H), 6.14 (s, 1H), 5.35 (s, 2H).

EXAMPLE 15

Synthesis of 1,2-bis-(4-Hydroxy-3,5-diiodophenyl)-ethane-1,2-dione

To a stirred solution of 4,4'-dihydroxybenzil (3.97 g, 16.4 mmol) and TRIS (19.9 g, 164 mmol) in 50 mL water was added dropwise via addition funnel over 45 min. a solution of iodine (16.6 g, 65.4 mmol) and potassium iodide (16.6 g, 100 mmol) in 75 mL water. The resulting dark brown solution was stirred for 18 hours, during which time bright yellow solids formed. The reaction mixture was diluted with water and was acidified to pH <3 with conc. HCl. The resulting brown solids were isolated by filtration and were rinsed with isopropyl alcohol, removing such of the color. Trituration of the solids with 5:1 acetone/water yielded the title compound as a white solid (9.72 g, 80%). $^1$H NMR (400 MHz, DMSO-d$_6$): δ 8.22 (s, 4H). HPLC (40–90), 13.54 min. LRMS (EI-) calc'd for [C$_{14}$H$_6$I$_4$O$_4$—H] 744.6, found 744.6.

EXAMPLE 16

Synthesis of (4-Fluorophenyl)-(4-hydroxy-3,5-diiodophenyl)-methanone

To a stirred solution of 4-fluoro-4'-hydroxybenzophenone (4.32 g, 20.0 mmol) and TRIS (12.1 g, 100.0 mmol) in 80 mL water was added dropwise via addition funnel over 1 hour a solution of iodine (10.15 g, 40.0 mmol) and potassium iodide (9.96 g, 60.0 mmol) in 100 mL water. The resulting solution was stirred for 14 hours, during which time a thick yellow precipitate formed. The reaction mixture was poured into dilute HCl solution and was stirred vigorously for 2 hours. The resulting white solids were isolated by filtration from the yellow solution and were rinsed with 1 M HCl, then were recrystallized from isopropanol/dilute HCl, yielding the title compound as colorless crystals (7.62 g, 81%). $^1$H NMR (400 MHz, CDCl$_3$): δ 8.13 (s, 2H), 7.80–7.66 (m, 2H), 7.21–7.17 (m, 2H), 6.18 (s, 1H). HPLC (40–90), 11.20 min. LRMS (EI-) calc'd for [C$_{13}$H$_7$FI$_2$O$_2$—H] 466.9, found 466.8.

EXAMPLE 17

Synthesis of {4-[(4-Hydroxy-3,5-diiodophenyl)-oxo-acetyl]-2,6-diiodo-phenoxy}-acetic Acid Benzyl Ester Cesium carbonate (1.30 g, 4.0 mmol) was suspended in a solution of 1,2-bis-(4-hydroxy-3,5-diiodophenyl)-ethane-1,2-dione (as prepared in Example 15, 1.49 g, 2.0 mmol) and benzyl 2-bromoacetate (0.46 g, 2.0 mmol) in 8 mL DMF. The mixture was stirred at RT for 16 hours and was poured into 1 M HCl. The resulting precipitate was isolated by filtration, then was dissolved in hot chloroform and filtered through Celite. The solvent was removed by rotary evaporation, and the crude material was purified by silica gel column chromatography (5% MeOH in CH$_2$Cl$_2$), yielding the title compound as a yellow powder (258 mg, 14%). $^1$H NMR (400 MHz, DMSO-d$_6$): δ 8.30 (s, 2H), 8.23 (s, 2H), 7.45–7.34 (m, 5H), 5.27 (s, 2H), 4.73 (s, 2H). HPLC (50–90), 15.74 min. LRMS (EI–) calc'd for [$C_{23}H_{14}I_4O_6$—H] 893.0, found 892.6.

EXAMPLE 18

Synthesis of {4-[(4-hydroxy-3,5-diiodophenyl )-oxo-acetyl]-2,6-diiodo-phenoxy}-acetic Acid A 1.2 M solution of LIOH (100 μL, 0.12 mmol) in water was added to a solution of {4-[4-hydroxy-3,5-diiodophenyl)-oxo-acetyl]-2,6-diiodo-phenoxy}-acetic acid benzyl ester (as prepared in Example 17, 45 mg, 0.05 mmol) in 1 mL THF. The solution was stirred for 64 hours, then 1 M HCl solution was added to the mixture. The resulting precipitate was isolated by filtration and dried in vacuo, yielding the title compound as a pale yellow powder (34 mg, 84%). $^1$H NMR (400 MHz, DMSO-$d_6$): δ 13.0 (br.s, 1H), 8.30 (s, 2H), 8:24 (s, 2H), 4.55 (s, 2H). HPLC (40–90), 11.52 min. LRMS (EI–) calc'd for [$C_{16}H_8I_4O_6$—H] 802.8, found 802.5.

EXAMPLE 19

Synthesis of 3,3',5,5'-Tetraiodo-4,4'-sulfonyidiphenol

To a stirred solution of 4,4'-sulfonyldiphenol (2.50 g, 10.0 mmol) and TRIS (12.1 g, 100.0 mmol) in 100 mL water was added dropwise via addition funnel over 1 hour a solution of iodine (10.15 g, 40.0 mmol); and potassium iodide (9.96 g, 60.0 mmol) in 100 mL water. The resulting amber solution was stirred for 14 hours, during which time a pale precipitate formed. The reaction mixture was acidified with conc. HCl and the resulting pale yellow solids were isolated by filtration. Trituration of the solids with hot isopropanol yielded the title compound as a bright white powder (7.01 g, 93%). $^1$H NMR (400 MHz, DMSO-$d_6$): δ 10.75 (br. s, 2H), 8.29 (s, 4H). HPLC (40–90), 9.91 min. LRMS (EI–) calc'd for [$C_{12}H_6I_4O_4S$—H] 752.6, found 752.2.

EXAMPLE 20

Synthesis of 5,7-Dihydroxy-6,8-diiodo-2-phenyl-chromen-4-one

Chrysin (5.17 g, 20.3 mmol), sodium hydroxide (1.66 g, 41.5 mmol) and sodium iodide (6.13 g, 40.8 mmol) were dissolved in methanol (150 ml) with vigorous stirring. The resulting mixture was cooled to 0° C. and aqueous sodium hypochlorite (150 ml, 5.25%) was added dropwise over 1 hour. The mixture was stirred for an additional hour at 0° C. The reaction was quenched by the dropwise addition of aqueous $Na_2S_2O_3$ (200 ml, 5%). The mixture was adjusted to pH 7 with 1M hydrochloric acid. The resulting precipitate was filtered and washed with several volumes of water to remove excess chlorite. The solid is dried under vacuum to give 8.0 g (77%) of the title compound. $^1$H NMR (400 MHz, $d_6$-DMSO) δ 8.19 (d, 2H, J=8.4 Hz), 7.61 (dd, 3H, J=8 Hz), 7.18 (d, 1H, J=4 Hz). LR-MS neg. calc'd (M-H) 505.03 found 504.6.

EXAMPLE 21

Synthesis of 3-N-Benzyl-4-(1H-tetrazol-5-yl)-2,6-diodophenol

A. 4-(1H-Tetrazol-5-yl)phenol

A 50 mL round bottomed flask equipped with a Teflon coated magnetic stirring bar, and a rubber septum was charged with 4-cyanophenol (596 mg, 5.0 mmol), sodium azide (975 mg, 15 mmol), triethylamineo.HCl (2.06 g, 15 mmol) and toluene (25 mL). The reaction mixture was heated at 100° C. for 18 h with vigorous stirring. The reaction mixture was cooled to ambient temperature and poured into a separatory funnel and extracted with $H_2O$ (3×10 mL). The combined aqueous phases were treated dropwise with HCl (conc.) to precipitate the product from the reaction mixture. The precipitate was collected by vacuum filtration and dried under vacuum to afford the title compound as an off-white solid (890 mg, 94%).

B. 3-N-Benzyl-4-(1H-tetrazol-5-yl)phenol

A 20 mL round bottomed flask equipped with a Teflon coated magnetic stirring bar, a rubber septum and a reflux condenser was charged with acetone (25 mL), 4-(2H-tetrazol-5-yl)phenol (50 mg, 0.31 mmol) and $K_2CO_3$ (213 mg, 1.54 mmol). The reaction mixture was treated with benzylbromide (37 μL, 0.31 mmol) and heated at 50° C. for 18 h. The reaction mixture was cooled to ambient temperature and filtered to remove the $K_2CO_3$ and the filtrate was concentrated to dryness. The resulting residue was triturated with 3 M aqueous NaOH and extracted with ethyl acetate. The aqueous phase was separated and treated with HCl (conc.). The precipitate was collected and subjected to flash chromatography (SiO2, 30% ethyl acetate/hexane) to afford the title product as a white solid (57 mg, 74%). This procedure was repeated on a 3 g scale in 50% yield.

C. 3-N-Benzyl-4-(1H-tetrazol-5-yl)-2,6-diodophenol

A 25 mL three necked round bottomed flask equipped with a Teflon coated magnetic stirring bar, thermometer and a rubber septum was charged with MeOH (10 mL), NaOH (48 mg, 1.19 mmol), NaI (178 mg, 1.19 mmol), and (1H-tetrazole-5-yl)phenol (150 mg, 0.60 mmol). The reaction mixture was treated with NaOCl (2.20 mL, 1.20 mmol) drop wise via syringe at or below 0° C. After the addition was complete the reaction mixture was vigorously stirred at 0° C. for 2 h. The reaction mixture was then treated with $Na_2S_2O_3$ (10 mL) and stirred for 15 min. The pH was adjusted with HCl (conc.) to a pH of ~5 (if the pH falls below 5 it does not seem to have adverse effects on the yield). The product precipitates from the solution and was collected by vacuum filtration. The precipitate was dried under high vacuum (24 h) to give the title compound as an off white solid (279 mg, 93%).

EXAMPLE 22

Synthesis of 2,6-Dichloro-4-(4'-phenylethynyl) phenol

A 50 mL round bottomed flask equipped with a Teflon coated magnetic stirring bar and a rubber septum was charged with diisopropylamine (20 mL) and flushed with $N_2$. CuI (23 mg, 0.13 mmol) and P(PPh$_3$)$_4$ (43 mg, 0.04 mmol) were added and stirred for 5 min followed by the addition of 2,6-dichloro-4-iodophenol (20 mg, 1.83 mmol) in one portion. After stirring for 15 min phenylacetylene (204 mg, 2.0 mmol) was added and stirred at ambient temperature for 18 h. A 1:1 solution (10 mL) of sat. $NH_4Cl$ and sat $K_2CO_3$ were added to the reaction mixture followed by the addition of water (20 mL). The resulting solution was extracted with ethyl acetate (3×20 mL) and the combined organic phases were washed with brine, dried (MgSO$_4$), filtered and concentrated. The yellow residue was triturated with hexane and the precipitate was collect and washed several times with hexane to give the triethylamine salt of the title compound (483 mg, 72%). The free phenol was prepared by dissolving the salt into ethyl acetate and adding 1N HCl. The heterogeneous mixture was stirred vigorously at ambient temperature for 30 min. The biphasic mixture was poured into a separatory funnel and phases were separated. The organic phase was washed with water, brine, dried (MgSO$_4$), filtered and concentrated to give the title compound as a light tan solid (327 mg, 68%).

EXAMPLE 23

Synthesis of 3-(4-Hydroxy-3,5-diodo-benzylidene)-1,3-dihydroindol-2-one

A 100 mL round bottomed flask equipped with a Teflon coated magnetic stirring bar, a reflux condenser and a rubber septum was charged with ethanol (25 mL), 2,6-diidohydroxybenzaldehyde (1.48 g, 3.94 mmol), oxindole (0.5 g, 3.76 mmol) and piperidine (0.37 mL, 4.0 mmol). The reaction mixture was heated at reflux temperatures for 6 h with stirring. The reaction mixture was cooled in the freezer overnight and the precipitate was collected by vacuum filtration to give the title compound as a yellow solid (1.69 g, 92%, mixture of isomers 4:1 E/Z).

EXAMPLE 24

Synthesis of 3-(4-Hydroxy-3,5-diiodo-phenyl)-acrylic Acid Methyl Ester

A 50 mL round bottomed flask equipped with a Teflon coated magnetic stirring bar, a reflux condenser and a rubber septum was charged with 3,5-diiodo-4-hydroxybenzaldehyde (1 g, 2.68 mmol), methyl (triphenylphosphoranylidene) acetate (1.79 g, 5.36 mmol) and benzene (30 mL). The reaction mixture was heated to a gentle reflux for 24 h. The reaction mixture was cooled to ambient temperature and concentrated to dryness. The title compound obtained was a white solid (891 mg, 78%) after the crude material was subjected to flash chromatography (SiO$_2$, using 20% EtOAc/Hex as the eluent).

EXAMPLE 25

Synthesis of 2,6-Diiodo-4-octylphenol

A 100 mL round bottomed flask equipped with a Teflon coated magnetic stirring bar and a rubber septum was charged with NaOH (85 mg, 2.1 mmol), NaI (0.64 g, 4.2 mmol), 4-octylphenol (0.5 g, 2.1 mmol) and MeOH (20 mL) The reaction mixture was cooled to 0° C. and treated drop wise with a 4% aqueous solution of NaOCl (8 mL) over a 45 min period (the temperature was maintained at or below 0° C.). Once the addition was complete the reaction was stirred for an additional 1 h at 0° C. The reaction mixture was then treated with 10% Na$_2$S$_2$O$_3$ (20 mL) and stirred for 20 min after which time the pH was adjusted to 3–4 with HCl (conc.). The reaction mixture was extracted with EtOAc (3×25 mL) and the organic phases were combined and washed with brine, dried (MgSO$_4$), filtered and concentrated to give a yellow oil. Recrystallization of the crude material from hexane afforded the title compound as colorless crystals (0.55 g, 42%).

EXAMPLE 26

Synthesis of 4'-Hydroxy-3',5'-diiodobiphenyl-4-nitrile

A 100 mL round bottomed flask equipped with a Teflon coated magnetic stirring bar and a rubber septum was charged with a suspension of 4'-hydroxybiphenyl-4-nitrile (0.98 g, 0.5 mmol) and a solution of 1M TRIZMA® Base (25 mL, 25 mmol). The suspension was treated drop wise with a stock solution (25 mL) of KI (0.6 M)/I$_2$ (0.4 M) in H$_2$O over a 1 h period via addition funnel. The reaction mixture was stirred for 18 h and poured into 1M HCl (aq)(25 mL) and stirred vigorously for 2 h and poured into a separatory funnel containing EtOAc (25 mL). The phases were separated and the aqueous phase was re-extracted with EtOAc (2×25 mL). The organic phases were combined and washed with 1N HCl, 10% Na$_2$S$_2$O$_3$, H$_2$O, brine, dried (MgSO4), filtered and concentrated to give a yellow powder. The crude material was recrystallized (2x) from CH$_2$Cl$_2$ to afford the title compound as a white powder (1.3 g, 59%).

EXAMPLE 27

Synthesis of 4-[2-(4-Bromophenyl)-2-oxoethoxy]-3,5-diiodobenzoic Acid

A 25 mL round bottomed flask equipped with a Teflon coated magnetic stirring bar and a rubber septum was charged with 4-hydroxy-3,5-diiodo-1-benzoic acid (195 mg, 0.5 mmol), Cs$_2$CO$_3$ (489 mg) and DMF (5 mL). 2,4'-dibromoacetophenone (347 mg, 1.25 mmol) was added to the reaction mixture and stirred 18 h at ambient temperature. The reaction mixture was poured into 1 N HCl (10 mL) and stirred for 0.5 h. The precipitate was collected by vacuum filtration and recrystallized from CH$_3$Cl and a minimal amount of isopropanol to provide 4-[2-(4-bromo- 1-phenyl)-2-oxo-ethoxy]-3,5-diiodobenzoic acid 2-(4-bromophenyl)-2-oxoethyl ester as a tan solid (365 mg, 90%). 4-[2-(4-bromo-1-phenyl)-2-oxo-ethoxy]-3,5-diiodobenzoic acid 2-(4-bromophenyl)-2-oxoethyl ester (63 mg) was dissolved in THF (1.5 mL) and treated with stock solution of 1.2 M LiOH (aq) (176 µL, 0.21 mmol). The reaction mixture was stirred for 18 h and 0.5N HCl (4 mL). The precipitate was collected by vacuum filtration and recrystallized from CH$_3$Cl/ispropanol to afford the title compound as a light tan solid (18 mg, 32%).

EXAMPLE 28

Other compounds provided herein were prepared by minor modification of the processes for preparation set forth in the previous Examples 1–27. Analytical data for some of these compounds is provided in the following table.

TABLE

| COMPOUND | $^1$H NMR (SOLVENT) | MASS SPECTRUM |
|---|---|---|
| 3,5-diiodo-4-(3-iodo-benzyloxy)- benzoic acid | DMSO: 8.33(s, 2H), 7.98(s, 1H), 7.77(d, J=8.0 Hz, 1H), 7.64(d, J= 7.6 Hz, 1H), 7.28(appar. t, J= 7.8 Hz, 1H), 4.97(s, 2H) | 718.6 (M + TFA) |
| 3,5-diiodo-4-(4-iodo-benzyloxy)- benzoic acid | DMSO: 8.33(s, 2H), 7.83(d, J= 8.4 Hz, 2H), 7.42(d, J=8.0 Hz, 2H), 4.95(s, 2H) | 604.2 (M − H), 718.8 (M + TFA) |
| 3,5-diiodo-4-(2-bromo-benzyloxy)- benzoic acid | DMSO: 13.37(br. s, 1H), 8.34(s, 2H), 7.85(d, J=7.6 Hz, 1H), 7.69 (d, J=8.0 Hz, 1H), 7.52(appar. t, J=7.6 Hz, 1H), 7.35(appar. t, J= 7.6 Hz, 1H), 5.08(s, 2H) | 556.6 (M − H), 670.6(M + TFA) |
| 3,5-diiodo-4-(3-bromo-benzyloxy)- benzoic acid | DMSO: 13.39(br. s, 1H), 8.33(s, 2H), 7.81(s, 1H), 7.63–7.61(m, 2H), 7.44(appar. t, J=7.8 Hz, 1H), 5.00(s, 2H) | 556.6 (M − H), 670.6(M + TFA) |

TABLE-continued

| COMPOUND | ¹H NMR (SOLVENT) | MASS SPECTRUM |
|---|---|---|
| 3,5-diiodo-4-(4-bromo-benzyloxy)- benzoic acid | DMSO: 13.39(br. s, 1H), 8.33(s, 2H), 7.67(d, J=7.6 Hz, 2H), 7.57 (d, J=8.0 Hz, 2H), 4.98(s, 2H) | 556.8 (M − H), 672.4 (M + TFA) |
| 3,5-diiodo-4-(2-methyl-benzyloxy)- benzoic acid | DMSO: 13.38(br. s, 1H), 8.34(s, 2H), 7.69(d, J=6.8 Hz, 1H), 7.30–7.24(m, 3H), 5.02(s, 2H), 2.45(s, 3H) | 492.8 (M − H), 606.6(M + TFA) |
| 3,5-diiodo-4-(3-methyl-benzyloxy)- benzoic acid | DMSO: 13.37(br. s, 1H), 8.33(s, 2H), 7.44–7.43(m, 2H), 7.34 (appar.t, J=7.4 Hz, 1H), 7.22(d, J=7.6 Hz, 1H), 4.95(s, 2H), 2.36(s, 3H) | 492.6(M − H), 606.6 (M + TFA) |
| 3,5-diiodo-4-(4-methyl-benzyloxy)- benzoic acid | DMSO: 13.38(br. s, 1H), 8.33(s, 2 H), 7.52(d, J=7.6 Hz, 2H), 7.26 (d, J=7.6 Hz, 2H), 4.94(s, 2H), 2.35(s, 3H) | 492.6 (M − H) |
| 4-(4-tert-butyl-benzyloxy)-3,5-diiodo-benzoic acid | DMSO: 13.38(br. s, 1H), 8.33(s, 2 H), 7.56(d, J=8.0 Hz, 2H), 7.47 (d, J=8.0 Hz, 2H), 4.94(s, 2H), 1.31(s, 9H) | — |
| 3,5-diiodo-4-(naphthalen-2-ylmethoxy)-benzoic acid | DMSO: 13.37(br. s, 1H), 8.36(s, 2H), 8.12(s, 1H), 8.03–7.96(m, 3H), 7.80(d, J=8.4 Hz, 1H), 7.59–7.55(m, 2H), 5.18(s, 2H) | 528.8(M − H), 642.6 (M + TFA) |
| 4-(biphenyl-2-ylmethoxy)-3,5-diiodo- benzoic acid | DMSO: 13.35(br. s, 1H), 8.26(s, 2H), 7.93(d, J=8 Hz, 1H), 7.52–7.31(m, 8H), 4.99(s, 2H) | 554.6(M − H), 668.6 (M + TFA) |
| 3,5-diiodo-4-(3-methoxy-benzyloxy)- benzoic acid | DMSO: 13.38(br. s, 1H), 8.33(s, 2H), 7.37(appar. t, J=7.8 Hz, 1H), 7.22(br. s, 1H), 7.17(d, J=7.6 Hz, 1H), 6.99–6.96(m, 1H), 4.96(s, 2H), 3.80(s, 3H) | 508.8(M − H), 622.6 (M + TFA), 1018.6 (2M + H) |
| 3,5-diiodo-4-(3-trifluoromethyl-benzyloxy)-benzoic acid | DMSO: 13.42(br. s, 1H), 8.34(s, 2H), 7.95–7.92(m, 2H), 7.79(d, J=7.6 Hz, 1H), 7.72(appar. t, J=7.6 Hz, 1H), 5.11(s, 2H) | 546.4(M − H), 660.6 (M + TFA), 1094.6 (2M + H), 1208.6 (2M + TFA) |
| 3,5-diiodo-4-(3-trifluoromethoxy-benzyloxy)-benzoic acid | DMSO: 13.39(br. s, 1H), 8.33(s, 2H), 7.64–7.59(m, 3H), 7.42–7.40 (m, 1H), 5.05(s, 2H) | — |
| 4-(3-fluoro-benzyloxy)-3,5-diiodo-benzoic acid | DMSO: 13.41(br. s, 1H), 8.33(s, 2H), 7.54–7.43(m, 3H), 7.27–7.22 (m, 1H), 5.02(s, 2H) | 496.6(M − H), 610.8 (M + TFA), 994.6 (2M + H) |
| 3,5-diiodo-4-pentafluoro-phenylmethoxy-benzoic acid | DMSO: 13.42(br. s, 1H), 8.31(s, 2H), 5.20(s, 2H) | 568.8(M − H), 682.6 (M + TFA), 1138.4 (2M + H) |
| 3,5-dibromo-4-(3-iodo-benzyloxy)-benzoic acid | DMSO: 13.53(br. s, 1H), 8.14(s, 1H), 7.93(s, 1H), 7.77(d, J=8.0 Hz, 1H), 7.60(d, J=6.8 Hz, 1H), 7.26(t, J=7.8 Hz, 1H), 5.04(s, 2H) | 510.6(M − H), 624.6 (M + TFA) |
| 3,5-dichloro-4-(3-iodo-benzyloxy)-benzoic acid | DMSO: 13.58(br. s, 1H), 7.97(s, 1H), 7.91(s, 1H), 7.76(d, J=7.6 Hz, 1H), 7.60(d, J=7.6 Hz, 1H), 7.24(t, J=7.8 Hz, 1H), 5.09(s, 2H) | 420.6(M − H), 471.0 (M + TFA) |
| 3-[3,5-diiodo-4-(4-iodo-benzyloxy)-phenyl]-propionic acid | DMSO: 12.16(s, 1H), 7.82(d, J= 7.6 Hz, 2H), 7.76(s, 2H), 7.40(d, J=8.0 Hz, 2H), 4.86(s, 2H), 2.75 (t, J=7.4 Hz, 2H), 2.54(t, J=7.4 Hz, 2H) | 746.8 (M + TFA) |
| 3-(4-benzyloxy-3,5-diiodo-phenyl)-propionic acid | DMSO: 12.15(s, 1H), 7.77(s, 2H), 7.62(d, J=8.0 Hz, 2H), 7.47–7.39 (m, 3H), 4.90(s, 2H), 2.75(t, J= 7.4 Hz, 2H), 2.54(t, J=7.4 Hz, 2H) | 620.8 (M + TFA) |
| 3-[4-(3-bromo-benzyloxy)-3,5-diiodo-phenyl]-propionic acid | DMSO:12.13(br. s, 1H), 7.79–7.76 (m, 3H), 7.61–7.59(m, 2H), 7.42 (appar. t, J=7.8 Hz, 1H), 4.91(s, 2H), 2.75(t, J=7.4 Hz, 2H), 2.54 (t, J=7.4 Hz, 2H) | 700.8 (M + TFA) |
| 3-[4-(4-bromo-benzyloxy)-3,5-diiodo-phenyl]-propionic acid | DMSO: 12.14(br. s, 1H), 7.76(s, 2H), 7.65(d, J=8.0 Hz, 2H), 7.55 (d, J=8.0 Hz, 2H), 4.88(s, 2H), 2.75(t, J=7.4 Hz, 2H), 2.54(t, J=7.4 Hz, 2H) | 700.8 (M + TFA) |

EXAMPLE 29

Assays for Plasminogen Activator Inhibitor Type-1 Antagonism

Compounds provided herein for use in the compositions and methods can be and have been tested for PAI antagonist activity in any assay known to those of skill in the art. See, e.g., Madison et al. (1989) Nature 339:721–723; Madison et al. (1990) Proc. Natl. Acad. Sci. USA 87:3530–3533; Madison et al. (1993) Science 262:419–421; Chariton et al. (1997) Fibrinolysis & Proteolysis 11(1):51–56; Chariton et al. (1996) Thrombosis and Haemostasis 75(5):808–815; and U.S. Pat. Nos. 5,750,530, 5,891,877 and 5,902,812.

Reagents

PAI-1 antagonist assays were performed in a buffer containing Tris, 0.05 mol/L, pH 7.4, 100 mmol/L NaCl, 1 mmol/L EDTA, and 0.01% Tween 80. Human recombinant PAI-1 purified from *E coli*. and human recombinant tPA were diluted into this standard assay buffer at concentrations of approximately 500–600 ng/mL and 100 ng/mL, respectively. PAI-1 antagonists were dissolved first in DMSO at a concentration of approximately 5 mg/mL, and these solutions were then diluted into the standard reaction buffer to achieve a final compound concentration of 1 mg/mL. Native, purified human glu-plasminogen was purchased from Boehringer Mannheim and was supplied as a lyophilized powder, which was first reconstituted in sterile water to a concentration of 55 µmol/L and then diluted to a concentration of 0.825 µmol/L in standard assay buffer. The chromogenic substrate Spectrozyme PL (H—D-Norleucyl-hexahydrotyrosyl-lysine-p-nitroanilide, American Diagnostica) was prepared as a stock solution with a concentration of 2.5 mmol/L in sterile water. Human fibrin monomer (DESAFIB) was purchased from American Diagnostica and was supplied as a lyophilized powder, which was reconstituted in standard assay buffer at a concentration of 100 µg/mL.

Chromogenic Assay

The chromogenic assay utilized the reagents described above. Fresh reagent solutions were prepared prior to each assay. Assays were performed in individual wells of standard 96 well mocrotiter assay plates. Standard assays were prepared as follows:

Assay #1

The following reagents were combined:

| Test compound | 5 µL |
| PAI-1 | 10 µL |
| tPA | 10 µL |

The plate was agitated or the individual 25 µL mixtures were pipetted up and down once or twice to assure proper mixing of reagents. The resulting mixture was incubated 15 minutes at room temperature (approximately 21° C.).

The following was added to each reaction:

| DESAFIB | 25 µL |
| Glu-plasminogen | 25 µL |
| Spectrozyme PL | 25 µL |

The microtiter assay plate was then placed into a Molecular Devices Thermomax or Spectromax Plate Reader, agitated to assure thorough mixing of reagents, and incubated at 37° C. The $OD_{405}$ of each reaction mixture is measured every minute for 1 hour. Control reactions which lack PAI-1; PAI-1 and test compound; t-PA; or t-PA, PAI-1 and test compound were performed in each assay.

Assay #2

Assay #2 was performed exactly as assay #1 except that a 10 minute preincubation of the test compound and PAI-1 was performed at room temperature prior to the addition of t-PA.

Assay #3

Assay #3 was performed exactly as assay #1 except that a wide range of concentrations of each test compound, depending upon the potency of the individual compound, was used in the assay.

Assay #4

Assay #4 was performed exactly as assay #2 except that a wide range of concentrations of each test compound, depending upon the potency of the individual compound, was used in the assay.

Results

Inhibition of PAI-1 by the compounds provided herein resulted in the production of plasmin from plasminogen. The generated plasmin cleaved the chromogenic substrate, Spectrozyme PL, producing pNA (para-nitroaniline). The pNA was detected spectrophotometrically at 405 nm.

The degree of inhibition at various concentrations and/or the $IC_{50}$ value for the compounds provided herein was determined by comparison with control reactions. The $IC_{50}$ for PAI antagonist activity for each of the compounds specifically disclosed herein has been measured. Almost all of the compounds, including 4-(2,6-difluorobenzyloxy)-3,5-diiodobenzoic acid, (4-hydroxy-3,5-diiodophenyl)-phenyl-methanone and [4-(4-hydroxy-3,5-diiodobenzoyl)-2,6-diiodophenoxy]acetic acid, have an $IC_{50}$ of less than 100 µM. Many of the compounds, including 3,5-diiodo-4-(2-methylbenzyloxy)benzoic acid, bis(4-hydroxy-3,5-diiodophenyl)methanone, 1,2-bis-(4-hydroxy-3,5-diiodophenyl)ethane-1,2-dione and 4-(10-carboxydecyloxy)-3,5-diiodobenzoic acid, have an $IC_{50}$ less than about 50 µM, and some of the compounds, including 3,5-diiodo-4-(4-iodobenzyloxy)benzoic acid, 3-[3,5-diiodo-4-(4-iodobenzyloxy)phenyl]propionic acid and [3,5-diiodo-4-(3-iodobenzyloxy)phenyl]-(4-hydroxy-3,5-diiodophenyl)methanone, have an $IC_{50}$ less than about 10 µM.

Since modifications will be apparent to those of skill in this art, it is intended that this invention be limited only by the scope of the appended claims.

What is claimed is:

1. A compound that has the formula (XIc):

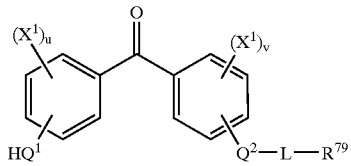

or a pharmaceutically acceptable derivative thereof, wherein:

each $X^1$ is independently selected from halo, pseudohalo, nitro, cyano, alkyl, haloalkyl, aryl or heteroaryl;

$Q^1$ is O, S, S(O), $SO_2$ or $S(O)_2O$;

$Q^2$ is O, S, S(O), $SO_2$, $S(O)_2O$ or $NR^{17}$;

L is a direct link, $CH_2$, $(CH_2)_pC(O)$, $(CH_2)_pC(O)O$ or $(CH_2)_pC(O)NR^{17}$, where p is an integer from 0 to 6;

u is an integer from 0 to 4;

v is an integer from 0 to 4;

where u+v is not 0;

each $R^{17}$ is independently selected from the group consisting of hydrogen, halo, pseudohalo, cyano, azido, nitro, $SiR^{27}R^{28}R^{25}$, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy and $NR^{19}R^{20}$;

$R^{19}$ and $R^{20}$ are each independently selected from hydrogen, alkyl, alkenyl, alkynyl, cycloalkyl, aryl, aralkyl, heteroaryl, heteroaralkyl and heterocyclyl;

$R^{25}$, $R^{27}$ and $R^{28}$ are each independently a monovalent group selected from hydrogen, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy and $NR^{19}R^{20}$;

$R^{17}$, $R^{19}$, $R^{20}$, $R^{25}$, $R^{27}$ and $R^{28}$ may be substituted with one or more substituents each independently selected from $Z^2$, wherein $Z^2$ is selected from alkyl, alkenyl, alkynyl, aryl, cycloalkyl, cycloalkenyl, hydroxy, S(O)$_h$$R^{35}$, $NR^{35}R^{36}$, $COOR^{35}$, $COR^{35}$, $CONR^{35}R^{36}$, OC(O)$NR^{35}R^{36}$, $N(R^{35})C(O)R^{36}$, alkoxy, aryloxy, heteroaryl, heterocyclyl, heteroaryloxy, heterocyclyloxy, aralkyl, aralkenyl, aralkynyl, heteroaralkyl, heteroaralkenyl, heteroaralkynyl, aralkoxy, heteroaralkoxy, alkoxycarbonyl, carbamoyl, thiocarbamoyl, alkoxycarbonyl, carboxyaryl, halo, pseudohalo, haloalkyl and carboxamido;

$R^{35}$ and $R^{36}$ are each independently selected from among hydrogen, halo, pseudohalo, cyano, azido, nitro, trialkylsilyl, dialkylarylsilyl, alkyldiarylsilyl, triarylsilyl, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy, amino, amido, alkylamino, dialkylamino, alkylarylamino, diarylamino and arylamino;

$R^{79}$ is selected as in either (i) or (ii) below:
(i) when L is not a direct link or $CH_2$, $R^{79}$ is hydrogen, alkenyl, alkynyl, $Q^2H$, aryl or heteroaryl; or
(ii) when L is a direct link or $CH_2$, $R^{79}$ is aryl excluding unsubstituted phenyl, heteroaryl, alkenyl or alkynyl.

2. The compound of claim 1 that has formula (XId):

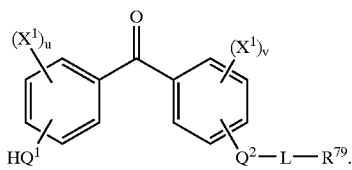

3. The compound of claim 2, wherein $Q^2$-L-$R^{79}$ is 3-iodobenzyloxy, phenoxycarbonylmethoxy, benzyloxycarbonyloxy or 9-fluorenyloxy.

4. The compound of claim 2, wherein each $X^1$ is independently halo, pseudohalo or nitro.

5. The compound of claim 2, wherein $Q^1H$ is OH.

6. A pharmaceutical composition, comprising the compound of claim 1, or a pharmaceutically acceptable derivative thereof, in a pharmaceutically acceptable carrier.

7. The pharmaceutical composition of claim 6 that is formulated for single dosage administration.

8. An article of manufacture, comprising packaging material, a compound of claim 1 or a pharmaceutically acceptable derivative thereof, which is effective for antagonizing a plasminogen activator inhibitor (PAI) or for treatment, prevention or amelioration of one or more symptoms of thrombotic disorders, unstable angina or cancer, and a label that indicates that the compound or pharmaceutically acceptable derivative thereof is used for antagonizing PAI, or for treatment, prevention or amelioration of one or more symptoms of thrombotic disorders, unstable angina or cancer.

9. A method of antagonizing a plasminogen activator inhibitor (PAI), comprising contacting the PAI with a compound of claim 1, or pharmaceutically acceptable derivatives thereof.

10. A method for treating, preventing, or ameliorating one or more symptoms of a plasminogen activator inhibitor (PAI) mediated disorder, comprising administering a compound of claim 1 or a pharmaceutically acceptable derivative thereof.

11. The method of claim 10, wherein the disorder is cancer or a symptom thereof.

12. The method of claim 11 wherein the cancer is selected from the group consisting of tumors, solid tumors, metastatic solid tumors and breast cancer.

13. The method of claim 10, wherein the disorder is a thrombotic disorder, unstable angina or haemostatic disorder.

14. The method of claim 10 that is a method of modulating angiogenesis.

15. The method of claim 10 that is a method of attenuating metastasis.

16. A method of modulating the activity of a plasminogen activator inhibitor (PAI), comprising contacting the PAI with a compound of claim 1, or pharmaceutically acceptable derivatives thereof.

17. A method of modulating the interaction of a plasminogen activator (PA) with a plasminogen activator inhibitor (PAI), comprising contacting the PA or PAI with a compound of claim 1, or pharmaceutically acceptable derivatives thereof, wherein the contacting is effected simultaneously with, prior to, or subsequent to contacting the PA with the PAI.

18. The method of claim 13, wherein the thrombotic disorder or haemostatic disorder is selected from myocardial infarction, thrombosis associated with diabetes or obesity, reocclusion following thrombolytic therapy, deep vein thrombosis, or disseminated intravascular coagulation.

19. The method of claim 13, further comprising administration of tissue plasminogen activator (tPA), wherein the tPA is administered prior to, concurrently with, or subsequent to administration of the compound.

20. The compound [4-(4-hydroxy-3,5-diiodobenzoyl)-2,6-diiodophenoxy]acetic acid benzyl ester, or a pharmaceutically acceptable derivative thereof.

21. A pharmaceutical composition, comprising the compound of claim 20, or a pharmaceutically acceptable derivative thereof, in a pharmaceutically acceptable carrier.

22. The pharmaceutical composition of claim 21 that is formulated for single dosage administration.

23. An article of manufacture, comprising packaging material, a compound of claim 20 or a pharmaceutically acceptable derivative thereof, which is effective for antagonizing a plasminogen activator inhibitor (PAI) or for treatment, prevention or amelioration of one or more symptoms of thrombotic disorders, unstable angina or cancer, and a label that indicates that the compound or pharmaceutically acceptable derivative thereof is used for antagonizing PAI, or for treatment, prevention or amelioration of one or more symptoms of thrombotic disorders, unstable angina or cancer.

24. A method of antagonizing a plasminogen activator inhibitor (PAI), comprising contacting the PAI with a compound of claim 20, or pharmaceutically acceptable derivatives thereof.

25. A method for treating, preventing, or ameliorating one or more symptoms of a plasminogen activator inhibitor (PAI) mediated disorder, comprising administering a compound of claim 20 or a pharmaceutically acceptable derivative thereof.

26. The method of claim 25, wherein the disorder is cancer or a symptom thereof.

27. The method of claim 26, wherein the cancer is selected from the group consisting of tumors, solid tumors, metastatic solid tumors and breast cancer.

28. The method of claim 25, wherein the disorder is a thrombotic disorder, unstable angina or haemostatic disorder.

29. The method of claim 25 that is a method of modulating angiogenesis.

30. The method of claim 25 that is a method of attenuating metastasis.

31. A method of modulating the activity of a plasminogen activator inhibitor (PAI), comprising contacting the PAI with a compound of claim 20, or pharmaceutically acceptable derivatives thereof.

32. A method of modulating the interaction of a plasminogen activator (PA) with a plasminogen activator inhibitor (PAI), comprising contacting the PA or PAI with a compound of claim 20, or pharmaceutically acceptable derivatives thereof, wherein the contacting is effected simultaneously with, prior to, or subsequent to contacting the PA with the PAI.

33. The method of claim 28, wherein the thrombotic disorder or haemostatic disorder is selected from myocardial infarction, thrombosis associated with diabetes or obesity, reocclusion following thrombolytic therapy, deep vein thrombosis, or disseminated intravascular coagulation.

34. The method of claim 28, further comprising administration of tissue plasminogen activator (tPA), wherein the tPA is administered prior to, concurrently with, or subsequent to administration of the compound.

* * * * *

UNITED STATES PATENT AND TRADEMARK OFFICE
CERTIFICATE OF CORRECTION

PATENT NO.    : 6,677,473 B1
DATED         : January 13, 2004
INVENTOR(S)   : Madison et al.

It is certified that error appears in the above-identified patent and that said Letters Patent is hereby corrected as shown below:

Title page,
Item [74], *Attorney, Agent, or Firm*, please replace "Deb Riega" with -- Dale L. Rieger --.

Column 95,
Line 20, please cancel claim 2 and replace with the following claim:
    2.     The compound of claim 1 that has formula (XId):

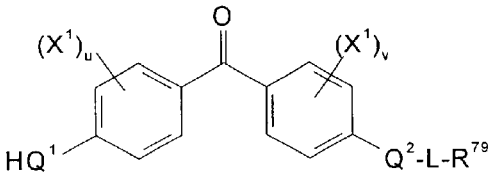

Signed and Sealed this

Twentieth Day of July, 2004

JON W. DUDAS
*Acting Director of the United States Patent and Trademark Office*